US012552784B2

(12) United States Patent
Chen

(10) Patent No.: US 12,552,784 B2
(45) Date of Patent: Feb. 17, 2026

(54) 1H-PYRROLO[2,3-B]PYRIDINE DERIVATIVES AS BCL-2 INHIBITORS FOR THE TREATMENT OF NEOPLASTIC AND AUTOIMMUNE DISEASES

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 700 days.

(21) Appl. No.: 17/787,973

(22) PCT Filed: Dec. 22, 2020

(86) PCT No.: PCT/US2020/066650
§ 371 (c)(1),
(2) Date: Jun. 22, 2022

(87) PCT Pub. No.: WO2021/133817
PCT Pub. Date: Jul. 1, 2021

(65) Prior Publication Data

US 2023/0119463 A1 Apr. 20, 2023

Related U.S. Application Data

(60) Provisional application No. 62/965,325, filed on Jan. 24, 2020.

(30) Foreign Application Priority Data

Dec. 27, 2019 (WO) ................ PCT/US2019/068685

(51) Int. Cl.
*C07D 471/04* (2006.01)
*A61P 35/00* (2006.01)
*C07D 498/14* (2006.01)

(52) U.S. Cl.
CPC ........... *C07D 471/04* (2013.01); *A61P 35/00* (2018.01); *C07D 498/14* (2013.01)

(58) Field of Classification Search
CPC ...... A61P 35/00; C07D 471/04; C07D 498/14
See application file for complete search history.

(56) References Cited

U.S. PATENT DOCUMENTS

| | | | |
|---|---|---|---|
| 7,642,260 | B2 | 1/2010 | Bruncko et al. |
| 7,767,684 | B2 | 8/2010 | Bruncko et al. |
| 7,973,161 | B2 | 7/2011 | Bruncko et al. |
| 8,084,607 | B2 | 12/2011 | Bruncko et al. |
| 8,173,811 | B2 | 5/2012 | Bruncko et al. |
| 8,354,404 | B2 | 1/2013 | Bruncko et al. |
| 8,546,399 | B2 | 10/2013 | Bruncko et al. |
| 8,557,983 | B2 | 10/2013 | Doherty et al. |
| 8,563,735 | B2 | 10/2013 | Bruncko et al. |
| 8,580,794 | B2 | 11/2013 | Doherty et al. |
| 8,586,754 | B2 | 11/2013 | Bruncko et al. |
| 8,614,318 | B2 | 12/2013 | Bruncko et al. |
| 8,686,136 | B2 | 4/2014 | Bruncko et al. |
| 8,691,184 | B2 | 4/2014 | Wang et al. |
| 8,952,157 | B2 | 2/2015 | Ding et al. |
| 9,006,247 | B2 | 4/2015 | Tao et al. |
| 9,029,404 | B2 | 5/2015 | Doherty et al. |
| 9,034,875 | B2 | 5/2015 | Doherty et al. |
| 9,045,420 | B2 | 6/2015 | Doherty et al. |
| 9,045,444 | B2 | 6/2015 | Ding et al. |
| 9,045,475 | B2 | 6/2015 | Elmore et al. |

(Continued)

FOREIGN PATENT DOCUMENTS

| | | | |
|---|---|---|---|
| EP | 2376480 | A2 | 10/2011 |
| WO | 2005/049593 | A2 | 6/2005 |

(Continued)

OTHER PUBLICATIONS

Ettmayer, Peter, Gordon L. Amidon, Bernd Clement, and Bernard Testa. "Lessons learned from marketed and investigational prodrugs." Journal of medicinal chemistry 47, No. 10 (2004): 2393-2404 (Year: 2004).*

(Continued)

*Primary Examiner* — James H Alstrum-Acevedo
*Assistant Examiner* — Carolyn L. Ladd
(74) *Attorney, Agent, or Firm* — McCarter & English, LLP; Yu Lu; Zhongyu Wang

(57) ABSTRACT

The present invention relates to 1H-pyrrolo[2,3-b]pyridine derivatives and related compounds as BCL-2 inhibitors for treating neoplastic, autoimmune or neurodegenerative diseases. The present description discloses the synthesis and characterisation of exemplary compounds as well as pharmacological data thereof (e.g. pages 162 to 233; examples 1 to 8; table; compound examples cpd-1 to cpd-135; biological examples 1 to 4).

(I)

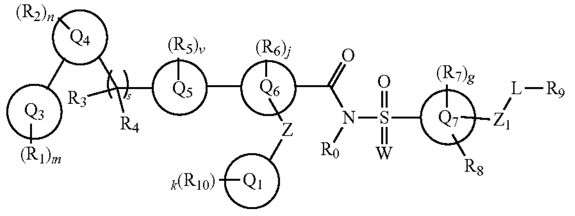

3 Claims, No Drawings

(56) References Cited

U.S. PATENT DOCUMENTS

| | | | |
|---|---|---|---|
| 9,045,920 | B2 | 6/2015 | Minemura |
| 9,072,748 | B2 | 7/2015 | Bruncko et al. |
| 9,073,855 | B2 | 7/2015 | Doherty et al. |
| 9,125,913 | B2 | 9/2015 | Bruncko et al. |
| 9,174,982 | B2 | 11/2015 | Bruncko et al. |
| 9,303,025 | B2 | 4/2016 | Bruncko et al. |
| 9,315,488 | B2 | 4/2016 | Ding et al. |
| 9,403,822 | B2 | 8/2016 | Tao et al. |
| 10,377,755 | B2 | 8/2019 | Chen et al. |
| 11,279,711 | B2 | 3/2022 | Chen et al. |
| 11,365,206 | B2 | 6/2022 | Chen et al. |
| 11,993,610 | B2 | 5/2024 | Chen et al. |
| 2010/0152183 | A1 | 6/2010 | Bruncko et al. |
| 2010/0298321 | A1 | 11/2010 | Bruncko et al. |
| 2010/0298323 | A1 | 11/2010 | Bruncko et al. |
| 2010/0305122 | A1 | 12/2010 | Bruncko et al. |
| 2011/0124628 | A1 | 5/2011 | Bruncko et al. |
| 2012/0108590 | A1 | 5/2012 | Birtalan et al. |
| 2014/0057890 | A1 | 2/2014 | Bruncko et al. |
| 2016/0304451 | A1 | 10/2016 | Elmore et al. |
| 2017/0096424 | A1 | 4/2017 | Tao et al. |
| 2017/0158666 | A1 | 6/2017 | Bruncko et al. |
| 2017/0281649 | A1 | 10/2017 | David |
| 2018/0251426 | A1 | 9/2018 | Bruncko et al. |
| 2020/0071329 | A1 | 3/2020 | Chen et al. |
| 2021/0171523 | A1 | 6/2021 | Chen et al. |
| 2021/0315904 | A1 | 10/2021 | Chen |
| 2021/0332065 | A1 | 10/2021 | Chen |
| 2022/0073513 | A1 | 3/2022 | Chen |
| 2022/0220126 | A1 | 7/2022 | Chen et al. |
| 2022/0372042 | A1 | 11/2022 | Chen |
| 2023/0002369 | A1 | 1/2023 | Xue et al. |
| 2023/0271979 | A1 | 8/2023 | Chen et al. |
| 2024/0166646 | A1 | 5/2024 | Chen |
| 2024/0180924 | A1 | 6/2024 | Chen |
| 2024/0425520 | A1 | 12/2024 | Chen et al. |
| 2025/0051329 | A1 | 2/2025 | Chen et al. |
| 2025/0099481 | A1 | 3/2025 | Chen |
| 2025/0114374 | A1 | 4/2025 | Chen |
| 2025/0179090 | A1 | 6/2025 | Chen et al. |

FOREIGN PATENT DOCUMENTS

| | | | |
|---|---|---|---|
| WO | 2005/049594 | A1 | 6/2005 |
| WO | 2009/036035 | A1 | 3/2009 |
| WO | 2010/065824 | A2 | 6/2010 |
| WO | 2010/065865 | A2 | 6/2010 |
| WO | 2010/138588 | A2 | 12/2010 |
| WO | 2011/068560 | A1 | 6/2011 |
| WO | 2011/068561 | A1 | 6/2011 |
| WO | 2011/149492 | A1 | 12/2011 |
| WO | 2011/150016 | A1 | 12/2011 |
| WO | 2012/058392 | A1 | 5/2012 |
| WO | 2012/071336 | A1 | 5/2012 |
| WO | 2012/121758 | A1 | 9/2012 |
| WO | 2014/165044 | A1 | 10/2014 |
| WO | 2017/132474 | A1 | 8/2017 |
| WO | 2018/127130 | A1 | 7/2018 |
| WO | 2018/192462 | A1 | 10/2018 |
| WO | 2019/040550 | A1 | 2/2019 |
| WO | 2019/040573 | A1 | 2/2019 |
| WO | PCT/CN2019/113776 | | 10/2019 |
| WO | 2020/041405 | A1 | 2/2020 |
| WO | 2020/041406 | A1 | 2/2020 |
| WO | 2020/140005 | A2 | 7/2020 |
| WO | 2021/208963 | A1 | 10/2021 |

OTHER PUBLICATIONS

Braga, Dario, Simone d'Agostino, Elena Dichiarante, Lucia Maini, and Fabrizia Grepioni. "Dealing with crystal forms (the kingdom of serendip?)." Chemistry, An Asian Journal 6, No. 9 (2011): 2214-2223 (Year: 2011).*

'Bond' in IUPAC Compendium of Chemical Terminology, 5th ed. International Union of Pure and Applied Chemistry; 2025. Online version 5.0.0, 2025. https://doi.org/10.1351/goldbook.B00697 (Year: 2025).*

Cancer Research UK, Can cancer be prevented? Retrieved online at: https://www.cancerresearchuk.org/about-cancer/causes-of-cancer/can-cancer-be-prevented-0. 4 pages, (2021).

CNN.com./Health, FDA mulls drug to slow late-stage Alzheimer's. Retrieved online at: http://www.cnn/com/2003/Health/Conditions/09/24/alzheimers.drug.ap/index.html. 2 pages, Sep. 24, 2003.

Damaslo, Alzheimer's Disease and Related Dementias. Cecil Textbook of Medicine. 20th Edition, vol. 2. J. Claude Bennett (Ed.), W.B. Saunders Company, Philadelphia. pp. 1992-1996, (1996).

Golub et al., Molecular classification of cancer: class discovery and class prediction by gene expression monitoring. Science. Oct. 15, 1999;286(5439):531-537.

Lala et al., Role of nitric oxide in tumor progression: lessons from experimental tumors. Cancer Metastasis Rev. 1998;17(1):91-106.

Layzer, Section Five—Degenerative Diseases of the Nervous System. Cecil Textbook of Medicine. 20th Edition, vol. 2. J. Claude Bennett (Ed.), W.B. Saunders Company, Philadelphia. pp. 2050-2057, (1996).

Martin, Is There a Cure for Cancer? Retrieved online at: https://www.webmd.com/cancer/guide/cure-for-cancer. 10 pages, May 17, 2020.

MAYO Clinic, Multiple sclerosis. Retrieved online at: https://www.mayoclinic.org/diseases-conditions/multiple-sclerosis/diagnosis-treatment/drc-20350274. 13 pages, (2021).

MAYO Clinical Staff, Alzheimer's: Drugs help manage symptoms. Retrieved online at: https://www.mayoclinic.org/diseases-conditions/alzheimers-disease/in-depth/alzheimers/art-20048103, 4 pages, (2021).

Pubchem, SCHEMBL 17897155, Compound Summary for CID 24729558. 14 pages. Retrieved online at: https://pubchem.ncbi.nlm.nih.gov/compound/24729558. Mar. 4, 2017.

Souers et al., ABT-199, a potent and selective BCL-2 inhibitor, achieves antitumor activity while sparing platelets. Nat Med. Feb. 2013;19(2):202-8.

Stella, Prodrugs: Some thoughts and current issues. J Pharm Sci. Dec. 2010;99(12):4755-65.

STN Accession No. 2017:1256516, 3 pages, (2022).

International Search Report and Written Opinion for Application No. PCT/US2018/047411, dated Oct. 1, 2018, 8 bages.

International Search Report and Written Opinion for Application No. PCT/US2018/047444, dated Oct. 8, 2018, 9 pages.

International Search Report and Written Opinion for Application No. PCT/US2019/047403, dated Oct. 17, 2019, 12 bages.

International Search Report and Written Opinion for Application No. PCT/US2019/047404, dated Oct. 9, 2019, 10 pages.

International Search Report and Written Opinion for Application No. PCT/US2019/068685, dated Jun. 29, 2020, 19 pages.

International Search Report and Written Opinion for Application No. PCT/US2020/020010, dated Jun. 3, 2020, 10 pages.

International Search Report and Written Opinion for Application No. PCT/US2020/066650, dated Mar. 29, 2021, 18 pages.

Davis et al., Amorphous solid dispersions of BCS class II drugs: A rational approach to solvent and polymer selection. Chemical Engineering Research and Design. 2016;110:192-199.

Patani et al., Bioisosterism: A Rational Approach in Drug Design. Chem Rev. Dec. 19, 1996;96(8):3147-3176.

PubChem SID 152035716, AKOS015896297. 5 pages, Jun. 2, 2019.

International Search Report and Written Opinion for Application No. PCT/US2021/064278, dated Apr. 4, 2022, 10 pages.

International Search Report and Written Opinion for Application No. PCT/US2022/034518, dated Sep. 19, 2022, 5 pages.

International Search Report and Written Opinion for Application No. PCT/US2022/053328, dated Mar. 17, 2023, 9 pages.

* cited by examiner

1H-PYRROLO[2,3-B]PYRIDINE DERIVATIVES AS BCL-2 INHIBITORS FOR THE TREATMENT OF NEOPLASTIC AND AUTOIMMUNE DISEASES

REFERENCE TO RELATED APPLICATIONS

This application is a U.S. national stage application, filed under 35 U.S.C. § 371 (c), of International Application No. PCT/US2020/066650, filed on Dec. 22, 2020, which claims the benefit of priority to International Patent Application No. PCT/US2019/068685, filed on Dec. 27, 2019, published as WO2020/140005 on Jul. 2, 2020. International Application No. PCT/US2020/066650 also claims the benefit of the filing date of U.S. Provisional Patent Application No. 62/965,325, filed on Jan. 24, 2020. The entire contents of the above referenced applications are incorporated herein by reference.

BACKGROUND OF THE INVENTION

Apoptosis, or programmed cell death, is a conserved and regulated process that is the primary mechanism for the removal of aged, damaged and unnecessary cells. The ability to block apoptotic signaling is a key hallmark of cancer and is thus important for oncogenesis, tumor maintenance and chemoresistance [Hanahan, D. & Weinberg, R. A. The hallmarks of cancer. Cell 100, 57-70 (2000).]. Dynamic binding interactions between prodeath (for example, BCL-2-associated X protein (BAX), BCL-2 antagonist/killer 1 (BAK), BCL-2-associated agonist of cell death (BAD), BCL-2-like 11 (BIM), NOXA and BCL-2 binding component 3 (PUMA)) and prosurvival (BCL-2, BCL-XL, BCL-2-like 2 (BCL-W), myeloid cell leukemia sequence 1 (MCL-1) and BCL-2-related protein A1 (BFL-1)) proteins in the BCL-2 family control commitment to programmed cell death. Altering the balance among these opposing factions provides one means by which cancer cells undermine normal apoptosis and gain a survival advantage [Youle, R. J. &

Strasser, A. The BCL-2 protein family: opposing activities that mediate cell death. Nat. Rev. Mol. Cell Biol. 9, 47-59 (2008)].

BCL-2, the first identified apoptotic regulator, was originally cloned from the breakpoint of a t(14;18) translocation present in human B cell lymphomas [Tsujimoto, Y., et al. Science 228, 1440-1443 (1985); Cleary, M. L., et al Cell 47, 19-28 (1986); Boise, L. H. et al. Cell 74, 597-608 (1993)]. This protein has since been shown to have a dominant role in the survival of multiple lymphoid malignancies [Vaux, D. L., et al pre-B cells. Nature 335, 440-442 (1988)]. Overexpression of Bcl-2 proteins correlates with resistance to chemotherapy, clinical outcome, disease progression, overall prognosis or a combination thereof in various cancers and disorders of the immune system. Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in PCT/US2004/36770, published as WO 2005/049593, and PCT/US2004/37911, published as WO/2005/049594. Involvement of Bcl-2 proteins in immune and autoimmune diseases is described in Current Allergy and Asthma Reports 2003, 3, 378-384; British Journal of Hematology 2000, 110(3), 584-90; Blood 2000, 95(4), 1283-92; and New England Journal of Medicine 2004, 351(14), 1409-1418. Involvement of Bcl-2 proteins in arthritis is disclosed in WO 2009/064938. Involvement of Bcl-2 proteins in bone marrow transplant rejection is disclosed in US 2008-0182845 A1. All incorporated herein by reference.

In the last decade, several Bcl-2 inhibitors such as ABT-737, ABT-263, and ABT-199 as shown below have been identified and entered human clinical trials for cancers treatment.

ABT-737

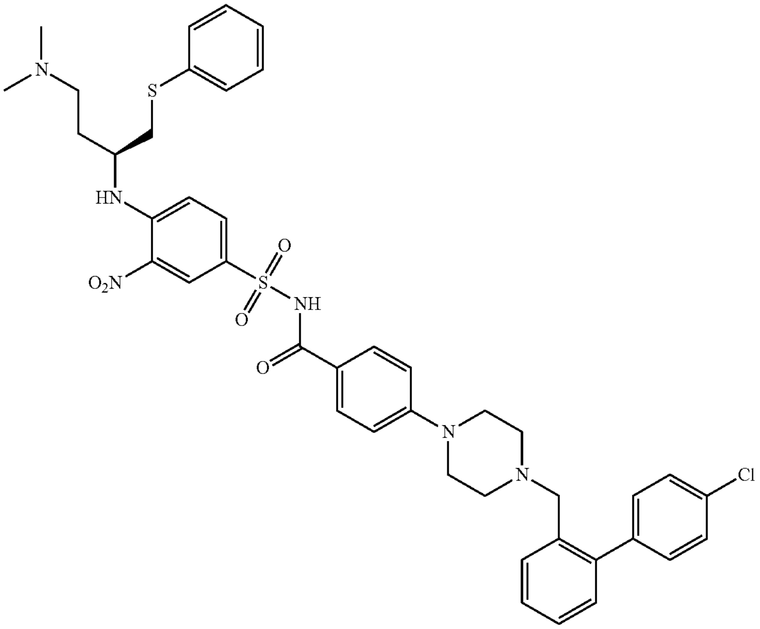

-continued

ABT-263

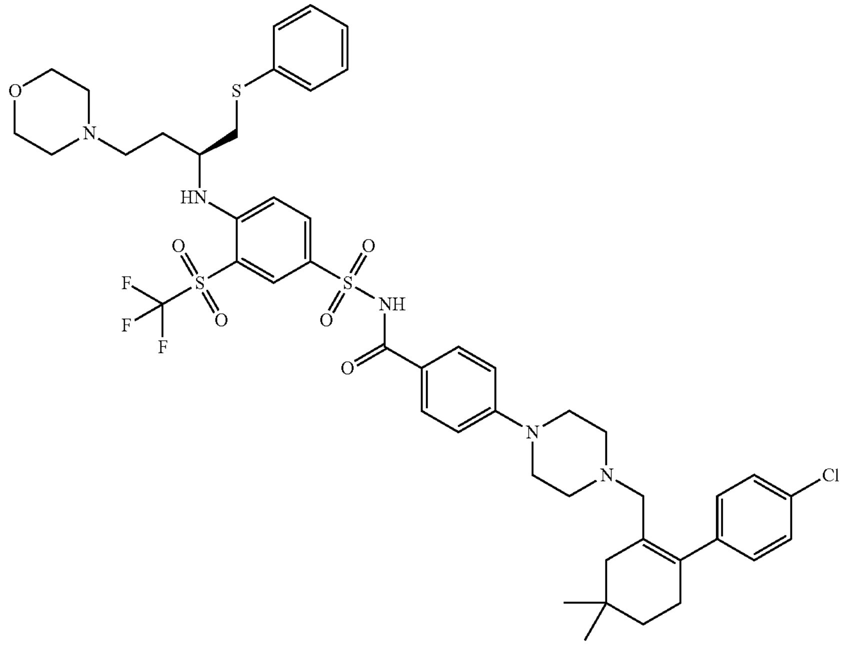

ABT-199

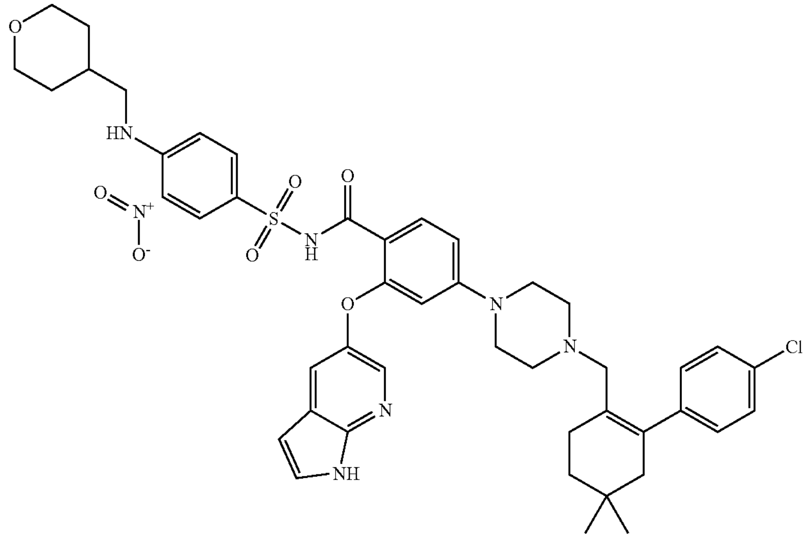

ABT-737 is discovered by nuclear magnetic resonance (NMR)-based screening, parallel synthesis and structure based fragment drug design [Tillman Oltersdorf, et al, Nature, Vol 435, 2005, p 677]. ABT-737 a small-molecule inhibitor of the anti-apoptotic proteins Bcl-2, Bcl-XL and Bcl-w, with an affinity two to three orders of magnitude more potent than previously reported compounds. Mechanistic studies reveal that ABT-737 does not directly initiate the apoptotic process, but enhances the effects of death signals, displaying synergistic cytotoxicity with chemotherapeutics and radiation. ABT-737 exhibits single-agent-mechanism-based killing of cells from lymphoma and small-cell lung carcinoma lines, as well as primary patient-derived cells, and in animal models, ABT-737 improves survival, causes regression of established tumors, and produces cures in a high percentage of the mice. Unfortunately, ABT-737 is not orally bioavailable, and its formulation for intravenous delivery is hampered by its low aqueous solubility.

After extensive MedChem effort, an orally bioavailable Bcl-2 inhibitor ABT-263 (Navitoclax) has been developed [Cheol-Min Park, et al J. Med. Chem. 2008, 51, 6902-6915]. ABT-263 is a potent inhibitor of Bcl-xL, Bcl-2 and Bcl-w with Ki of ≤0.5 nM, ≤1 nM and ≤1 nM. ABT-263 has an $IC_{50}$ of 110 nM against SCLC H146 cell line. When ABT-263 is administered at 100 mg/kg/day in the H345 xenograft model, significant antitumor efficacy is observed with 80% TGI and 20% of treated tumors indicating at least a 50% reduction in tumor volume. Oral administration of ABT-263 alone causes complete tumor regressions in xenograft models of small-cell lung cancer and acute lymphoblastic leukemia [Tse C, et al. Cancer Res. 2008, 68(9), 3421-3428]. In the clinical trial, however, the inhibition of BCL-XL by ABT-263 (navitoclax) induces a rapid, concentration-dependent decrease in the number of circulating platelets. This mechanism-based thrombocytopenia is the dose-limiting toxicity of single-agent navitoclax treatment in patients and limits the ability to drive drug concentrations into a highly efficacious range.

Thus, a BCL-2 selective (BCL-XL sparing) inhibitor would culminate in substantially reduced thrombocytopenia while maintaining efficacy in lymphoid malignancies. The resulting increase in the therapeutic window should allow for greater BCL-2 suppression and clinical efficacy in BCL-2-dependent tumor types. After extensive MedChem, ABT-199 (GDC-0199) has been successfully developed [Andrew J Souers, et al, Nature Medicine, Volume 19, 22, p 202, 2013]. ABT-199 is a Bcl-2-selective inhibitor with Ki of ≤0.01 nM, >4800-fold more selective versus Bcl-xL and Bcl-w, and no activity to Mcl-1. ABT-199 potently inhibits RS4;11 cells with $EC_{50}$ of 8 nM. In addition, ABT-199 induces a rapid apoptosis in RS4;11 cells with cytochrome c release, caspase activation, and the accumulation of sub-G0/G1 DNA. Quantitative immunoblotting reveals that sensitivity to ABT-199 correlated strongly with the expression of Bcl-2, including NHL, DLBCL, MCL, AML and ALL cell lines. ABT-199 also induces apoptosis in CLL with an average $EC_{50}$ of 3.0 nM. A single dose of 100 mg/kg of ABT-199 causes a maximal tumor growth inhibition of 95% and tumor growth delay of 152% in RS4;11 xenografts. ABT-199 also inhibits xenograft growth (DoHH2, Granta-519) as a single agent or in combination with Bendamustine and other agents. Human Phase I and II data showed that ABT-199 is highly efficacious for CLL who have 17p deletion, and was approved by FDA in 2016.

WO/2017/132474, WO/2019/040550, and WO/2019/040573 disclosed a novel class of BCL-2 inhibitors. However, there is still a strong need for continuing search in this field of art for more potent BCL-2 inhibitor.

SUMMARY OF THE INVENTION

In a first embodiment, this invention provides compounds of the Formula (0) or an N-oxide thereof, or a pharmaceutically acceptable salt, solvate, polymorph, tautomer, stereoisomer, an isotopic form, or a prodrug of said compound of Formula (0) or N-oxide thereof:

Formula (0)

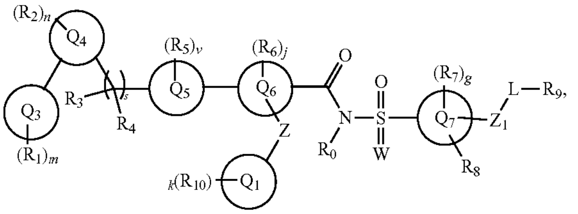

wherein

Z is —O—, —P(=O)($R_c$)—, —C($R_aR_b$)—, C(=C($R_aR_b$))—, —Si($R_aR_b$)—, —C(O)—, —N($R^0$)—, —S(=O)(=$NR_c$)—, $Q_1$ is 6-9 membered heteroaryl;

$Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is cycloalkyl, cycloalkenyl, heterocycloalkyl, heterocycloalkenyl, aryl, heteroaryl, or spiro heterocyclic;

$Q_6$ is 6-membered aryl, or 5-6 membered heteroaryl;

$Q_7$ is 6-membered aryl or 5-6 membered heteroaryl, each of which is optionally fused with a benzene, heteroarene, cycloalkane, cycloalkene, heterocycloalkane, or heterocycloalkene;

each of $R_0$, and $R^0$, independently, is H or alkyl;

each of $R_1$, $R_2$, $R_3$, $R_4$, $R_5$, $R_6$, $R_7$, $R_8$, $R_9$, and $R_{10}$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, NH$(CH_2)_pR_a$, C(O)$R_a$, S(O)$R_a$, $SO_2R_a$, C(O)O$R_a$, OC(O)$R_a$, $NR_bR_c$, C(O)N($R_b$)$R_c$, N($R_b$)C(O)$R_c$, —P(O)$R_bR_c$, -alkyl-P(O)$R_bR_c$, —S(O)(=N($R_b$))$R_c$, —N=S(O)$R_bR_c$, =$NR_b$, $SO_2$N($R_b$)$R_c$, or N($R_b$)$SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, —P(O)$R_eR_e$, -alkyl-P(O)$R_eR_e$, —S(O)(=N($R_e$))$R_e$, —N=S(O)$R_eR_e$, =$NR_e$, C(O)NHOH, C(O)OH, C(O)$NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

W is O or N($R_a$);

$Z_1$ is a bond, $(CH_2)_p$, N(H), O, S, C(O), S($O_2$), OC(O), C(O)O, $OSO_2$, S($O_2$)O, C(O)S, SC(O), C(O)C(O), C(O)N(H), N(H)C(O), S($O_2$)N(H), N(H)S($O_2$), OC(O)O, OC(O)S, OC(O)N(H), N(H)C(O)O, N(H)C(O)S, N(H)C(O)N(H), $(CH_2)_p$N(H)$(CH_2)_q$, $(CH_2)_p$N(H)C(O)$(CH_2)_q$, $(CH_2)_p$C(O)N(H)$(CH_2)_q$, OC(O)N(H)$(CH_2)_{p+1}$N(H)$(CH_2)_q$, a bivalent alkenyl group, or a bivalent alkynyl group;

L is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

$R_0$ and $R_a$ group, taken together with the atom to which they are attached, may optionally form a cycloalkyl or heterocycloalkyl, in which said cycloalkyl or heterocycloalkyl, is optionally substituted with one or more $R_d$;

$R_0$ and $R_{10}$ group, taken together with the atom to which they are attached, may optionally form a cycloalkyl or heterocycloalkyl, in which said cycloalkyl or heterocycloalkyl, is optionally substituted with one or more $R_d$;

two of $R_1$ group, taken together with the atom to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$, is optionally substituted with one or more $R_d$;

$R_3$ and $R_4$ group, taken together with the atom to which they are attached, may optionally form a cycloalkyl or heterocycloalkyl, in which said cycloalkyl or heterocycloalkyl of $R_3$ or $R_4$, is optionally substituted with one or more $R_d$;

two of $R_5$ group, taken together with the atom to which they are attached, may optionally form a cycloalkyl or heterocycloalkyl, in which said cycloalkyl or heterocycloalkyl of $R_5$, is optionally substituted with one or more $R_d$;

$R_7$ and $R_8$ group, taken together with the atom to which they are attached, may optionally form a cycloalkyl or heterocycloalkyl, in which said cycloalkyl or heterocycloalkyl of $R_7$ or $R_8$, is optionally substituted with one or more $R_d$;

$R_7$ and —$Z_1$-L-$R_9$ group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of $R_7$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_d$ group, taken together with the atom to which they are attached, may optionally form a cycloalkyl, or heterocycloalkyl, in which said cycloalkyl or heterocycloalkyl of $R_d$, is optionally substituted with one or more $R_e$;

two of $R_e$ group, taken together with the atom to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of g and j is, independently, 0, 1, 2, or 3;

each of n, v and k is, independently, 0, 1, 2, 3, 4, 5, 6, 7, or 8;

s is 0 or 1; and each of m, p, and q is, independently, 0, 1, 2, 3, 4, or 5.

In certain embodiments, the invention provides a compound represented by Formula (I):

Formula (I)

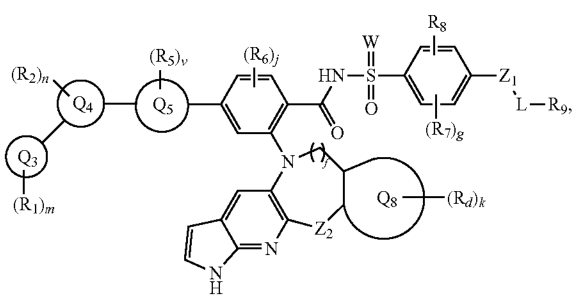

wherein $Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is cycloalkyl, cycloalkenyl, heterocycloalkyl, heterocycloalkenyl, aryl, heteroaryl, or spiro-heterocyclic;

$Q_8$ is cycloalkyl, cycloalkenyl, heterocycloalkyl, heterocycloalkenyl, aryl, heteroaryl, or spiro-heterocyclic;

each of $R_1$, $R_2$, $R_5$, $R_6$, $R_7$, $R_8$, and $R_9$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(=N(R_b))R_c$, $—N=S(O)R_bR_c$, $=NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, $—P(O)R_eR_e$, -alkyl-$P(O)R_eR_e$, $—S(O)(=N(R_e))R_e$, $—N=S(O)R_eR_e$, $=NR_e$, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

W is O or $N(R_a)$;

each of $Z_1$ and $Z_2$, independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

L is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

two of $R_1$ group, taken together with the atom to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$, is optionally substituted with one or more $R_d$;

two of $R_5$ group, taken together with the atom to which they are attached, may optionally form a cycloalkyl or heterocycloalkyl, in which said cycloalkyl or heterocycloalkyl of $R_5$, is optionally substituted with one or more $R_d$;

$R_7$ and $R_8$ group, taken together with the atom to which they are attached, may optionally form a cycloalkyl or heterocycloalkyl, in which said cycloalkyl or heterocycloalkyl of $R_7$ or $R_8$, is optionally substituted with one or more $R_d$;

$R_7$ and —$Z_1$-L-$R_9$ group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of $R_7$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_d$ group, taken together with the atom to which they are attached, may optionally form a cycloalkyl, or heterocycloalkyl, in which said cycloalkyl or heterocycloalkyl of $R_d$, is optionally substituted with one or more $R_e$;

two of $R_e$ group, taken together with the atom to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of m, n, j, k, v and g is, independently, 0, 1, 2, 3, 4, 5, 6, 7, or 8;

f is 0, 1, or 2; and each of p, and q is, independently, 0, 1, 2, 3, 4, or 5.

In certain embodiments, the invention provides a compound represented by Formula (II):

Formula (II)

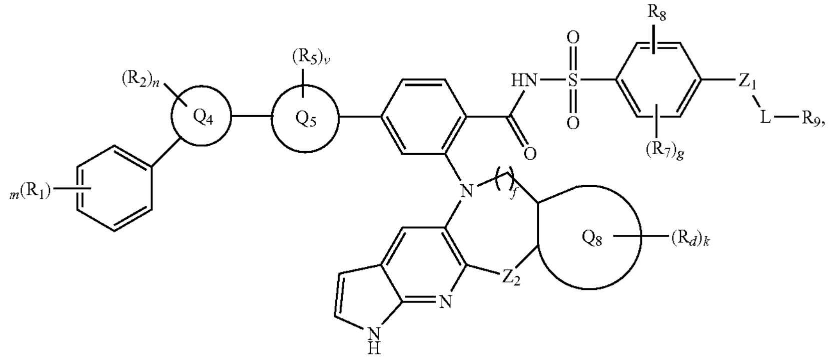

wherein $Q_4$ is heterocycloalkyl; and $Q_5$ is aryl or spiro heterocyclic.

In certain embodiments, the invention provides a compound represented by Formula (III):

Formula (III)

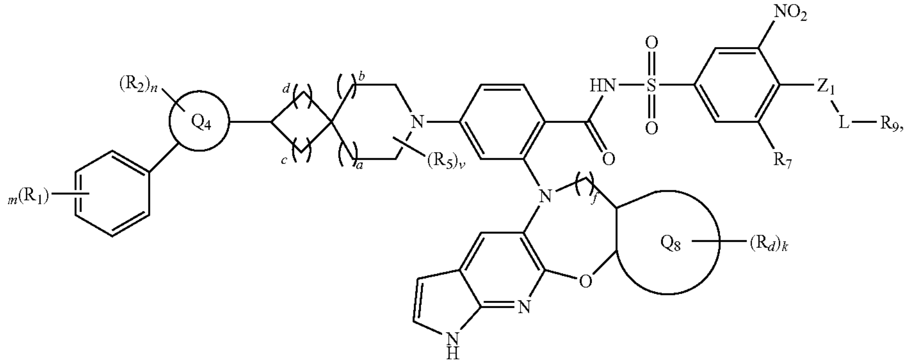

wherein each of a, b, c, and d, independently, is 0, 1, or 2.

In certain embodiments, the invention provides a compound represented by Formula (IV):
Formula (IV)
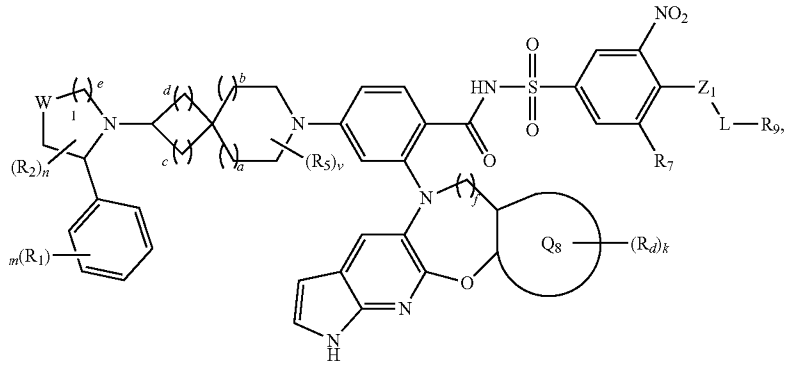
wherein e is 0, 1, or 2; and $W_1$ is O, S, $N(R_a)$, $C(R_aR_b)$.
In certain embodiments, the invention provides a compound represented by Formula (V),
Formula (V)
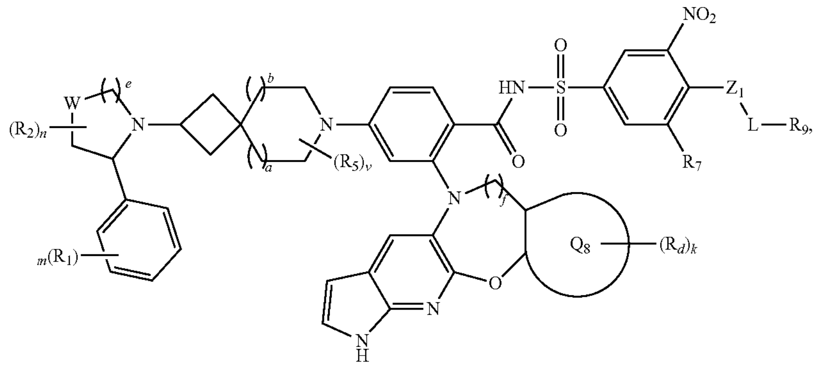
In certain embodiments, the invention provides a compound represented by Formula (VI):
Formula (VI)
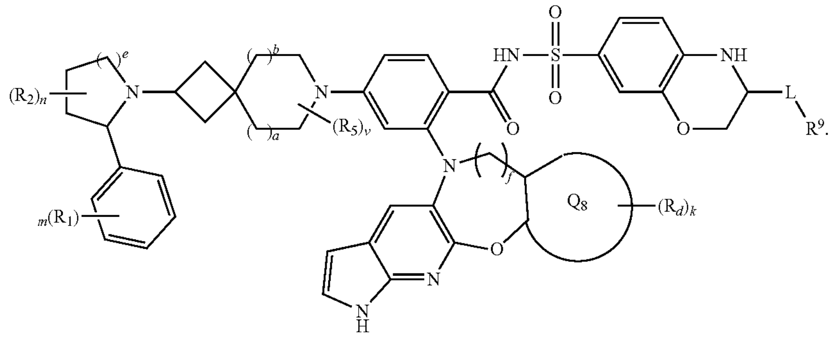

In certain embodiments, the invention provides a compound represented by Formula (A):

Formula (A)

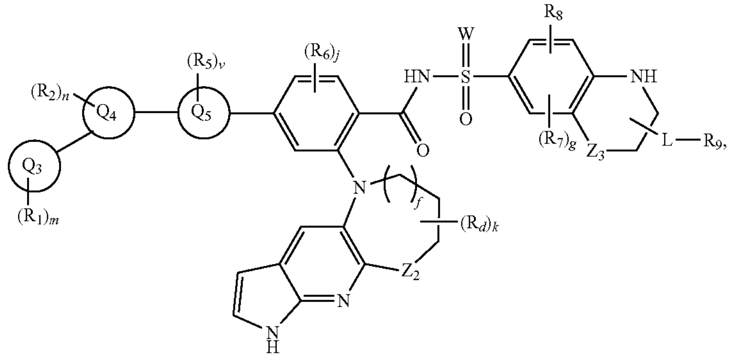

wherein $Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is cycloalkyl, cycloalkenyl, heterocycloalkyl, heterocycloalkenyl, aryl, heteroaryl, or spiro-heterocyclic;

each of $R_1$, $R_2$, $R_5$, $R_6$, $R_7$, $R_8$, and $R_9$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(═N(R_b))R_c$, $—N═S(O)R_bR_c$, $═NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, ═O, $—P(O)R_eR_e$, -alkyl-$P(O)R_eR_e$, $—S(O)(═N(R_e))R_e$, $—N═S(O)R_eR_e$, $═NR_e$, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, ═O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

W is O or $N(R_a)$;

each of $Z_1$, and $Z_3$, independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

L is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

two of $R_1$ group, taken together with the atom to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$, is optionally substituted with one or more $R_d$;

two of $R_5$ group, taken together with the atom to which they are attached, may optionally form a cycloalkyl or heterocycloalkyl, in which said cycloalkyl or heterocycloalkyl of $R_5$, is optionally substituted with one or more $R_d$; $R_7$ and $R_8$ group, taken together with the atom to which they are attached, may optionally form a cycloalkyl or heterocycloalkyl, in which said cycloalkyl or heterocycloalkyl of $R_7$ or $R_8$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_e$ group, taken together with the atom to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of m, n, j, v, k, and g is, independently, 0, 1, 2, 3, 4, 5, 6, 7, or 8;

f is 0, 1, or 2; and each of p, and q is, independently, 0, 1, 2, 3, 4, or 5.

In certain embodiments, the invention provides a compound represented by Formula (B):

Formula (B)

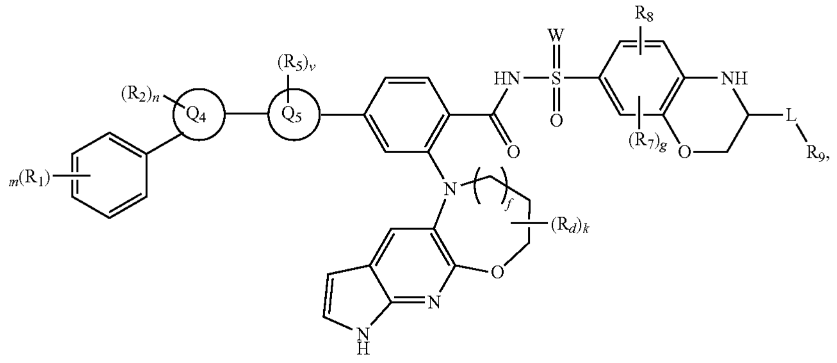

wherein $Q_4$ is heterocycloalkyl; and $Q_5$ is aryl or spiro heterocyclic.

In certain embodiments, the invention provides a compound represented by Formula (C):

Formula (C)

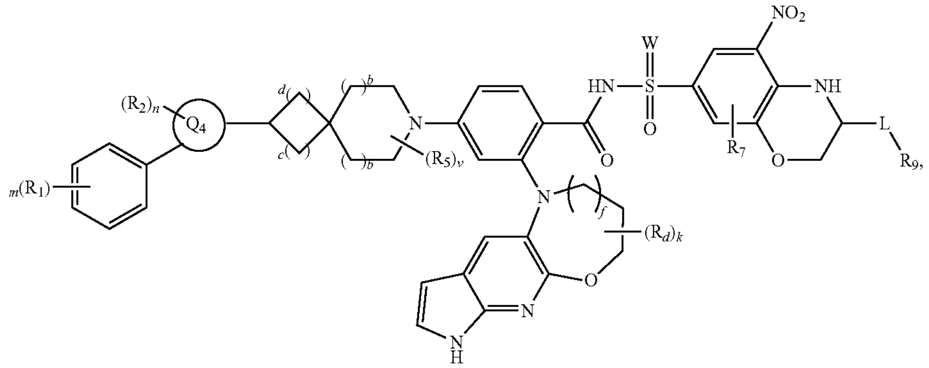

wherein each of a, b, c, and d, independently, is 0, 1, or 2.

In certain embodiments, the invention provides a compound represented by Formula (D):

Formula (D)

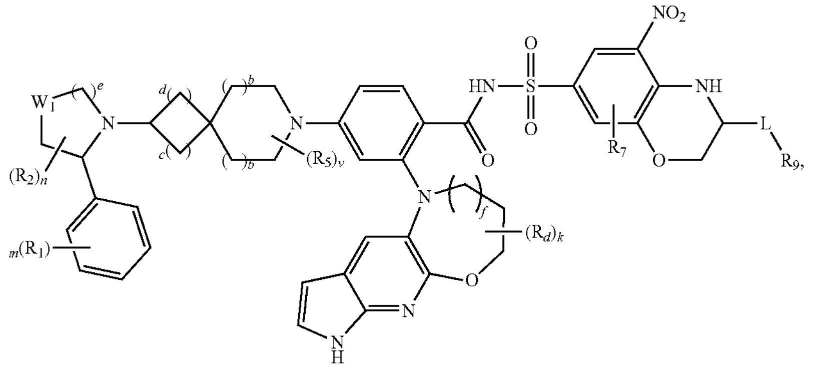

wherein e is 0, 1, or 2; and $W_1$ is O, S, $N(R_a)$, $C(R_aR_b)$.

In certain embodiments, the invention provides a compound represented by Formula (E):

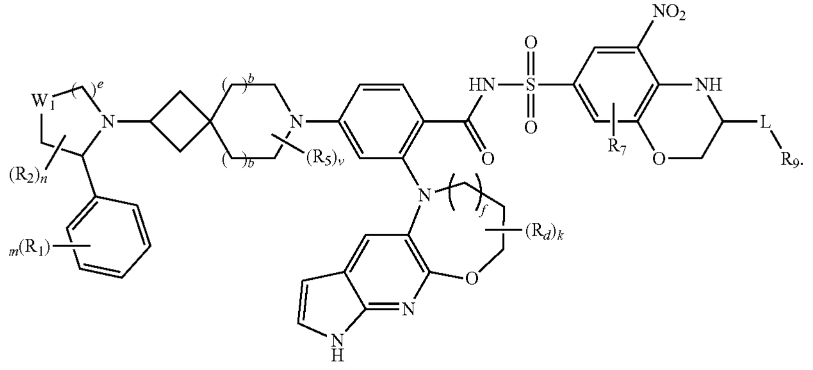

In certain embodiments, the invention provides a compound represented by Formula (i):

Formula (i)

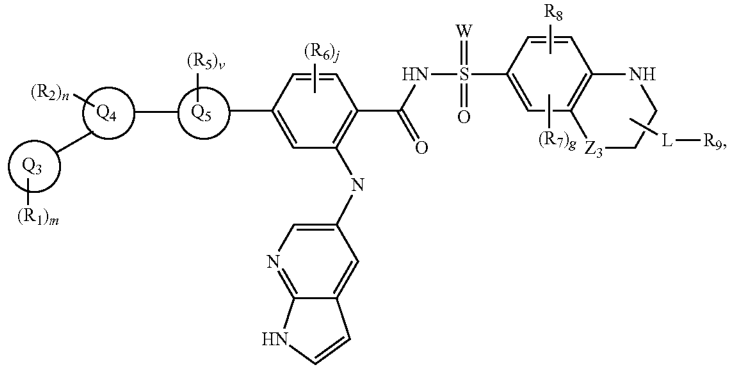

wherein $Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is cycloalkyl, cycloalkenyl, heterocycloalkyl, heterocycloalkenyl, aryl, heteroaryl, or spiro-heterocyclic;

each of $R_1$, $R_2$, $R_5$, $R_6$, $R_7$, $R_8$, and $R_9$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(=N(R_b))R_c$, $—N=S(O)R_bR_c$, $=NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, $=O$, $—P(O)R_eR_e$, -alkyl-$P(O)R_eR_e$, $—S(O)(=N(R_e))R_e$, $—N=S(O)R_eR_e$, $=NR_e$, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, $=O$, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

W is O or $N(R_a)$;

each of $Z_1$, $Z_2$ and $Z_3$, independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

L is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

two of $R_1$ group, taken together with the atom to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$, is optionally substituted with one or more $R_d$;

two of $R_5$ group, taken together with the atom to which they are attached, may optionally form a cycloalkyl or heterocycloalkyl, in which said cycloalkyl or heterocycloalkyl of $R_5$, is optionally substituted with one or more $R_d$;

$R_7$ and $R_8$ group, taken together with the atom to which they are attached, may optionally form a cycloalkyl or heterocycloalkyl, in which said cycloalkyl or heterocycloalkyl of $R_7$ or $R_8$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_e$ group, taken together with the atom to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of m, n, j, v, and g is, independently, 0, 1, 2, 3, 4, 5, 6, 7, or 8; and, each of p, and q is, independently, 0, 1, 2, 3, 4, or 5.

In certain embodiments, the invention provides a compound represented by Formula (ii):

Formula (ii)

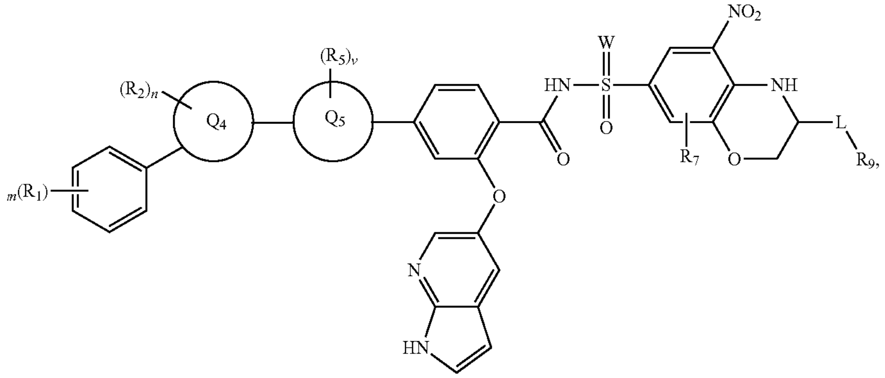

wherein $Q_4$ is heterocycloalkyl; and $Q_5$ is aryl or spiro heterocyclic.

In certain embodiments, the invention provides a compound represented by Formula (iii):

Formula (iii)

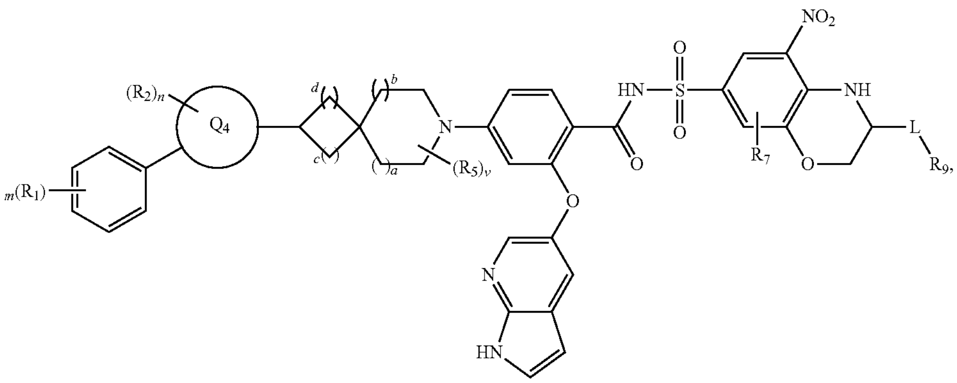

wherein each of a, b, c, and d, independently, is 0, 1, or 2.

In certain embodiments, the invention provides a compound represented by Formula (iv):

Formula (iv)

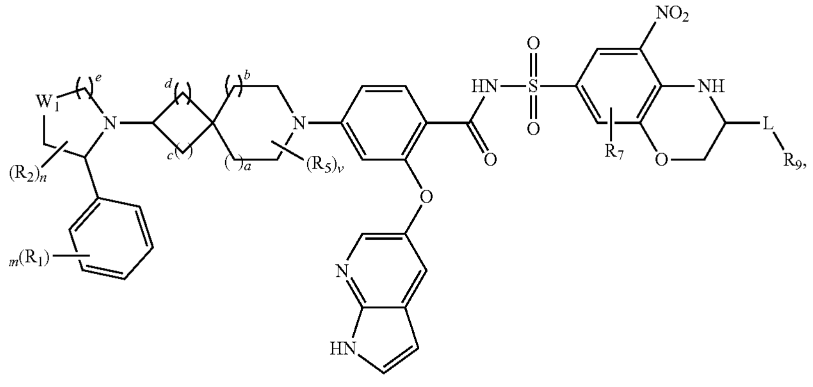

wherein e is 0, 1, or 2; and $W_1$ is O, S, $N(R_a)$, $C(R_aR_b$.

In certain embodiments, the invention provides a compound represented by Formula (v):

Formula (v)

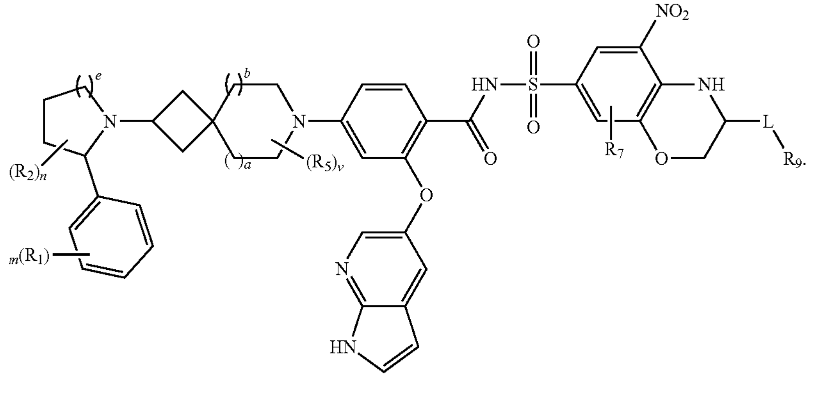

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

Also within the scope of this invention is a pharmaceutical composition containing one or more of the compounds (such as any one of those in Formulae (I)-(VI), (A)-(E), (i)-(v), any of the compounds listed in Parts 1-5), or a pharmaceutically acceptable salt, solvate, polymorph, tautomer, stereoisomer, an isotopic form, or a prodrug thereof or an N-oxide thereof), modifications, and/or salts thereof described herein, and a pharmaceutically acceptable diluent or carrier; as well as said pharmaceutical composition for use in treating a neoplastic disease, therapeutic uses thereof, and use of the compounds for the manufacture of a medicament for treating the disease/disorder. Also provided is use of any one or more of said compounds or pharmaceutical compositions in the manufacture of a medicament for treating said disease/disorder.

This invention also relates to a method of treating a neoplastic disease, an autoimmune disease, or a neurodegenerative disease, comprising administering to a subject in need thereof an effective amount of one or more compounds of the invention (such as any one of those in Formulae (I)-(VI), (A)-(E), (i)-(v), any of the compounds listed in Parts 1-5), or a pharmaceutically acceptable salt, solvate, polymorph, tautomer, stereoisomer, an isotopic form, or a prodrug thereof or an N-oxide thereof), modifications, and/or salts thereof described herein, or a pharmaceutical composition comprising the compound(s) of the invention.

In certain embodiments, the neoplastic disease, autoimmune disease, or neorodegenerative disease is characterized by abnormal (e.g., enhanced or increased) Bcl-2 activity. For example, the neoplastic disease can be a hematological malignancy or cancer including solid tumor; the autoimmune disease can be type I diabetes; and the neorodegenerative disease can be schizophrenia.

In certain embodiments, the neoplastic disease is myeloma, multiple myeloma, lymphoma, follicular lymphoma (FL), non-Hodgkin's lymphoma, leukemia, acute leukemia, acute lymphoblastic leukemia (ALL) (such as BCL-2-dependent ALL and pediatric ALL), chronic lymphoblastic leukemia (CLL) (such as relapsed/refractory CLL, del(17p) CLL), chronic myeloid leukemia (CML) (such as blast-crisis CML), mantle cell lymphoma (MCL), diffuse large B-cell lymphoma, lung cancer such as small cell lung cancer (SCLC), melanoma, breast cancer, or prostate cancer, including drug-resistant cancer thereof.

In certain embodiments, the method further comprises administering one or more further treatment(s) effective to treat the neoplastic disease, such as surgery, radiation therapy, a chemotherapeutic agent (such as bendamustine, NL-101 (7-(5-(bis(2-chloroethyl)amino)-1-methyl-1H-benzo[d]imidazol-2-yl)-N-hydroxyheptanamide), cisplatin, carboplatin, etoposide, topotecan), a target thearpy (e.g., an anti-CD20 antibody such as rituximab, a Bruton's tyrosine kinase inhibitor such as ibrutinib and acalabrutinib (ACP-196), a PI3Kδ inhibitor such as idelalisib); an antibody-drug conjugate or ADC (such as anti-CD30 ADC brentuximab vedotin), an immunotherapy (such as an anti-PD-1 antibody including pembrolizumab and nivolumab, or an anti-PD-L1 antibody including atezolizumab, durvalumab, and avelumab), or a CAR-T thearpy (such as tisagenlecleucel, axicabtagene ciloleucel).

Also provided herein is the use of one or more compounds of the invention, or a pharmaceutically acceptable salt thereof, or a pharmaceutical composition comprising one or more compounds of the invention, for the preparation of a medicament for the treatment of the above-referenced diseases or conditions.

In another embodiment, provided herein the compounds of the invention, or a pharmaceutically acceptable salt thereof, or a pharmaceutical composition comprising one or more of the disclosed compounds are for use in treating the above-referenced diseases or conditions.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

Part 1

4-(4-((4'-chloro-5,5-dimethyl-3,4,5,6-tetrahydro-[1,1'-biphenyl]-2-yl)methyl)piperazin-1-yl)-2-(methyl(1H-pyrrolo[2,3-b]pyridin-5-yl)phosphoryl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(methyl(1H-pyrrolo[2,3-b]pyridin-5-yl)phosphoryl)benzamide, 6-(4-((4'-chloro-5,5-dimethyl-3,4,5,6-tetrahydro-[1,1'-biphenyl]-2-yl)methyl)piperazin-1-yl)-2-((3-nitro-4-(((tetrahydro-2H-pyran-4-yl)methyl)amino)phenyl)sulfonyl)-4-(1H-pyrrolo[2,3-b]pyridin-5-yl)-3,4-dihydroisoquinolin-1(2H)-one, 2-((4-((((S)-1,4-dioxan-2-yl)methyl)amino)-3-nitrophenyl)sulfonyl)-6-(4-((4'-chloro-5,5-dimethyl-3,4,5,6-tetrahydro-[1,1'-biphenyl]-2-yl)methyl)piperazin-1-yl)-4-(1H-pyrrolo[2,3-b]pyridin-5-yl)-3,4-dihydroisoquinolin-1(2H)-one, 2-(1-(1H-pyrrolo[2,3-b]pyridin-5-yl)vinyl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, (R)-2-(1-(1H-pyrrolo[2,3-b]pyridin-5-yl)ethyl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, (S)-2-(1-(1H-pyrrolo[2,3-b]pyridin-5-yl)ethyl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(1-hydroxy-1-(1H-pyrrolo[2,3-b]pyridin-5-yl)ethyl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(1-hydroxy-1-(1H-pyrrolo[2,3-b]pyridin-5-yl)ethyl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(dimethyl(1H-pyrrolo[2,3-b]pyridin-5-yl)silyl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(1H-pyrrolo[2,3-b]pyridine-5-sulfonimidoyl)benzamide, 4-(4-((4'-chloro-5,5-dimethyl-3,4,5,6-tetrahydro-[1,1'-biphenyl]-2-yl)methyl)piperazin-1-yl)-2-(methyl(1H-pyrrolo[2,3-b]pyridin-5-yl)amino)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(1H-pyrrolo[2,3-b]pyridine-5-carbonyl)benzamide, N-((4-((((S)-1,4-dioxan-2-yl)methyl)amino)-3-nitrophenyl)sulfonyl)-2-(1-(1H-pyrrolo[2,3-b]pyridin-5-yl)ethyl)-4-(4-((4'-chloro-5,5-dimethyl-3,4,5,6-tetrahydro-[1,1'-biphenyl]-2-yl)methyl)piperazin-1-yl)benzamide, 2-(1-(1H-pyrrolo[2,3-b]pyridin-5-yl)ethyl)-4-(4-((4'-chloro-5,5-dimethyl-3,4,5,6-tetrahydro-[1,1'-biphenyl]-2-yl)methyl)piperazin-1-yl)-N-((4-((2-morpholinoethyl)amino)-3-nitrophenyl)sulfonyl)benzamide, Part 2

4'-(2-(2-cyclopropylphenyl)pyrrolidin-1-yl)-3-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-[1,1'-biphenyl]-4-carboxamide, 4'-(2-(2-cyclopropylphenyl)pyrrolidin-1-yl)-3-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)-[1,1'-biphenyl]-4-carboxamide, N-((4-((((S)-1,4-dioxan-2-yl)methyl)amino)-3-nitrophenyl)sulfonyl)-4'-(2-(2-cyclopropylphenyl)pyrrolidin-1-yl)-3-(2,3-dihydropyrrolo[3',2':5,6]pyrido[2,3-b][1,4]oxazin-1(6H)-yl)-[1,1'-biphenyl]-4-carboxamide, 4'-(2-(2-cyclopropylphenyl)-4-methylpiperazin-1-yl)-3-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-[1,1'-biphenyl]-4-carboxamide, N-((4-((((S)-1,4-dioxan-2-yl)methyl)amino)-3-nitrophenyl)sulfonyl)-4'-(2-(2-cyclopropylphenyl)-4-methylpiperazin-1-yl)-3-(2,3-dihydropyrrolo[3',2':5,6]pyrido[2,3-b][1,4]oxazin-1(6H)-yl)-[1,1'-biphenyl]-4-carboxamide, 4'-(2-(2-cyclopropylphenyl)-4-methylpiperazin-1-yl)-3-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)-[1,1'-biphenyl]-4-carboxamide, 4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)benzamide, (S)-4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-4-(2-(2-(o-tolyl)pyrrolidin-1-yl)-7-azaspiro[3.5]nonan-7-yl)benzamide, (S)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-4-(2-(2-(2-vinylphenyl)pyrrolidin-1-yl)-7-azaspiro[3.5]nonan-7-yl)benzamide, (S)-2-(2,3-dihydropyrrolo[3',2':5,6]pyrido[2,3-b][1,4]oxazin-1(6H)-yl)-4-(2-(2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-4-(2-(2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-4-(2-(2-(2-ethynylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-4-(2-(2-(2-(prop-1-yn-1-yl)phenyl)pyrrolidin-1-yl)-7-azaspiro[3.5]nonan-7-yl)benzamide, (S)-4-(2-(2-(2-cyclobutylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(2-(2-(2-cyclopentylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(2-(2-(2-cyclohexylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(2-(2-(2-(tert-butyl)phenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-4-(2-(2-(2-(trifluoromethyl)phenyl)pyrrolidin-1-yl)-7-azaspiro[3.5]nonan-7-yl)benzamide, (S)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)-4-(2-(2-(2-(1,1,1-trifluoro-2-methylpropan-2-yl)phenyl)pyrrolidin-1-yl)-7-azaspiro[3.5]nonan-7-yl)benzamide, (S)-4-(2-(2-(2-(2-cyanopropan-2-yl)phenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-2-(2,3-dihydropyrrolo[3',2':5,6]pyrido[2,3-b][1,4]oxazin-1(6H)-yl)-4-(2-(2-(2-(2-hydroxypropan-2-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, (S)-4-(2-(2-(2-(2-aminopropan-2-yl)phenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(2-(2-(2-cyclopropylphenyl)-4-methylpiperazin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(2-((S)-2-(2-cyclopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(2-(2-(2-cyclopropylphenyl)-4-methylpiperazin-1-yl)-7-azaspiro[3.5]nonan-7-yl)-2-(2,3-dihydropyrrolo[3',2':5,6]pyrido[2,3-b][1,4]oxazin-1(6H)-yl)benzamide, 4-(2-(2-(2-cyclopropylphenyl)-4-methylpiperazin-1-yl)-7-azaspiro[3.5]nonan-7-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (S)-4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(2-(2-(2-cyclopropylphenyl)pyrrolidin-1-yl)-7-azaspiro[3.5]nonan-7-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(2-((R)-2-(2-cyclopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(7-(2-(2-cyclopropylphenyl)pyrrolidin-1-yl)-2-azaspiro[3.5]nonan-2-yl)-2-((R)-3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(6-(2-(2-cyclopropylphenyl)pyrrolidin-1-yl)-2-azaspiro[3.3]heptan-2-yl)-2-((R)-3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(9-(2-(2-cyclopropylphenyl)pyrrolidin-1-yl)-3-azaspiro[5.5]undecan-3-yl)-2-((R)-3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(7-(2-(2-cyclopropylphenyl)pyrrolidin-1-yl)-2-azaspiro[3.5]nonan-2-yl)-2-((R)-3-methyl-2,3-dihydropyrrolo[3',2':5,6]pyrido[2,3-b][1,4]oxazin-1(6H)-yl)benzamide, N-((4-((((S)-1,4-dioxan-2-yl)methyl)amino)-3-nitrophenyl)sulfonyl)-4-(6-(2-(2-cyclopropylphenyl)pyrrolidin-1-yl)-2-azaspiro[3.3]heptan-2-yl)-2-((R)-3-methyl-2,3-dihydropyrrolo[3',2':5,6]pyrido[2,3-b][1,4]oxazin-1(6H)-yl)benzamide, N-((4-((((S)-1,4-dioxan-2-yl)methyl)amino)-3-nitrophenyl)sulfonyl)-4-(9-(2-(2-cyclopropylphenyl)pyrrolidin-1-yl)-3-azaspiro[5.5]undecan-3-yl)-2-((R)-3-methyl-2,3-dihydropyrrolo[3',2':5,6]pyrido[2,3-b][1,4]oxazin-1(6H)-yl)benzamide, 4'-(2-(2-cyclopropylphenyl)pyrrolidin-1-yl)-3-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)-[1,1'-biphenyl]-4-carboxamide, 4'-(2-(2-cyclopropylphenyl)pyrrolidin-1-yl)-3-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)-[1,1'-biphenyl]-4-carboxamide, N-((4-((((S)-1,4-dioxan-2-yl)methyl)amino)-3-nitrophenyl)sulfonyl)-4'-(2-(2-cyclopropylphenyl)pyrrolidin-1-yl)-3-(3,4-dihydro-2H-pyrrolo[3',2':5,6]pyrido[2,3-b][1,4]oxazepin-1(7H)-yl)-[1,1'-biphenyl]-4-carboxamide, 4'-(2-(2-cyclopropylphenyl)-4-methylpiperazin-1-yl)-3-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)-[1,1'-biphenyl]-4-carboxamide, N-((4-((((S)-1,4-dioxan-2-yl)methyl)amino)-3-nitrophenyl)sulfonyl)-4'-(2-(2-cyclopropylphenyl)-4-methylpiperazin-1-yl)-3-(3,4-dihydro-2H-pyrrolo[3',2':5,6]pyrido[2,3-b][1,4]oxazepin-1(7H)-yl)-[1,1'-biphenyl]-4-carboxamide, 4'-(2-(2-cyclopropylphenyl)-4-methylpiperazin-1-yl)-3-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)-[1,1'-biphenyl]-4-carboxamide, 4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, N-(1-(4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)phenyl)vinyl)-4-(((4-fluorotetrahydro-2H-pyran-4-yl)methyl)amino)-3-nitrobenzenesulfonamide, N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, 4-(2-(2-(2-cyclopropylphenyl)-4-methylpiperazin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(2-(2-(2-cyclopropylphenyl)-4-methylpiperazin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, 4-(2-(2-(2-cyclopropylphenyl)-4-methylpiperazin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, N-((4-((((S)-1,4-dioxan-2-yl)methyl)amino)-3-nitrophenyl)sulfonyl)-4-(2-((S)-2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-ethylphenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-vinylphenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-ethynylphenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-4-(2-((S)-2-(2-cyclobutylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-(trifluoromethyl)phenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-4-(2-((S)-2-(2-(tert-butyl)phenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, N-((4-((((S)-1,4-dioxan-2-yl)methyl)amino)-3-nitrophenyl)sulfonyl)-4-(2-((S)-2-(2-(2-aminopropan-2-yl)phenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(2-((S)-2-(2-(2-hydroxypropan-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-((4-((((1s,4s)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-((4-((((1s,4s)-4-methoxy-4-methylcyclohexyl)methyl)amino)-3-nitrophenyl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide, N-((4-((((S)-1,4-dioxan-2-yl)methyl)amino)-3-nitrophenyl)sulfonyl)-4-(2-((R)-2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(7-(2-(2-cyclopropylphenyl)pyrrolidin-1-yl)-2-azaspiro[3.5]nonan-2-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(6-(2-(2-cyclopropylphenyl)pyrrolidin-1-yl)-2-azaspiro[3.3]heptan-2-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(9-(2-(2-cyclopropylphenyl)pyrrolidin-1-yl)-3-azaspiro[5.5]undecan-3-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(7-(2-(2-cyclopropylphenyl)-4-methylpiperazin-1-yl)-2-azaspiro[3.5]nonan-2-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(6-(2-(2-cyclopropylphenyl)-4-methylpiperazin-1-yl)-2-azaspiro[3.3]heptan-2-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(9-(2-(2-cyclopropylphenyl)-4-methylpiperazin-1-yl)-3-azaspiro[5.5]undecan-3-yl)-2-(3,4-dihydro-2H-pyrrolo[3',2':5,6]pyrido[2,3-b][1,4]oxazepin-1(7H)-yl)benzamide, Part 3

List 3-1:

4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((3-nitro-4-(((tetrahydro-2H-pyran-4-yl)methyl)amino)phenyl)sulfonyl)-4-(2-((S)-2-(2-(prop-1-en-2-yl)phenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, 4-(2-((S)-2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethynylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(trifluoromethyl)phenyl)pyrrolidin-1-yl)-7-azaspiro[3.5]nonan-7-yl)benzamide, 4-(2-((S)-2-(2-(tert-butyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-(2-methylpent-3-yn-2-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(trifluoromethyl)phenyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, 4-(2-((S)-2-(2-ethynylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-(tert-butyl)phenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, 4-(2-((S)-2-(2-cyclobutylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((4-((((1s,4s)-4-hydroxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(trifluoromethyl)phenyl)pyrrolidin-1-yl)-7-azaspiro[3.5]nonan-7-yl)benzamide, N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, 4-(2-((S)-2-(2-ethynylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-(tert-butyl)phenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, 4-(2-((S)-2-(2-cyclobutylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1s,4s)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-(((4-fluorotetrahydro-2H-pyran-4-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((1r,4R)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((1s,4S)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((1r,4S)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((1s,4R)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((3R)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-5-nitro-3-(pyridin-2-ylmethyl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-(((4-fluorotetrahydro-2H-pyran-4-yl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((4-((((1s,4s)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-5-nitro-3-(tetrahydro-2H-pyran-4-yl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((S)-1,4-dioxan-2-yl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(6-((S)-

2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide 4-(6-((S)-2-(2-isopropylphenyl)pyrrolidin-1-yl)-2-azaspiro[3.3]heptan-2-yl)-N-(((R)-3-((1r,4R)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-((1s,4S)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((1r,4S)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((1s,4R)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((3R)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-(morpholinomethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-(morpholinomethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-((4,4-difluoropiperidin-1-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-((4,4-difluoropiperidin-1-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-((4-methylpiperazin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((4-methylpiperazin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide N-(((R)-3-(isopropoxymethyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(isopropoxymethyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-5-nitro-3-(pyridin-2-ylmethyl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-5-nitro-3-(pyridin-2-ylmethyl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-(((4-fluorotetrahydro-2H-pyran-4-yl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((S)-1,4-dioxan-2-yl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((1r,4r)-4-methoxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-5-nitro-3-(tetrahydro-2H-pyran-4-yl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((S)-3-((S)-1,4-dioxan-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-((1s,4S)-4-hydroxycyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-((1r,4R)-4-methoxy-4-methylcyclohexyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-(morpholinomethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-((4,4-difluoropiperidin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-((4-methylpiperazin-1-yl)methyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-3-(isopropoxymethyl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-(((R)-5-nitro-3-(pyridin-2-ylmethyl)-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((1r,4r)-4-hydroxy-4-methylcyclohexyl)methyl)amino)-3-nitrophenyl)sulfonyl)-4-(6-((S)-2-(2-(prop-1-en-2-yl)phenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-ethylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-cyclopropylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(2-vinylphenyl)pyrrolidin-1-yl)-2-azaspiro[3.3]heptan-2-yl)benzamide, 4-(6-((S)-2-(2-ethynylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(2-(trifluoromethyl)phenyl)pyrrolidin-1-yl)-2-azaspiro[3.3]heptan-2-yl)benzamide, 4-(6-((S)-2-(2-cyclobutylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-(tert-butyl)phenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(2-(1,1,1-trifluoro-2-methylpropan-2-yl)phenyl)pyrrolidin-1-yl)-2-azaspiro[3.3]heptan-2-yl)benzamide, N-((4-((((1s,4s)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, N-((4-((((1s,4s)-4-hydroxy-4-methylcyclohexyl)methyl)amino)-3-nitrophenyl)sulfonyl)-4-(6-((S)-2-(2-(prop-1-en-2-yl)phenyl)pyrrolidin-1-yl)-2-azaspiro[3.3]heptan-2-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-cyclopropylphenyl)pyrrolidin-1-yl)-2-azaspiro[3.3]heptan-2-yl)-N-((4-((((1s,4s)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-ethylphenyl)pyrrolidin-1-yl)-2-azaspiro[3.3]heptan-2-yl)-N-((4-((((1s,4s)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)-4-(6-((S)-2-(2-vinylphenyl)pyrrolidin-1-yl)-2-azaspiro[3.3]heptan-2-yl)benzamide, List 3-2:

4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((3-nitro-4-(((tetrahydro-2H-pyran-4-yl)methyl)amino)phenyl)sulfonyl)-4-(2-((S)-2-(2-(prop-1-en-2-yl)phenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, 4-(2-((S)-2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethynylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-(trifluoromethyl)phenyl)pyrrolidin-1-yl)-7-azaspiro[3.5]nonan-7-yl)benzamide, 4-(2-((S)-2-(2-(tert-butyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-(2-methylpent-3-yn-2-yl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1s,4s)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-(((4-fluorotetrahydro-2H-pyran-4-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((3-((1r,4r)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((1r,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((1s,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((1r,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((1s,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((3R)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro

[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((1s,4s)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((4-((((1r,4r)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-((4-((((1s,4s)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((S)-1,4-dioxan-2-yl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]

heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-((1r,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-((1s,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((1r,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((1s,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((3R)-3-((5R)-5-methyl-4-(oxetan-3-yl)morpholin-2-yl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((4,4-difluoropiperidin-1-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((4,4-difluoropiperidin-1-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-3-((4-methylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-3-((4-methylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-(isopropoxymethyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-(isopropoxymethyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((R)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, 4-(6-((S)-2-(2-isopropylphenyl)pyrrolidin-1-yl)-2-azaspiro[3.3]heptan-2-yl)-N-(((S)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, List 3-3:

4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, 2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, 2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, 2-((6aS,10aR)-6,6a,7,8,10,10a-hexahydropyrano[4,3-f]pyrrolo[3',2':5,6]pyrido[2,3-b][1,4]oxazepin-5(1H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, 2-((6aR,10aS)-6,6a,7,8,10,10a-hexahydropyrano[4,3-f]pyrrolo[3',2':5,6]pyrido[2,3-b][1,4]oxazepin-5(1H)-yl)-N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-((4-((((1r,4r)-4-hydroxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide, 2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide, 2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-isopropylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((R)-3-((1s,4S)-4-hydroxycyclohexyl)-5-nitro-3,4-dihydro-2H-benzo[b][1,4]oxazin-7-yl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((R)-3-((1r,4R)-4-hydroxycyclohexyl)-5-nitro-3,4-dihydro-2H-benzo[b][1,4]oxazin-7-yl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((S)-3-((1s,4R)-4-hydroxycyclohexyl)-5-nitro-3,4-dihydro-2H-benzo[b][1,4]oxazin-7-yl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((S)-3-((1r,4S)-4-hydroxycyclohexyl)-5-nitro-3,4-dihydro-2H-benzo[b][1,4]oxazin-7-yl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((R)-3-((1r,4R)-4-hydroxy-4-methylcyclohexyl)-5-nitro-3,4-dihydro-2H-benzo[b][1,4]oxazin-7-yl)sulfonyl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-ethylphenyl)pyrrolidin-1-yl)-7-azaspiro[3.5]nonan-7-yl)-N-(((R)-3-((1s,4S)-4-hydroxy-4-methylcyclohexyl)-5-nitro-3,4-dihydro-2H-benzo[b][1,4]oxazin-7-yl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-ethylphenyl)pyrrolidin-1-yl)-7-azaspiro[3.5]nonan-7-yl)-N-(((S)-3-((1r,4S)-4-hydroxy-4-methylcyclohexyl)-5-nitro-3,4-dihydro-2H-benzo[b][1,4]oxazin-7-yl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-ethylphenyl)pyrrolidin-1-yl)-7-azaspiro[3.5]nonan-7-yl)-N-(((S)-3-((1s,4R)-4-hydroxy-4-methylcyclohexyl)-5-nitro-3,4-dihydro-2H-benzo[b][1,4]oxazin-7-yl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-ethylphenyl)pyrrolidin-1-yl)-7-azaspiro[3.5]nonan-7-yl)-2-((6aR,10aR)-6,6a,7,8,10,10a-hexahydropyrano[4,3-f]pyrrolo[3',2':5,6]pyrido[2,3-b][1,4]oxazepin-5(1H)-yl)-N-(((R)-3-(morpholinomethyl)-5-nitro-3,4-dihydro-2H-benzo[b][1,4]oxazin-7-yl)sulfonyl)benzamide, 4-(2-((S)-2-(2-ethylphenyl)pyrrolidin-1-yl)-7-azaspiro[3.5]nonan-7-yl)-2-((6aS,10aS)-6,6a,7,8,10,10a-hexahydropyrano[4,3-f]pyrrolo[3',2':5,6]pyrido[2,3-b][1,4]oxazepin-5(1H)-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aS,10aR)-6,6a,7,8,10,10a-hexahydropyrano[4,3-f]pyrrolo[3',2':5,6]pyrido[2,3-b][1,4]oxazepin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aR,10aS)-6,6a,7,8,10,10a-hexahydropyrano[4,3-f]pyrrolo[3',2':5,6]pyrido[2,3-b][1,4]oxazepin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-ethylphenyl)pyrrolidin-1-yl)-7-azaspiro[3.5]nonan-7-yl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-ethylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-ethylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((S)-3-(isopropoxymethyl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-ethylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((4-((((1r,4r)-4-hydroxy-4-methylcyclohexyl)methyl)amino)-3-nitrophenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-((4-((((1r,4r)-4-methoxy-4-methylcyclohexyl)methyl)amino)-3-nitrophenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((R)-5-nitro-3-(tetrahydro-2H-pyran-4-yl)-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((S)-5-nitro-3-(tetrahydro-2H-pyran-4-yl)-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((R)-3-((1s,4S)-4-hydroxycyclohexyl)-5-nitro-3,4-dihydro-2H-benzo[b][1,4]oxazin-7-yl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((R)-3-((1r,4R)-4-hydroxycyclohexyl)-5-nitro-3,4-dihydro-2H-benzo[b][1,4]oxazin-7-yl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((S)-3-((1s,4R)-4-hydroxycyclohexyl)-5-nitro-3,4-dihydro-2H-benzo[b][1,4]oxazin-7-yl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((S)-3-((1r,4S)-4-hydroxycyclohexyl)-5-nitro-3,4-dihydro-2H-benzo[b][1,4]oxazin-7-yl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-2-((6aR,9aS)-6a,7,9,9a-tetrahydro-1H-furo[3,4-f]pyrrolo

[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-N-(((R)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-N-(((S)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(o-tolyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(o-tolyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)-4-(2-((S)-2-(o-tolyl)pyrrolidin-1-yl)-7-azaspiro[3.5]nonan-7-yl)benzamide, N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, N-(((R)-3-((4-methylpiperazin-1-yl)methyl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((S)-3-((4-methylpiperazin-1-yl)methyl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((S)-3-(isopropoxymethyl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-(((S)-5-nitro-3-(pyridin-2-ylmethyl)-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(o-tolyl)pyrrolidin-1-yl)-7-azaspiro[3.5]nonan-7-yl)benzamide, N-((3-nitro-4-(((tetrahydro-2H-pyran-4-yl)methyl)amino)phenyl)sulfonyl)-4-(2-((S)-2-(2-(prop-1-en-2-yl)phenyl)pyrrolidin-1-yl)-7-azaspiro[3.5]nonan-7-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-methoxy-4-methylcyclohexyl)methyl)amino)-3-nitrophenyl)sulfonyl)-4-(2-((S)-2-(2-(prop-1-en-2-yl)phenyl)pyrrolidin-1-yl)-7-azaspiro[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan- 7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 2-((6aR,10aR)-6,6a,7,8,10,10a-hexahydropyrano[4,3-f]pyrrolo[3',2':5,6]pyrido[2,3-b][1,4]oxazepin-5(1H)-yl)-N-(((R)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-N-(((S)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-(prop-1-en-2-yl)phenyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-(prop-1-en-2-yl)phenyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((R)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro

[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((S)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, N-(((S)-3-(isopropoxymethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((S)-5-nitro-3-(pyridin-2-ylmethyl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((4-((((1r,4r)-4-hydroxy-4-methylcyclohexyl)methyl)amino)-3-nitrophenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((R)-3-((1s,4S)-4-hydroxycyclohexyl)-5-nitro-3,4-dihydro-2H-benzo[b][1,4]oxazin-7-yl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((R)-3-((1r,4R)-4-hydroxycyclohexyl)-5-nitro-3,4-dihydro-2H-benzo[b][1,4]oxazin-7-yl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((S)-3-((1s,4R)-4-hydroxycyclohexyl)-5-nitro-3,4-dihydro-2H-benzo[b][1,4]oxazin-7-yl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((S)-3-((1r,4S)-4-hydroxycyclohexyl)-5-nitro-3,4-dihydro-2H-benzo[b][1,4]oxazin-7-yl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((R)-3-((1r,4R)-4-hydroxy-4-methylcyclohexyl)-5-nitro-3,4-dihydro-2H-benzo[b][1,4]oxazin-7-yl)sulfonyl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-cyclopropylphenyl)pyrrolidin-1-yl)-7-azaspiro[3.5]nonan-7-yl)-N-(((R)-3-((1s,4S)-4-hydroxy-4-methylcyclohexyl)-5-nitro-3,4-dihydro-2H-benzo[b][1,4]oxazin-7-yl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-cyclopropylphenyl)pyrrolidin-1-yl)-7-azaspiro[3.5]nonan-7-yl)-N-(((S)-3-((1r,4S)-4-hydroxy-4-methylcyclohexyl)-5-nitro-3,4-dihydro-2H-benzo[b][1,4]oxazin-7-yl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-cyclopropylphenyl)pyrrolidin-1-yl)-7-azaspiro[3.5]nonan-7-yl)-N-(((S)-3-((1s,4R)-4-hydroxy-4-methylcyclohexyl)-5-nitro-3,4-dihydro-2H-benzo[b][1,4]oxazin-7-yl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 4-(2-((S)-2-(2-cyclopropylphenyl)pyrrolidin-1-yl)-7-azaspiro[3.5]nonan-7-yl)-2-((6aR,10aR)-6,6a,7,8,10,10a-hexahydropyrano[4,3-f]pyrrolo[3',2':5,6]pyrido[2,3-b][1,4]oxazepin-5(1H)-yl)-N-(((R)-3-(morpholinomethyl)-5-nitro-3,4-dihydro-2H-benzo[b][1,4]oxazin-7-yl)sulfonyl)benzamide, 4-(2-((S)-2-(2-cyclopropylphenyl)pyrrolidin-1-yl)-7-azaspiro[3.5]nonan-7-yl)-2-((6aS,10aS)-6,6a,7,8,10,10a-hexahydropyrano[4,3-f]pyrrolo[3',2':5,6]pyrido[2,3-b][1,4]oxazepin-5(1H)-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aS,10aR)-6,6a,7,8,10,10a-hexahydropyrano[4,3-f]pyrrolo[3',2':5,6]pyrido[2,3-b][1,4]oxazepin-5(1H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aR,10aS)-6,6a,7,8,10,10a-hexahydropyrano[4,3-f]pyrrolo[3',2':5,6]pyrido[2,3-b][1,4]oxazepin-5(1H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-cyclopropylphenyl)pyrrolidin-1-yl)-7-azaspiro[3.5]nonan-7-yl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, 4-(2-((S)-2-(2-cyclopropylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-cyclopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((S)-3-(isopropoxymethyl)-5-nitro-3,4-dihydro-2H-benzo[b][1,4]oxazin-7-yl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-((4-((((1r,4r)-4-hydroxy-4-methylcyclohexyl)methyl)amino)-3-nitrophenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, 4-(2-((S)-2-(2-ethynylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-yn-1-yl)phenyl)pyrrolidin-1-yl)-7-azaspiro[3.5]nonan-7-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, 4-(2-((S)-2-(2-(tert-butyl)phenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-(((S)-3-((S)-1,4-dioxan-2-yl)-5-nitro-3,4-dihydro-2H-benzo[b][1,4]oxazin-7-yl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(2-(trifluoromethyl)phenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(2-methylpent-3-yn-2-yl)phenyl)pyrrolidin-1-yl)-7-azaspiro[3.5]nonan-7-yl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-(2-hydroxypropan-2-yl)phenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, 4-(2-((S)-2-(2-(2-cyanopropan-2-yl)phenyl)pyrrolidin-1-yl)-7-azaspiro[3.5]nonan-7-yl)-N-(((R)-3-((1s,4S)-4-hydroxycyclohexyl)-5-nitro-3,4-dihydro-2H-benzo[b][1,4]oxazin-7-yl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-(2-cyanopropan-2-yl)phenyl)pyrrolidin-1-yl)-7-azaspiro[3.5]nonan-7-yl)-N-(((R)-3-((1r,4R)-4-hydroxycyclohexyl)-5-nitro-3,4-dihydro-2H-benzo[b][1,4]

oxazin-7-yl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-(2-cyanopropan-2-yl)phenyl)pyrrolidin-1-yl)-7-azaspiro[3.5]nonan-7-yl)-N-(((S)-3-((1s,4R)-4-hydroxycyclohexyl)-5-nitro-3,4-dihydro-2H-benzo[b][1,4]oxazin-7-yl)sulfonyl)-2-((5aR,9aR)-5a,8,9,9a-tetrahydro-6H-pyrano[4,3-b]pyrrolo[3',2':5,6]pyrido[3,2-e][1,4]oxazin-5(1H)-yl)benzamide, 4-(2-((S)-2-(2-(2-cyanopropan-2-yl)phenyl)pyrrolidin-1-yl)-7-azaspiro[3.5]nonan-7-yl)-N-(((S)-3-((1r,4S)-4-hydroxycyclohexyl)-5-nitro-3,4-dihydro-2H-benzo[b][1,4]oxazin-7-yl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((R)-3-(2-isopropylphenyl)morpholino)-7-azaspiro[3.5]nonan-7-yl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-5-(2-(prop-1-en-2-yl)phenyl)-1,4-oxazepan-4-yl)-7-azaspiro[3.5]nonan-7-yl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)-4-(6-((S)-2-(o-tolyl)pyrrolidin-1-yl)-2-azaspiro[3.3]heptan-2-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, 4-(6-((S)-2-(2-cyclopropylphenyl)pyrrolidin-1-yl)-2-azaspiro[3.3]heptan-2-yl)-2-((6aR,10aR)-6,6a,7,8,10,10a-hexahydropyrano[4,3-f]pyrrolo[3',2':5,6]pyrido[2,3-b][1,4]oxazepin-5(1H)-yl)-N-(((R)-3-(morpholinomethyl)-5-nitro-3,4-dihydro-2H-benzo[b][1,4]oxazin-7-yl)sulfonyl)benzamide, 2-((6aS,10aS)-6,6a,7,8,10,10a-hexahydropyrano[4,3-f]pyrrolo[3',2':5,6]pyrido[2,3-b][1,4]oxazepin-5(1H)-yl)-4-((S)-6-methyl-2-((S)-2-(o-tolyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, Part 4

N-((3-(1,4-dioxan-2-yl)-5-nitro-3,4-dihydro-2H-benzo[b][1,4]oxazin-7-yl)sulfonyl)-4-(2-(2-(2-cyclopropylphenyl)-4-methylpiperazin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide, 4-(2-(2-(2-cyclopropylphenyl)-4-methylpiperazin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-((5-nitro-3-(tetrahydro-2H-pyran-4-yl)-3,4-dihydro-2H-benzo[b][1,4]oxazin-7-yl)sulfonyl)benzamide, 4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)-N-((3-(morpholinomethyl)-5-nitro-3,4-dihydro-2H-benzo[b][1,4]oxazin-7-yl)sulfonyl)benzamide, 4-(2-(2-(2-cyclopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-((3-((4-methylpiperazin-1-yl)methyl)-5-nitro-3,4-dihydro-2H-benzo[b][1,4]oxazin-7-yl)sulfonyl)benzamide, 2-(2,3-dihydropyrrolo[3',2':5,6]pyrido[2,3-b][1,4]oxazin-1(6H)-yl)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 4-(2-((S)-2-(2-ethylphenyl)pyrrolidin-1-yl)-7-azaspiro[3.5]nonan-7-yl)-2-((S)-3-methyl-2,3-dihydropyrrolo[3',2':5,6]pyrido[2,3-b][1,4]oxazin-1(6H)-yl)-N-(((S)-5-nitro-3-(tetrahydro-2H-pyran-4-yl)-3,4-dihydro-2H-benzo[b][1,4]oxazin-7-yl)sulfonyl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-((S)-1,4-dioxan-2-yl)-5-nitro-3,4-dihydro-2H-benzo[b][1,4]oxazin-7-yl)sulfonyl)-2-((R)-2-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5]nonan-7-yl)benzamide, 4-(2-((S)-2-(2-cyclopropylphenyl)pyrrolidin-1-yl)-7-azaspiro[3.5]nonan-7-yl)-2-((S)-2-methyl-2,3-dihydropyrrolo[3',2':5,6]pyrido[2,3-b][1,4]oxazin-1(6H)-yl)-N-(((3S)-3-((5R)-5-methyl-4-(oxetan-3-yl)morpholin-2-yl)-5-nitro-3,4-dihydro-2H-benzo[b][1,4]oxazin-7-yl)sulfonyl)benzamide, 4-(2-((S)-2-(2-cyclobutylphenyl)pyrrolidin-1-yl)-7-azaspiro[3.5]nonan-7-yl)-2-(3,3-dimethyl-2,3-dihydropyrrolo[3',2':5,6]pyrido[2,3-b][1,4]oxazin-1(6H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 4-(2-((S)-2-(2-ethylphenyl)pyrrolidin-1-yl)-7-azaspiro[3.5]nonan-7-yl)-N-(((R)-3-((1s,4S)-4-hydroxycyclohexyl)-5-nitro-3,4-dihydro-2H-benzo[b][1,4]oxazin-7-yl)sulfonyl)-2-(2'H-spiro[cyclopropane-1,3'-pyrrolo[3',2':5,6]pyrido[2,3-b][1,4]oxazin]-1'(6'H)-yl)benzamide, N-(((R)-3-((1r,4R)-4-hydroxycyclohexyl)-5-nitro-3,4-dihydro-2H-benzo[b][1,4]oxazin-7-yl)sulfonyl)-2-((R)-3-isopropyl-2,3-dihydropyrrolo[3',2':5,6]pyrido[2,3-b][1,4]oxazin-1(6H)-yl)-4-(2-((S)-2-(2-(trifluoromethyl)phenyl)pyrrolidin-1-yl)-7-azaspiro[3.5]nonan-7-yl)benzamide, 2-((R)-3-(tert-butyl)-2,3-dihydropyrrolo[3',2':5,6]pyrido[2,3-b][1,4]oxazin-1(6H)-yl)-4-(2-((S)-2-(2-ethynylphenyl)pyrrolidin-1-yl)-7-azaspiro[3.5]nonan-7-yl)-N-(((S)-3-((1s,4R)-4-hydroxycyclohexyl)-5-nitro-3,4-dihydro-2H-benzo[b][1,4]oxazin-7-yl)sulfonyl)benzamide, 2-((S)-3-(tert-butyl)-2,3-dihydropyrrolo[3',2':5,6]pyrido[2,3-b][1,4]oxazin-1(6H)-yl)-4-(2-((S)-2-(2-(tert-butyl)phenyl)pyrrolidin-1-yl)-7-azaspiro[3.5]nonan-7-yl)-N-(((S)-3-((1r,4S)-4-hydroxycyclohexyl)-5-nitro-3,4-dihydro-2H-benzo[b][1,4]oxazin-7-yl)sulfonyl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-(1,1,1-trifluoro-2-methylpropan-2-yl)phenyl)pyrrolidin-1-yl)-7-azaspiro[3.5]nonan-7-yl)-2-((S)-3-(trifluoromethyl)-2,3-dihydropyrrolo[3',2':5,6]pyrido[2,3-b][1,4]oxazin-1(6H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)-4,4-dimethylpyrrolidin-1-yl)-

7-azaspiro[3.5]nonan-7-yl)-2-((R)-3-(trifluoromethyl)-2,3-dihydropyrrolo[3',2':5,6]pyrido[2,3-b][1,4]oxazin-1(6H)-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-6-(2-isopropylphenyl)-5-azaspiro[2.4]heptan-5-yl)-7-azaspiro[3.5]nonan-7-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((R)-2-(2-isopropylphenyl)piperidin-1-yl)-7-azaspiro[3.5]nonan-7-yl)-2-((S)-4-methyl-3,4-dihydro-2H-pyrrolo[3',2':5,6]pyrido[2,3-b][1,4]oxazepin-1(7H)-yl)benzamide, 4-(2-((S)-3-(2-isopropylphenyl)morpholino)-7-azaspiro[3.5]nonan-7-yl)-2-((S)-3-methyl-3,4-dihydro-2H-pyrrolo[3',2':5,6]pyrido[2,3-b][1,4]oxazepin-1(7H)-yl)-N-(((R)-3-(morpholinomethyl)-5-nitro-3,4-dihydro-2H-benzo[b][1,4]oxazin-7-yl)sulfonyl)benzamide, 4-(2-(5-(2-isopropylphenyl)-1,4-oxazepan-4-yl)-7-azaspiro[3.5]nonan-7-yl)-2-((R)-2-methyl-3,4-dihydro-2H-pyrrolo[3',2':5,6]pyrido[2,3-b][1,4]oxazepin-1(7H)-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-(4-isopropyl-7-(2-isopropylphenyl)-1,4-diazepan-1-yl)-7-azaspiro[3.5]nonan-7-yl)-2-((R)-4-methyl-3,4-dihydro-2H-pyrrolo[3',2':5,6]pyrido[2,3-b][1,4]oxazepin-1(7H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-(4-isopropyl-7-(2-isopropylphenyl)-1,4-diazepan-1-yl)-7-azaspiro[3.5]nonan-7-yl)-2-((R)-3-methyl-3,4-dihydro-2H-pyrrolo[3',2':5,6]pyrido[2,3-b][1,4]oxazepin-1(7H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)-2-((S)-2-methyl-3,4-dihydro-2H-pyrrolo[3',2':5,6]pyrido[2,3-b][1,4]oxazepin-1(7H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((R)-4-isopropyl-3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, 4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)-2-((R)-4-(trifluoromethyl)-3,4-dihydro-2H-pyrrolo[3',2':5,6]pyrido[2,3-b][1,4]oxazepin-1(7H)-yl)benzamide, 2-((R)-4-(tert-butyl)-3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)benzamide, 2-((S)-4-isopropyl-3,4-dihydro-2H-pyrrolo[3',2':5,6]pyrido[2,3-b][1,4]oxazepin-1(7H)-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)-2-((S)-4-(trifluoromethyl)-3,4-dihydro-2H-pyrrolo[3',2':5,6]pyrido[2,3-b][1,4]oxazepin-1(7H)-yl)benzamide, 2-((S)-4-(tert-butyl)-3,4-dihydro-2H-pyrrolo[3',2':5,6]pyrido[2,3-b][1,4]oxazepin-1(7H)-yl)-N-(((S)-3-(isopropoxymethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((S)-5-nitro-3-(pyridin-2-ylmethyl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)-2-((R)-4-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-5-nitro-3-(tetrahydro-2H-pyran-4-yl)-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-5-nitro-3-(tetrahydro-2H-pyran-4-yl)-3,4-dihydro-2H-benzo[b][1,4]oxazin-7-yl)sulfonyl)benzamide, N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-((1r,4S)-4-hydroxycyclohexyl)-5-nitro-3,4-dihydro-2H-benzo[b][1,4]oxazin-7-yl)sulfonyl)-4-(2-((S)-

2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-3-(morpholinomethyl)-5-nitro-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-3-((4-methylpiperazin-1-yl)methyl)-5-nitro-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-3-((4-methylpiperazin-1-yl)methyl)-5-nitro-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide, 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-5-nitro-3-(pyridin-2-ylmethyl)-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide, N-(((S)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxycyclohexyl)-5-nitro-3,4-dihydro-2H-benzo[b][1,4]oxazin-7-yl)

sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, 2-(3,4-dihydro-2H-pyrrolo[3',2':5,6]pyrido[2,3-b][1,4]oxazepin-1(7H)-yl)-N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)benzamide, 2-((R)-3-methyl-2,3-dihydropyrrolo[3',2':5,6]pyrido[2,3-b][1,4]oxazin-1(6H)-yl)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((R)-3-((1s,4S)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5]nonan-7-yl)benzamide, N-(((R)-3-((1r,4R)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]

oxazin-1(6H)-yl)-4-(2-((S)-2-(2-(prop-1-en-2-yl)phenyl) pyrrolidin-1-yl)-7-azaspiro[3.5]nonan-7-yl)benzamide, N-(((S)-3-((1s,4R)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4] oxazin-1(6H)-yl)-4-(2-((S)-2-(2-(prop-1-en-2-yl)phenyl) pyrrolidin-1-yl)-7-azaspiro[3.5]nonan-7-yl)benzamide, N-(((S)-3-((1r,4S)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4] oxazin-1(6H)-yl)-4-(2-((S)-2-(2-(prop-1-en-2-yl)phenyl) pyrrolidin-1-yl)-7-azaspiro[3.5]nonan-7-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b] [1,4]oxazin-1(6H)-yl)-4-(2-((S)-2-(2-(prop-1-en-2-yl) phenyl)pyrrolidin-1-yl)-7-azaspiro[3.5]nonan-7-yl) benzamide, N-(((R)-3-((1s,4S)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b] [1,4]oxazin-1(6H)-yl)-4-(2-((S)-2-(2-(prop-1-en-2-yl) phenyl)pyrrolidin-1-yl)-7-azaspiro[3.5]nonan-7-yl) benzamide, N-(((S)-3-((1r,4S)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b] [1,4]oxazin-1(6H)-yl)-4-(2-((S)-2-(2-(prop-1-en-2-yl) phenyl)pyrrolidin-1-yl)-7-azaspiro[3.5]nonan-7-yl) benzamide, N-(((S)-3-((1s,4R)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b] [1,4]oxazin-1(6H)-yl)-4-(2-((S)-2-(2-(prop-1-en-2-yl) phenyl)pyrrolidin-1-yl)-7-azaspiro[3.5]nonan-7-yl) benzamide, 2-((R)-3-methyl-2,3-dihydropyrrolo[3',2':5,6]pyrido[2,3-b] [1,4]oxazin-1(6H)-yl)-N-(((R)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b] [1,4]oxazin-1(6H)-yl)-N-(((S)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl) methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5] nonan-7-yl)benzamide, N-(((S)-3-(((1S,4S)-2-oxa-5-azabicyclo[2.2.1]heptan-5-yl) methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5] nonan-7-yl)benzamide, N-(((R)-3-(((1R,4R)-2-oxa-5-azabicyclo[2.2.1]heptan-5-yl) methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5] nonan-7-yl)benzamide, N-(((S)-3-(((1R,4R)-2-oxa-5-azabicyclo[2.2.1]heptan-5-yl) methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5] nonan-7-yl)benzamide, 2-((R)-3-methyl-2,3-dihydropyrrolo[3',2':5,6]pyrido[2,3-b] [1,4]oxazin-1(6H)-yl)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl) pyrrolidin-1-yl)-7-azaspiro[3.5]nonan-7-yl)benzamide, 2-((R)-3-methyl-2,3-dihydropyrrolo[3',2':5,6]pyrido[2,3-b] [1,4]oxazin-1(6H)-yl)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl) pyrrolidin-1-yl)-7-azaspiro[3.5]nonan-7-yl)benzamide, 2-((R)-3-methyl-2,3-dihydropyrrolo[3',2':5,6]pyrido[2,3-b] [1,4]oxazin-1(6H)-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5] nonan-7-yl)benzamide, N-(((S)-3-(isopropoxymethyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b] [1,4]oxazin-1(6H)-yl)-N-(((S)-5-nitro-3-(pyridin-2-ylmethyl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4] oxazepin-1(7H)-yl)-N-(((R)-5-nitro-3-(tetrahydro-2H-pyran-4-yl)-3,4-dihydro-2H-benzo[b][1,4]oxazin-7-yl) sulfonyl)-4-(2-((S)-2-(2-(prop-1-en-2-yl)phenyl) pyrrolidin-1-yl)-7-azaspiro[3.5]nonan-7-yl)benzamide, 2-(3,4-dihydro-2H-pyrrolo[3',2':5,6]pyrido[2,3-b][1,4] oxazepin-1(7H)-yl)-N-(((S)-5-nitro-3-(tetrahydro-2H-pyran-4-yl)-3,4-dihydro-2H-benzo[b][1,4]oxazin-7-yl) sulfonyl)-4-(2-((S)-2-(2-(prop-1-en-2-yl)phenyl) pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4] oxazepin-1(7H)-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4] oxazepin-1(7H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4] oxazepin-1(7H)-yl)-N-(((R)-3-((1s,4S)-4-hydroxycyclohexyl)-5-nitro-3,4-dihydro-2H-benzo[b][1,4]oxazin-7-yl) sulfonyl)-4-(2-((S)-2-(2-(prop-1-en-2-yl)phenyl) pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(isopropoxymethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-5-nitro-3-(pyridin-2-ylmethyl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((R)-3-((1s,4S)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((R)-3-((1r,4R)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-((1s,4R)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-((1r,4S)-4-hydroxycyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((R)-3-((1r,4R)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((R)-3-((1s,4S)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-((1r,4S)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-((1s,4R)-4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((S)-3-(isopropoxymethyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)-4-(2-((S)-2-(o-tolyl)pyrrolidin-1-yl)-7-azaspiro[3.5]nonan-7-yl)benzamide, 2-((R)-3-methyl-2,3-dihydropyrrolo[3',2':5,6]pyrido[2,3-b][1,4]oxazin-1(6H)-yl)-N-(((S)-5-nitro-3-(pyridin-2-ylmethyl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-3-(isopropoxymethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-(3,4-dihydro-2H-pyrrolo[3',2':5,6]pyrido[2,3-b][1,4]oxazepin-1(7H)-yl)-N-(((S)-5-nitro-3-(pyridin-2-ylmethyl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, Part 5

2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((3-((4-methylpiperazin-1-yl)methyl)-5-nitro-3,4-dihydro-2H-benzo[b][1,4]oxazin-7-yl)sulfonyl)benzamide, N-(((S)-3-((R)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)benzamide, 2-((1H-pyrrolo[2,3-b]pyridin-5-yl)oxy)-4-(2-(2-(2-cyclopropylphenyl)pyrrolidin-1-yl)-7-azaspiro[3.5]nonan-7-yl)-N-((5-nitro-3-(tetrahydro-2H-pyran-4-yl)-3,4-dihydro-2H-benzo[b][1,4]oxazin-7-yl)sulfonyl)benzamide, 2-(1-(1H-pyrrolo[2,3-b]pyridin-5-yl)ethyl)-4-(2-(2-(2-cyclopropylphenyl)pyrrolidin-1-yl)-7-azaspiro[3.5]nonan-7-yl)-N-((3-(morpholinomethyl)-5-nitro-3,4-dihydro-2H-benzo[b][1,4]oxazin-7-yl)sulfonyl)benzamide, 4-(2-(2-(2-cyclopropylphenyl)pyrrolidin-1-yl)-7-azaspiro[3.5]nonan-7-yl)-2-(dimethyl(1H-pyrrolo[2,3-b]pyridin-5-yl)silyl)-N-((3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)benzamide, 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(2-(prop-1-en-2-yl)phenyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-(morpholinomethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((S)-5-nitro-3-(pyridin-2-ylmethyl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(o-tolyl)pyrrolidin-1-yl)-7-azaspiro[3.5]nonan-7-yl)benzamide, N-(((R)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-(morpholinomethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-((4-methylpiperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-N-(((S)-5-nitro-3-(pyridin-2-ylmethyl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, 2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)-N-(((R)-5-nitro-3-(tetrahydro-2H-pyran-4-yl)-3,4-dihydro-2H-benzo[b][1,4]oxazin-7-yl)sulfonyl)benzamide, 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(6-((S)-2-(2-(prop-1-en-2-yl)phenyl)pyrrolidin-1-yl)-2-azaspiro[3.3]heptan-2-yl)benzamide, 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(6-((S)-2-(o-tolyl)pyrrolidin-1-yl)-2-azaspiro[3.3]heptan-2-yl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(6-((S)-2-(2-(prop-1-en-2-yl)phenyl)pyrrolidin-1-yl)-2-azaspiro[3.3]heptan-2-yl)benzamide, N-(((S)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(6-((S)-2-(o-tolyl)pyrrolidin-1-yl)-2-azaspiro[3.3]heptan-2-yl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(6-((S)-2-(2-(prop-1-en-2-yl)phenyl)pyrrolidin-1-yl)-2-azaspiro[3.3]heptan-2-yl)benzamide, 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(6-((S)-2-(o-tolyl)pyrrolidin-1-yl)-2-azaspiro[3.3]heptan-2-yl)benzamide, 2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)-N-(((S)-5-nitro-3-(pyridin-2-ylmethyl)-3,4-dihydro-2H-benzo[b][1,4]oxazin-7-yl)sulfonyl)benzamide, 2-((1H-pyrrolo[2,3-b]pyridin-5-yl)oxy)-N-(((S)-5-nitro-3-(pyridin-2-ylmethyl)-3,4-dihydro-2H-benzo[b][1,4]oxazin-7-yl)sulfonyl)-4-(6-((S)-2-(2-(prop-1-en-2-yl)phenyl)pyrrolidin-1-yl)-2-azaspiro[3.3]heptan-2-yl)benzamide, 2-((1H-pyrrolo[2,3-b]pyridin-5-yl)oxy)-N-(((S)-5-nitro-3-(pyridin-2-ylmethyl)-3,4-dihydro-2H-benzo[b][1,4]oxazin-7-yl)sulfonyl)-4-(6-((S)-2-(o-tolyl)pyrrolidin-1-yl)-2-azaspiro[3.3]heptan-2-yl)benzamide, 2-((1H-pyrrolo[2,3-b]pyridin-5-yl)oxy)-N-(((R)-3-((1r,4R)-4-hydroxy-4-methylcyclohexyl)-5-nitro-3,4-dihydro-2H-benzo[b][1,4]oxazin-7-yl)sulfonyl)-4-(6-((S)-2-(o-tolyl)pyrrolidin-1-yl)-2-azaspiro[3.3]heptan-2-yl)benzamide, 2-((1H-pyrrolo[2,3-b]pyridin-5-yl)oxy)-N-(((R)-3-((1s,4S)-4-hydroxy-4-methylcyclohexyl)-5-nitro-3,4-dihydro-2H-benzo[b][1,4]oxazin-7-yl)sulfonyl)-4-(6-((S)-2-(2-isopropylphenyl)pyrrolidin-1-yl)-2-azaspiro[3.3]heptan-2-yl)benzamide, 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(6-((S)-2-(2-(prop-1-en-2-yl)phenyl)pyrrolidin-1-yl)-2-azaspiro[3.3]heptan-2-yl)benzamide, 2-((1H-pyrrolo[2,3-b]pyridin-5-yl)oxy)-4-(6-((S)-2-(2-cyclopropylphenyl)pyrrolidin-1-yl)-2-azaspiro[3.3]heptan-2-yl)-N-(((S)-3-((1s,4R)-4-hydroxy-4-methylcyclohexyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-vinylphenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-(trifluoromethyl)phenyl)pyrrolidin-1-yl)-7-azaspiro[3.5]nonan-7-yl)benzamide, 2-((1H-pyrrolo[2,3-b]pyridin-5-yl)oxy)-4-(2-((S)-2-(2-ethynylphenyl)pyrrolidin-1-yl)-7-azaspiro[3.5]nonan-7-yl)-N-(((S)-3-((1s,4R)-4-hydroxycyclohexyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-((S)-2-(2-(tert-butyl)phenyl)pyrrolidin-1-yl)-7-azaspiro[3.5]nonan-7-yl)-N-(((S)-3-((1r,4S)-4-hydroxycyclohexyl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-(1,1,1-trifluoro-2-methylpropan-2-yl)phenyl)pyrrolidin-1-yl)-7-azaspiro[3.5]nonan-7-yl)benzamide, 2-((1H-pyrrolo[2,3-b]pyridin-5-yl)oxy)-N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)-4,4-dimethylpyrrolidin-1-yl)-7-azaspiro[3.5]nonan-7-yl)benzamide, 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-6-(2-isopropylphenyl)-5-azaspiro[2.4]heptan-5-yl)-7-azaspiro[3.5]nonan-7-yl)benzamide, 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((R)-2-(2-isopropylphenyl)piperidin-1-yl)-7-azaspiro[3.5]nonan-7-yl)benzamide, 2-((1H-pyrrolo[2,3-b]pyridin-5-yl)oxy)-4-(2-((S)-3-(2-isopropylphenyl)morpholino)-7-azaspiro[3.5]nonan-7-yl)-N-(((R)-3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-4-(2-(5-(2-isopropylphenyl)-1,4-oxazepan-4-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-(7-(2-isopropylphenyl)-4-methyl-1,4-diazepan-1-yl)-7-azaspiro[3.5]nonan-7-yl)benzamide, 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-(4-isopropyl-7-(2-isopropylphenyl)-1,4-diazepan-1-yl)-7-azaspiro[3.5]nonan-7-yl)benzamide, Compounds of the invention may contain one or more asymmetric carbon atoms. Accordingly, the compounds may exist as diastereomers, enantiomers or mixtures thereof.

The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration, and both of these configurations are within the scope of the invention.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term “geometric isomer” refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent.

Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery,* 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^X$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. The invention encompasses any pharmaceutically acceptable salts and solvates of any one of the above-described compounds and modifications thereof. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The compounds disclosed therein are bcl-2 inhibitors. The pharmaceutical composition of the present invention comprises one or more bcl-2 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes.

Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

The pharmaceutical compositions of the present invention may further comprise other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions of the present invention may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$, $C_1$-$C_6$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$, $C_2$-$C_6$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$, $C_2$-$C_6$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a saturated or unsaturated nonaromatic 5-8 membered monocyclic, 8-12 membered bicyclic, or 11-14 membered tricyclic ring system having 1 to 4 heteroatoms (such as O, N, S, B, P, Si, or Se), which may be the same or different. Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, B, Si, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O═), thioxo (S═), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)$NR_aR_b$ where $R_a$ and $R_b$ are each independently two further substituents where a hydrogen or carbon atom is alpha to the nitrogen. It is noted that carbamoyl moieties may include protected derivatives thereof.

Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O-. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH═O.

"Formimino" means the radical —HC═NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(═NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —$NO_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)-. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), antimicrotubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK (A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CSF1R, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRKIA, DYRKIB, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKGla, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEEl, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1($Q_{252}$H), ABL1(T315I), ABL1(Y253F), ALK ($C_{1156}$Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDG-FRa(D842V), PDGFRa(T674I), PDGFRa(V561D), RET (E762Q), RET(G691S), RET(M918T), RET(R749T), RET (R813Q), RET(V804L), RET(V804M), RET(Y79IF), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g.HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc), and other immunotherapies (e.g anti-PD1, anti-PDL1, anti-CTLA4, CAR-T, IDO, A2A antagonist etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, pembrolizumab, nivolumab, atezolizumab, durvalumab, avelumab, as tisagenlecleucel, axicabtagene ciloleucel, radiation therapy, or surgery.

The invention further provides methods for the prevention or treatment of a neoplastic disease or autoimmune disease. In one embodiment, the invention relates to a method of treating a neoplastic disease or autoimmune disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or autoimmune disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

The autoimmune diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barré syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of the intermediate

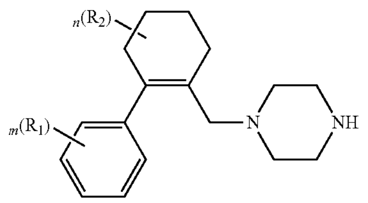

is described in Scheme 1-1 below: $R_1$, $R_2$, m, and n, in general Scheme 1-1 are the same as those described in the Summary section above.

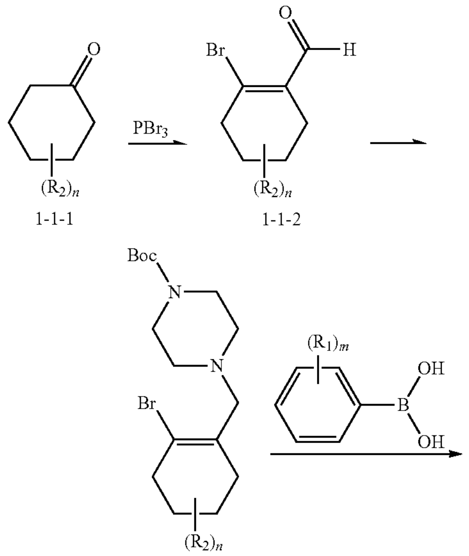

1-1-1 1-1-2

1-1-3

-continued

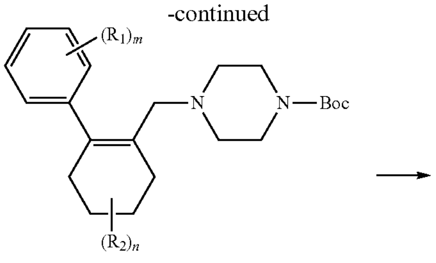

1-1-4

1-1-5

In Scheme 1-1, the appropriate ketone starting material 1-1-1 can react with tribromophosphine to form the aldehyde intermediate 1-1-2, which can couple with Boc-protected piperazine to form the intermediate 1-1-3. After that, 1-1-3 will couple with appropriate phenylboronic acid via a Suzuki reaction to form intermediate 1-1-4, followed by a de-boc process to yield key intermediate 1-1-5.

The intermediate of

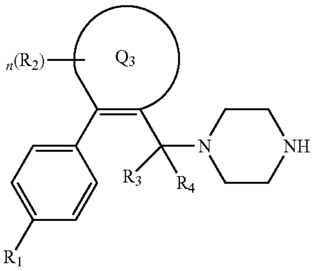

can be prepared by the method similar to the Scheme 1-1, and those described in US9,018,381 by using appropriate staring materials and intermediates.

The intermediate of

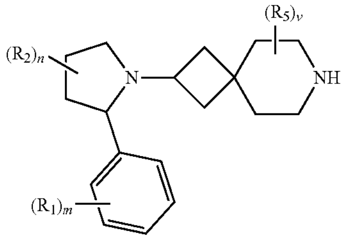

can be prepared by the method similar to those described in WO2019210828 by using appropriate staring materials and intermediates.

The intermediate of

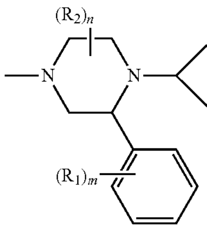

can be prepared by the method similar to those described in WO2019210828 by using appropriate staring materials and intermediates.

The intermediate of

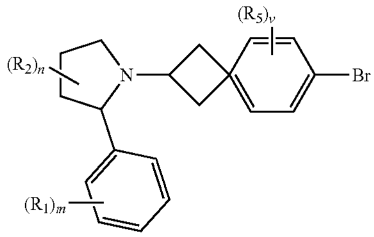

can be prepared by the method similar to those described in WO2019210828 by using appropriate staring materials and intermediates.

A typical approach to synthesize of the intermediate

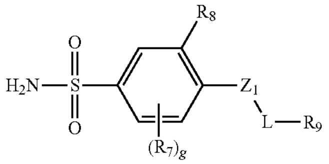

in which $R_8$ is $NO_2$ is described in Scheme 2-1 below. $R_7$, $R_8$, L, and $R_9$, in general Scheme 2-1 are the same as those described in the Summary section above.

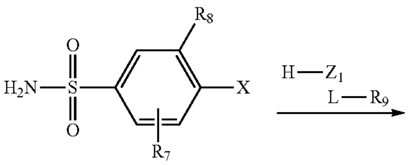

2-1-1

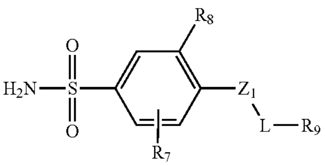

2-1-2

In Scheme 2-1, the starting material 2-1-1 reacts with appropriate alcohol or amine will yield 2-1-2.

A typical approach to synthesize of the intermediate

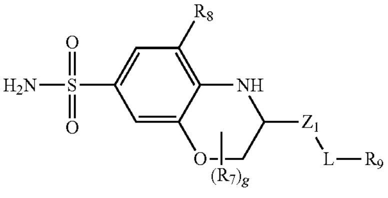

in which $R_8$ is $NO_2$ is described in Scheme 2-2 below. $R_8$, $Z_1$, L, and $R_9$, in general Scheme 2-2 are the same as those described in the Summary section above.

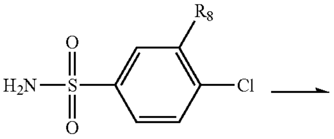

2-2-1

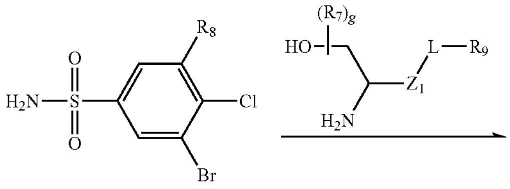

2-2-2

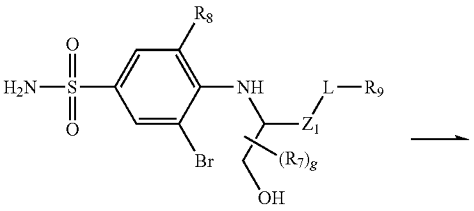

2-2-3

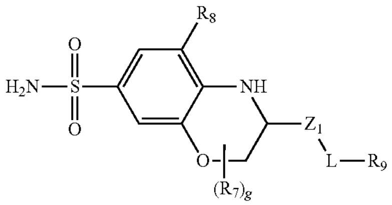

2-2-4

In Scheme 2-2, the bromination of the commercially available 2-2-1 results in 2-2-2, and then the reaction of 2-2-2 with appropriate amine provides 2-2-3. Intramolecular cycliation of 2-2-3 using metal catalyzed coupling condition such as Buchwald reaction or other coupling reaction known in the literature give 2-2-4. Alternatively, 2-2-4 can be obtained via a 3 step sequence of mesylation of the hydroxyl group of 2-2-3, SN2 reaction and intramolecular cyclization.

Similarly, the intermediate of

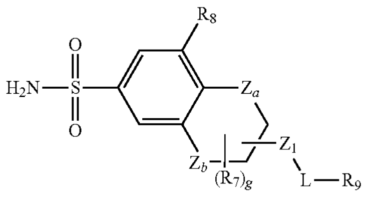

with different $Z_a$ and $Z_b$ can be prepared by the method similar to the Scheme 2-2 by using appropriate staring materials, intermediates, and intramolecular cylization.

Similarly, the intermediate of

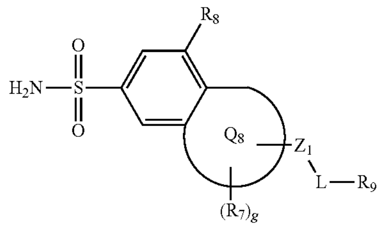

with different $Q_8$ can be prepared by the method similar to the Scheme 2-2 by using appropriate staring materials, intermediates, and intramolecular cylization.

Similarly, the intermediate of

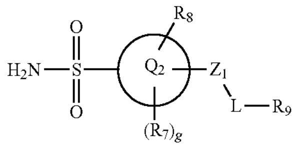

with different $R_7$ and $Q_7$ can be prepared by the method similar to the Scheme 2-1 and 2-2 by using appropriate staring materials, intermediates, and intramolecular cylization.

The intermediate of

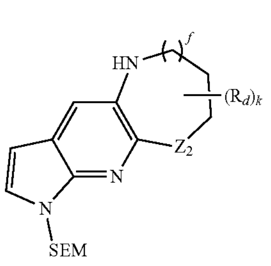

and

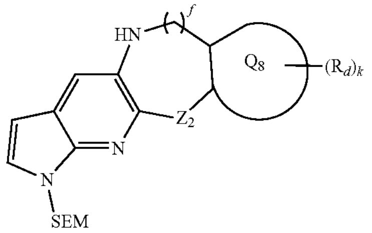

SEM and SEM can be prepared by the method similar to those described in WO/2017/132474, WO/2019/040573, WO/2019/040550, WO2020041405, WO2020041406, PCT/US2020/020010, WO/2020/140005 by using appropriate staring materials and intermediates.

A typical approach to synthesize of the intermediate

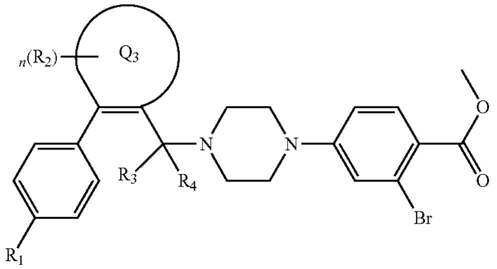

is described in Scheme 3-1 below. $R_2$, and n, in general Scheme 3-1 are the same as those described in the Summary section above.

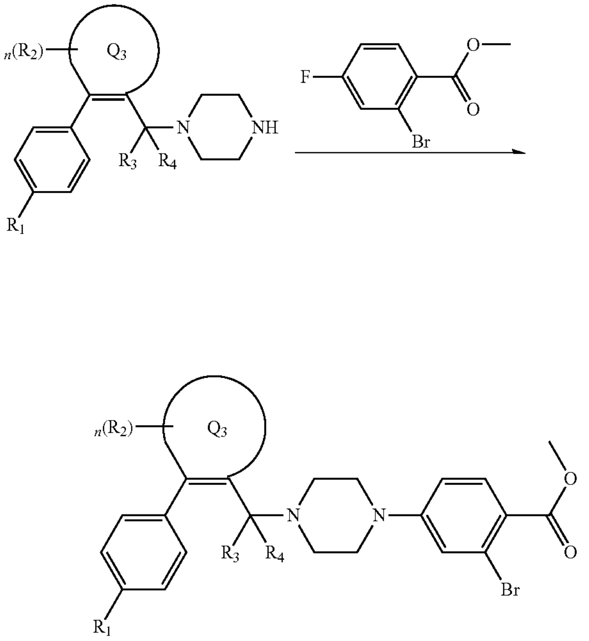

3-1-2

In Scheme 3-1, the starting material undergoes nucleophilic aromatic substitution with selected p-fluoro-2-bromobenzoate to give 3-1-2.

An improved approach to synthesize of target compounds in which Z is —P(O)$CH_3$-shown in the scheme below is described in Scheme A-1:

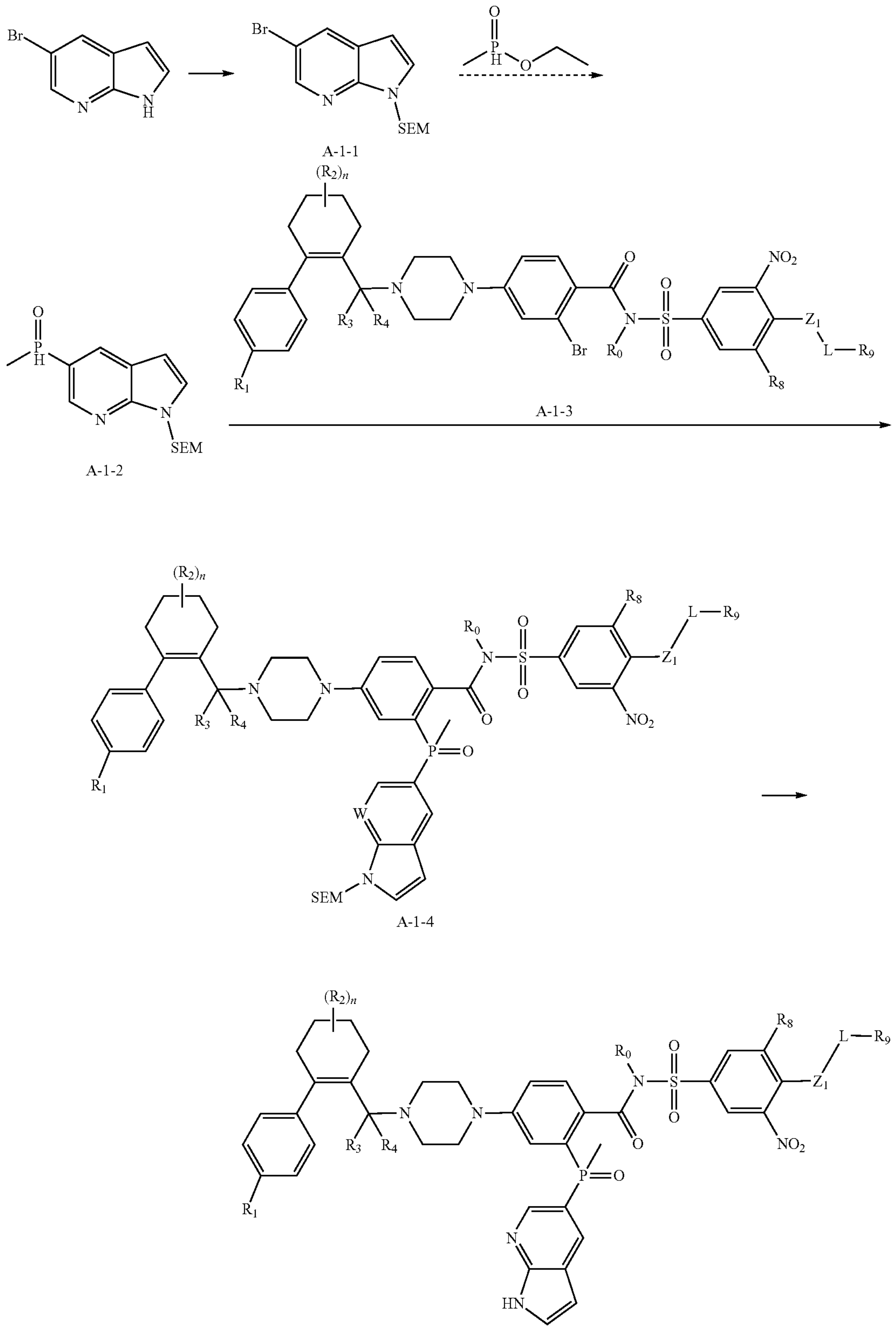

In Scheme A-1, the commercially available staring material 5-bromo-1H-pyrrolo[2,3-b]pyridine can react with SEM-Cl to form the SEM-protected intermediate A-1-1, which can react with ethyl methylphosphinate to afford the intermediate A-1-2. After that, A-1-2 can react with appropriate intermediate A-1-3 to form the intermediate A-1-4, which can undergo a de-protection of SEM group to affods target compounds.

Similarly, the compounds of

Formula (II)

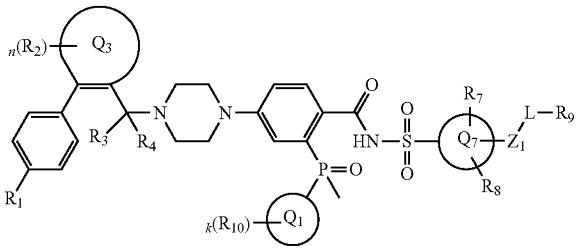

can be prepared by the method similar to above Schemes by using appropriate staring materials and intermediates.

Similarly, the compounds of

Formula (I)

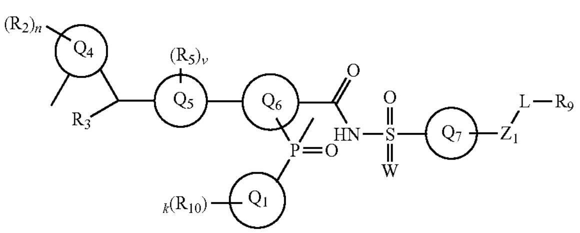

can be prepared by the method similar to above the Schemes by using appropriate staring materials and intermediates.

An improved approach to synthesize of target compounds of

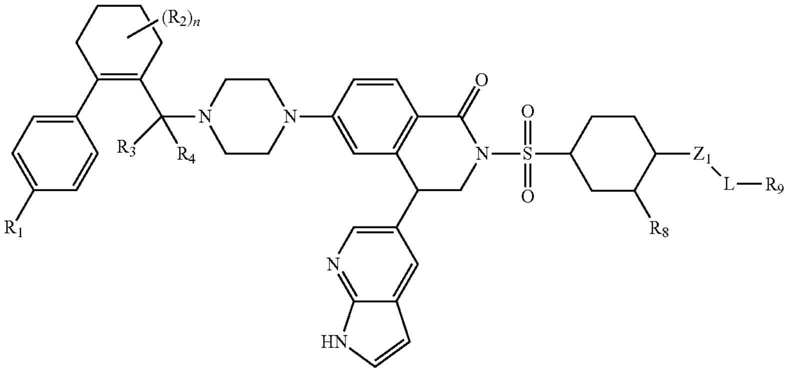

is described in Scheme A-2:

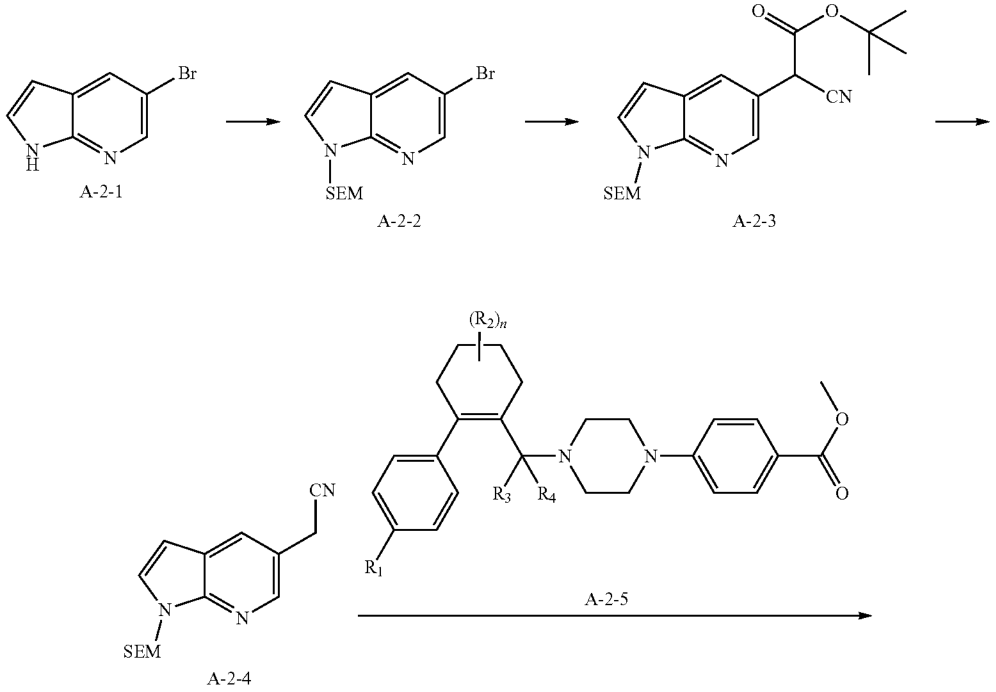

A-2-1

A-2-2

A-2-3

A-2-5

A-2-4

-continued
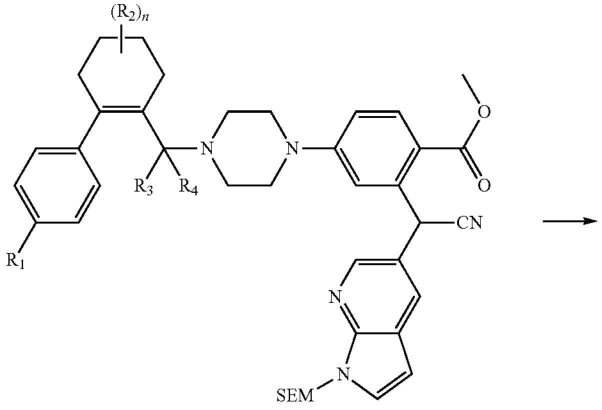
A-2-6
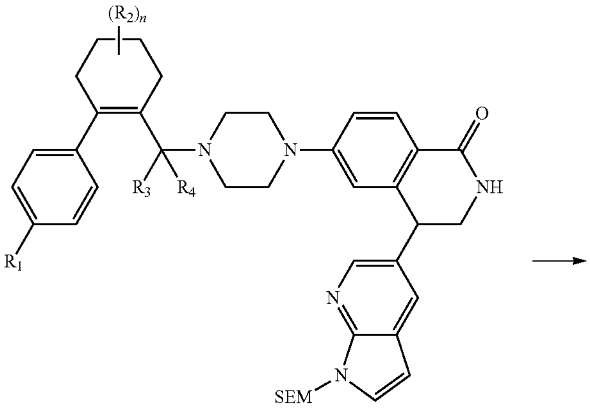
A-2-7
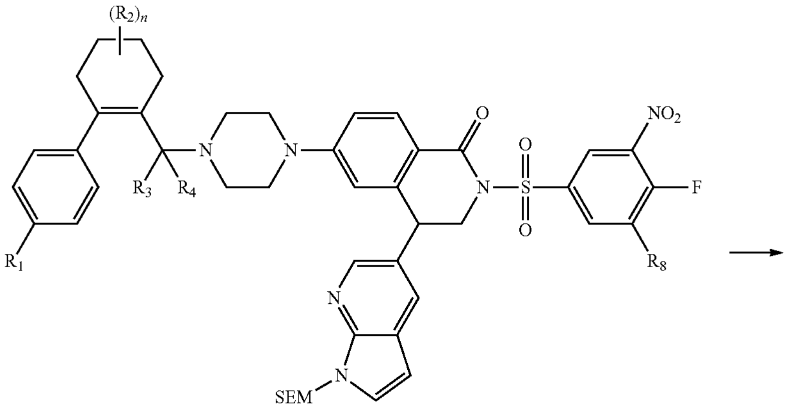
A-2-8

-continued

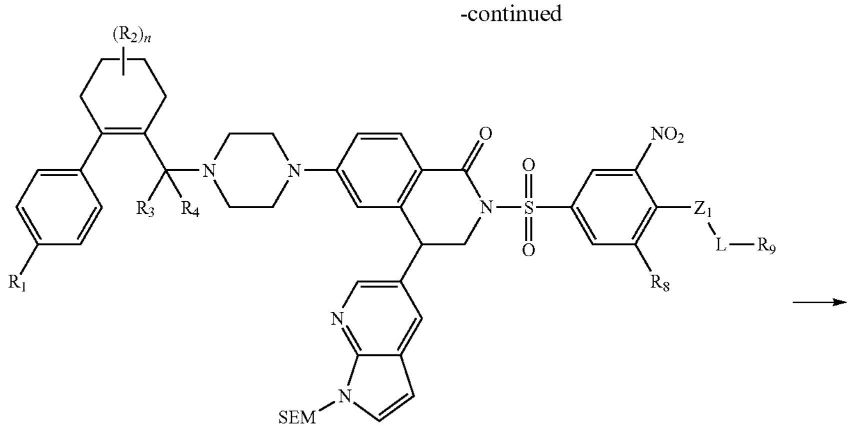

A-2-9

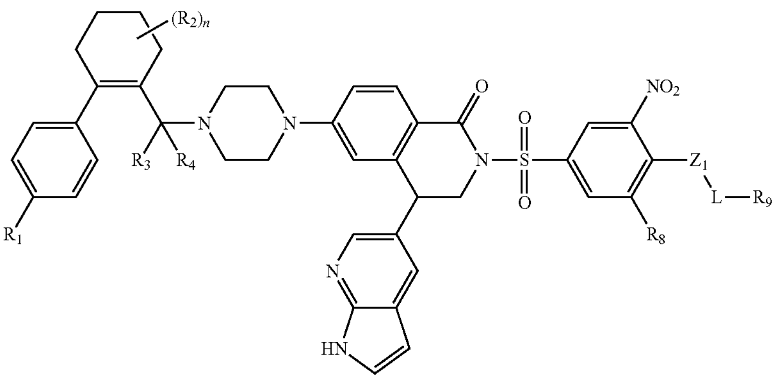

In Scheme A-2, the commercially available staring material 5-bromo-1H-pyrrolo[2,3-b]pyridine can react with SEM-Cl to form the SEM-protected intermediate A-2-2, which can react with tert-butyl 2-cyanoacetate to form the intermediate A-2-3. Heating of A-2-3 in DMSO for a few hour can lead to the intermediate A-2-4 which can react with A-2-5 to the intermediate A-2-6. After that, A-2-6 can undergo a reduction and ring closure reaction to form the intermediate A-2-7, which can reaction with substituted 4-fluoro-3-nitrobenzenesulfonyl chloride to yield the intermediate A-2-8. Finally, A-2-8 can react with appropriate side chain to afford the A-2-9, which can undergo a de-protection of SEM group in acid condistion to affods target compounds.

An approach to synthesize of target compounds of

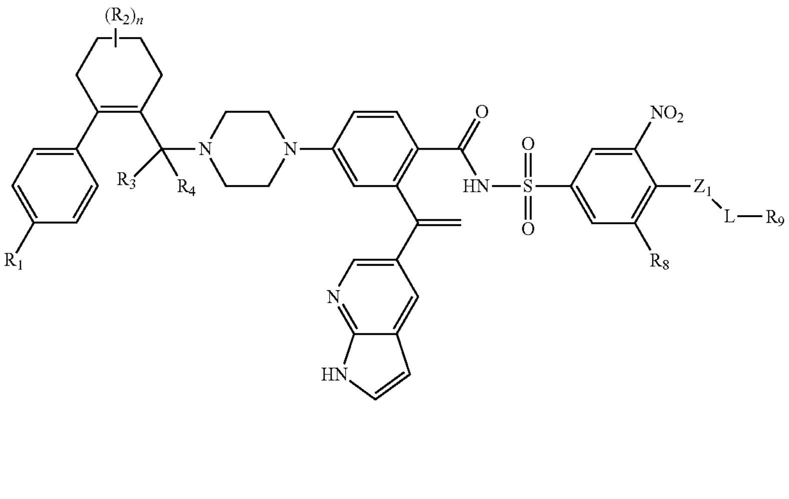

is described in Scheme A-3:
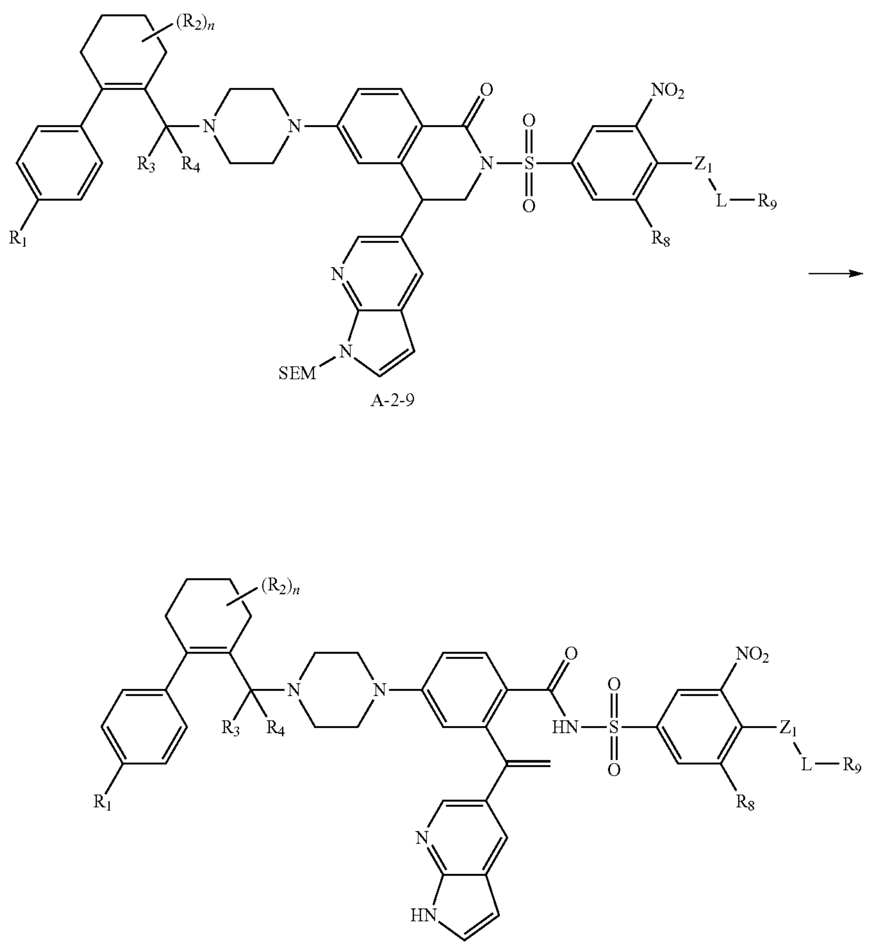
A-2-9
In Scheme A-3, the intermediate A-2-9 from Scheme A-2 can undergo a de-protection of SEM group under basic condition to affods ring-opened target compounds.
An approach to synthesize of target compounds of Formula (III) is described in Scheme A-6:
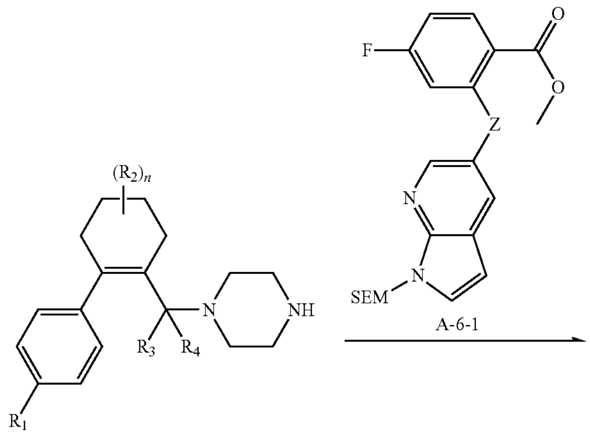
A-6-1
A-6-0

-continued
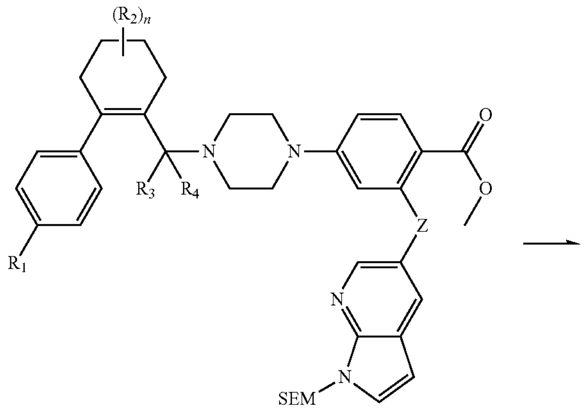
A-6-2
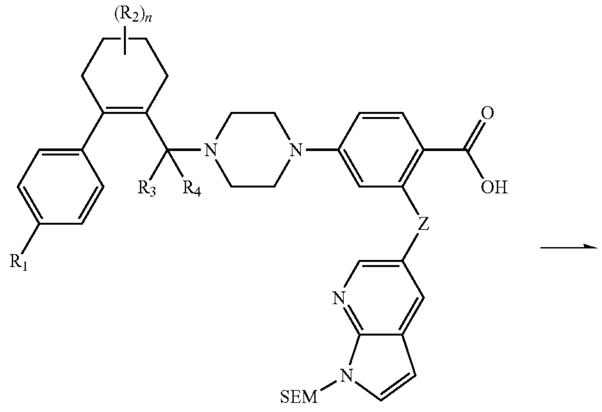
A-6-3
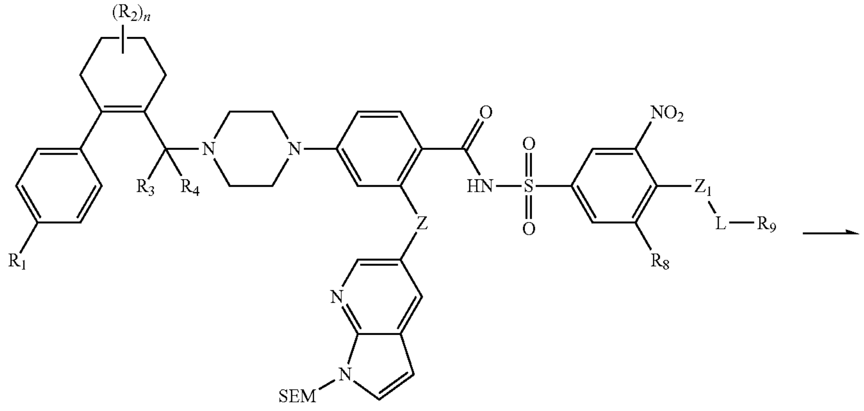
A-6-4

-continued
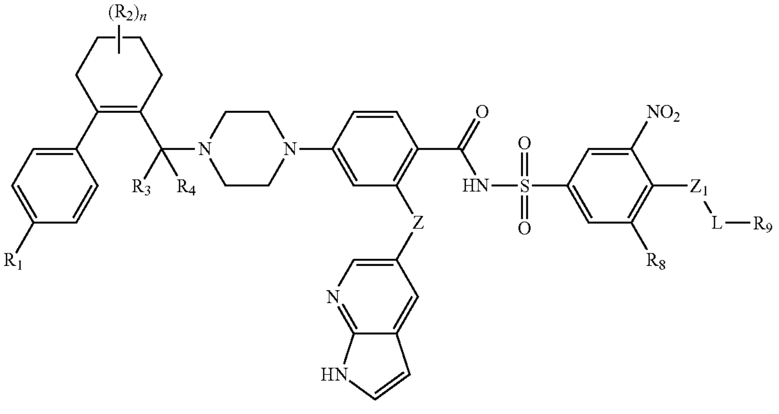
Formula (III)
In Scheme A-6, the intermediate A-6-0 can reaction with A-6-1 to form the intermediate A-6-2. The hydrolysis of A-6-2 in basic condition will lead to A-6-3, which can react with appropriate side chain followed by deprotection of SEM group to afford the target compounds.
An approach to synthesize of target compounds of
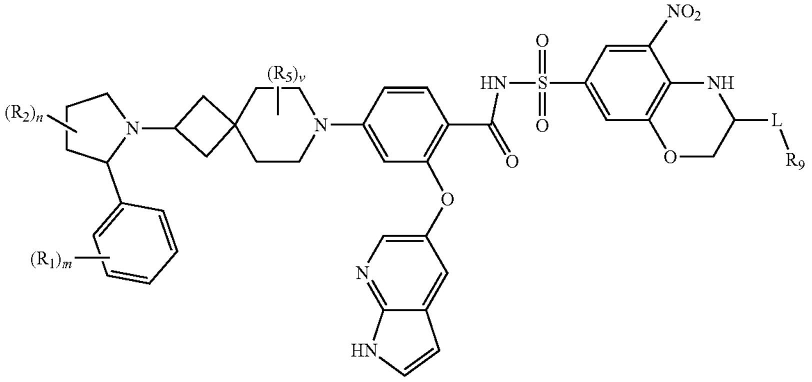
is described in Scheme A-4:
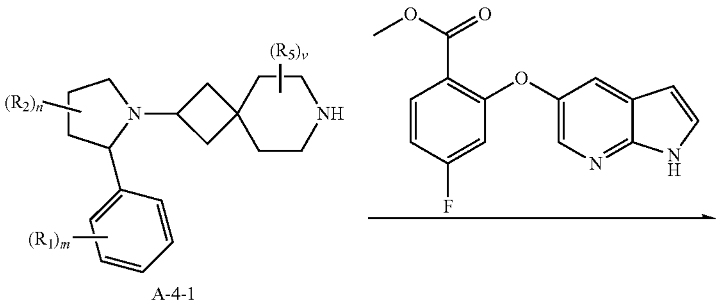
A-4-1

-continued
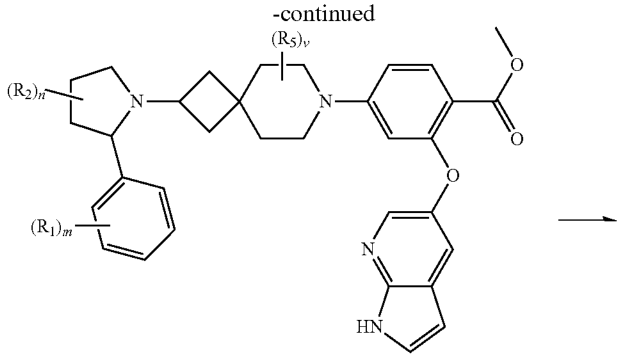
A-4-2
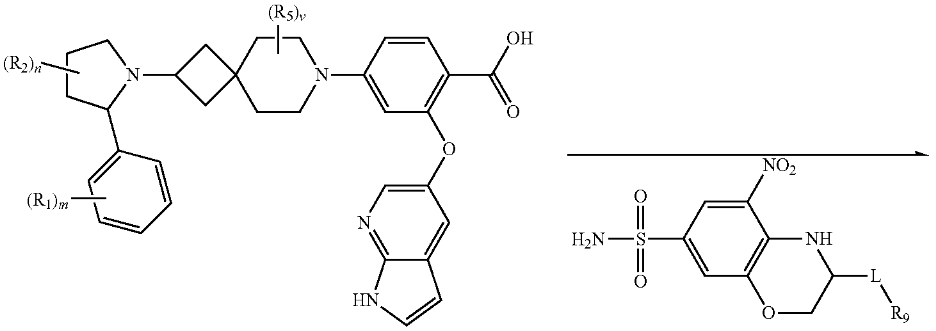
A-4-3
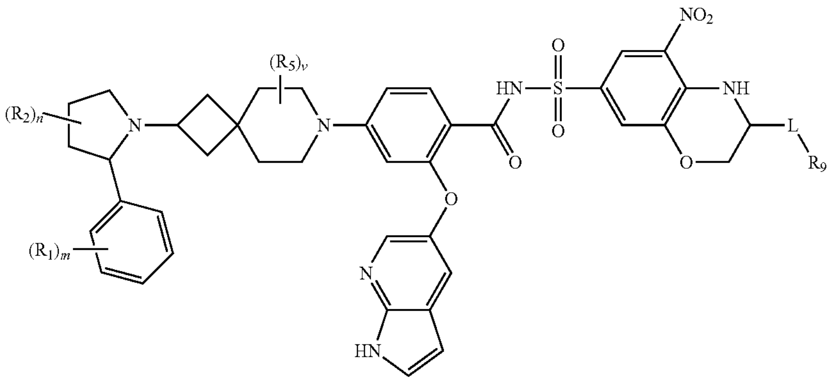
In Scheme A-4, the intermediate A-4-1 can react with the commercially available intermediate methyl 2-((1H-pyrrolo[2,3-b]pyridin-5-yl)oxy)-4-fluorobenzoate to form the intermediate A-4-2, which can undergo a hydrolysis reaction to form the carbocyclic acid intermediate A-4-3. Finally, the coupling of A-4-3 with appropriate side chain to afford the target compounds.

Similarly, the compounds of

Formula (v)

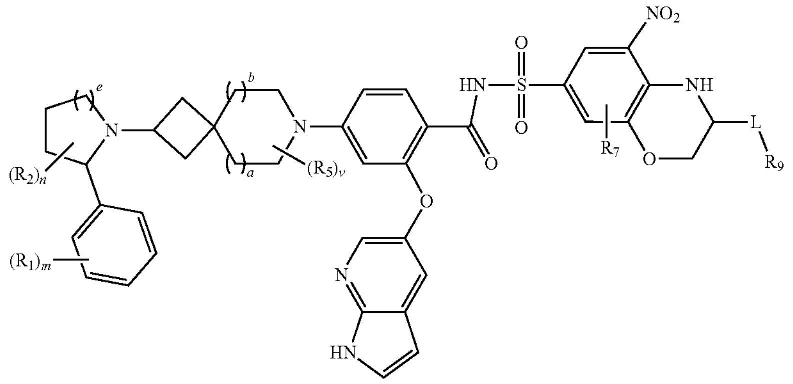

can be prepared by schemes similar to the Scheme A-4 by using appropriate staring materials and intermediates.

Similarly, the compounds of

Formula (iv)

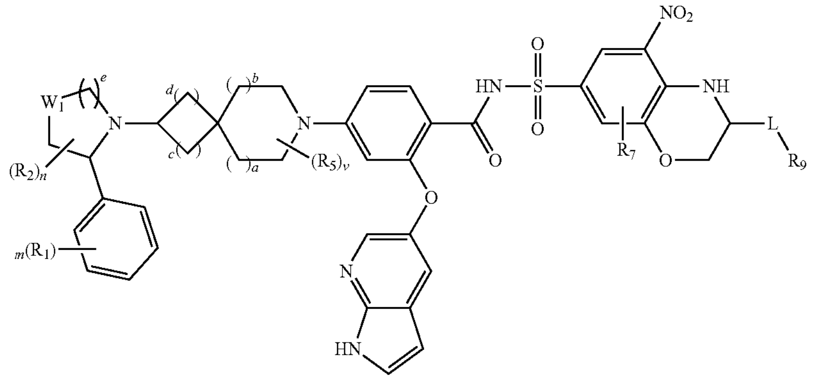

can be prepared by schemes similar to the Scheme A-4 by using appropriate staring materials and intermediates.

Similarly, the compounds of

Formula (iii)

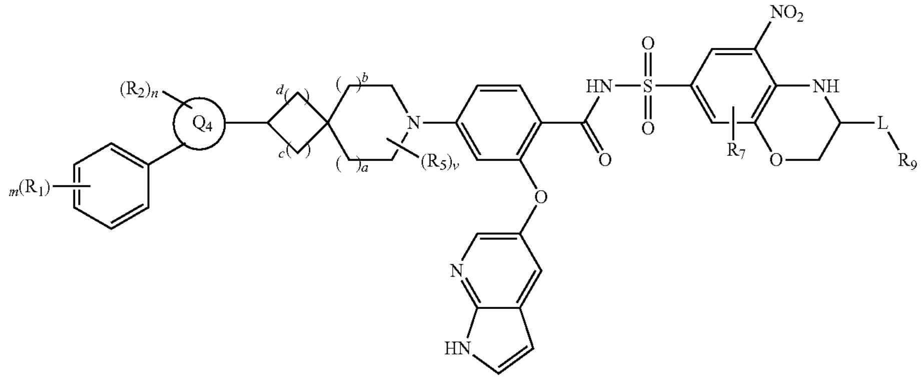

can be prepared by schemes similar to the Scheme A-4 by using appropriate staring materials and intermediates.

Similarly, the compounds of
Formula (ii)
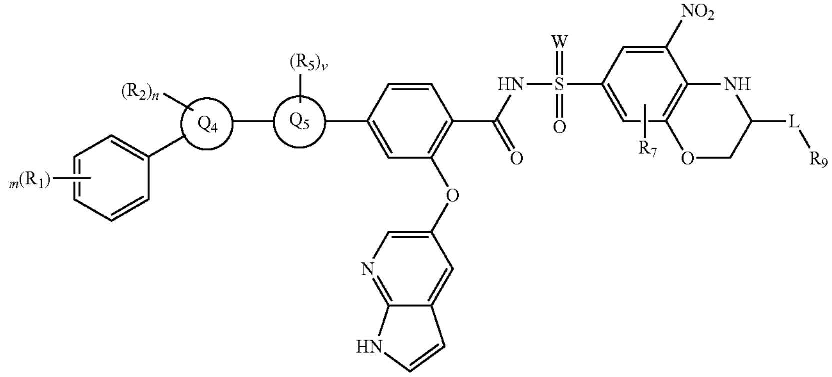
can be prepared by schemes similar to the Scheme A-4 by using appropriate staring materials and intermediates.
Similarly, the compounds of
Formula (i)
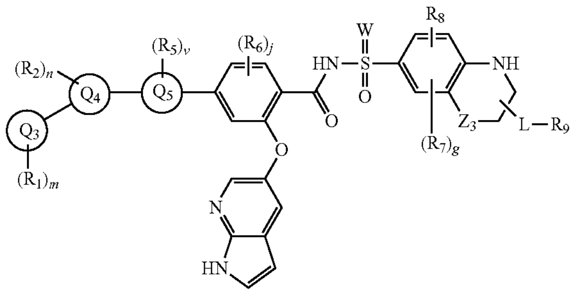
can be prepared by schemes similar to the Scheme A-4 by using appropriate staring materials and intermediates.
An approach to synthesize of target compounds of
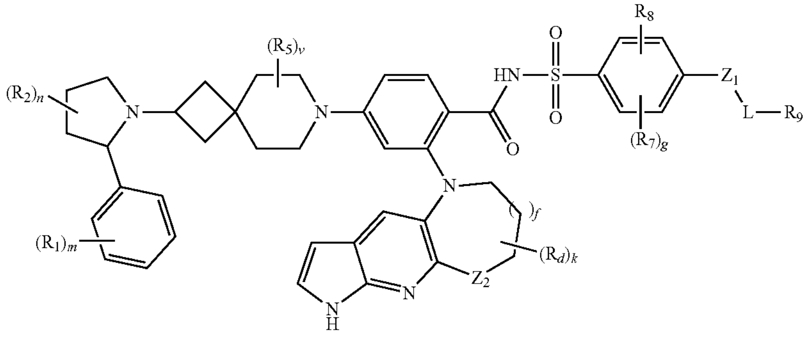

is described in Scheme A-5:
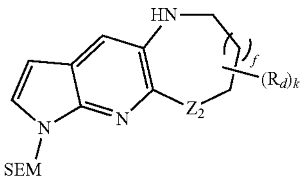
A-5-1
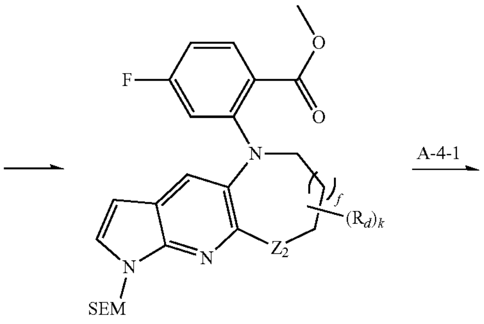
A-5-2
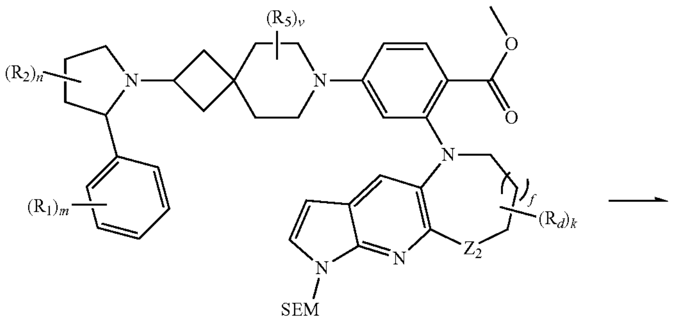
A-5-3
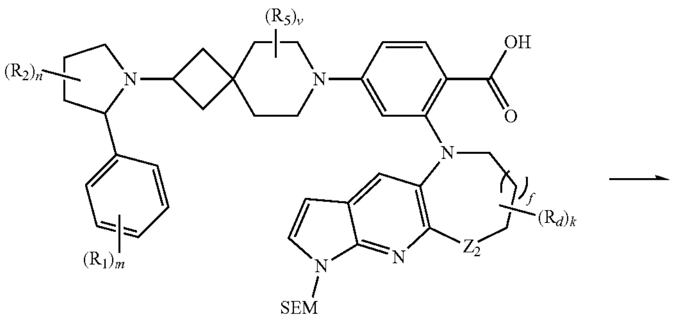
A-5-4
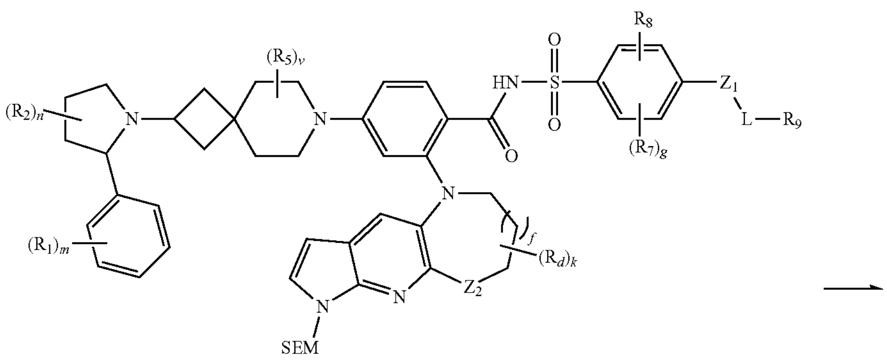
A-5-5

-continued

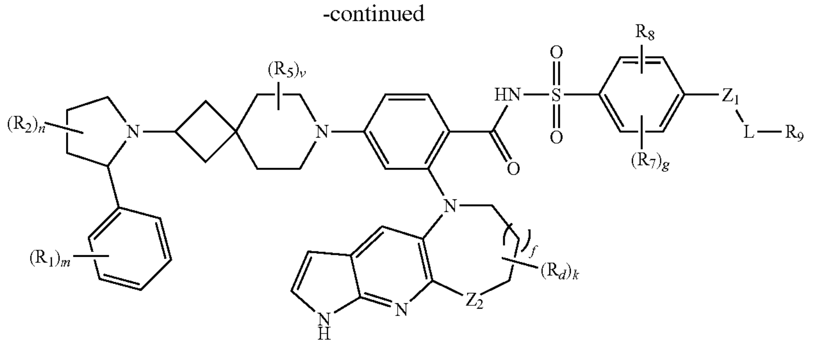

In Scheme A-5, the intermediate A-5-1 can be prepared by standard organic reactions or by the methods similar to those described in International Application Publication Nos. WO/2017/132474, WO/2019/040573, WO/2019/040550, WO2020041405, WO2020041406, PCT/US2020/020010, WO/2020/140005. A-5-1 can reaction with methyl 2,4-difluorobenzoate to form the intermediate A-5-2, which can react with A-4-1 to afford the intermediate A-5-3. The hydrolysis of A-5-3 in basic condition will lead to A-5-4, which can react with appropriate side chain followed by deprotection of SEM group to afford the target compounds.

Similarly, the compounds of

Formula (E)

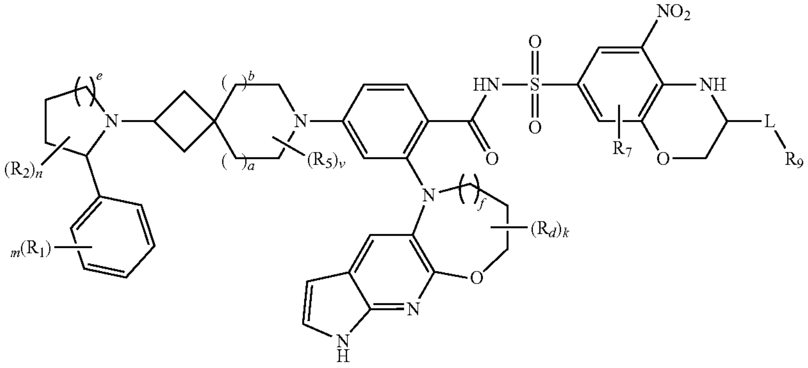

can be prepared by schemes similar to the Scheme A-5 by using appropriate staring materials and intermediates.

Similarly, the compounds of

Formula (D)

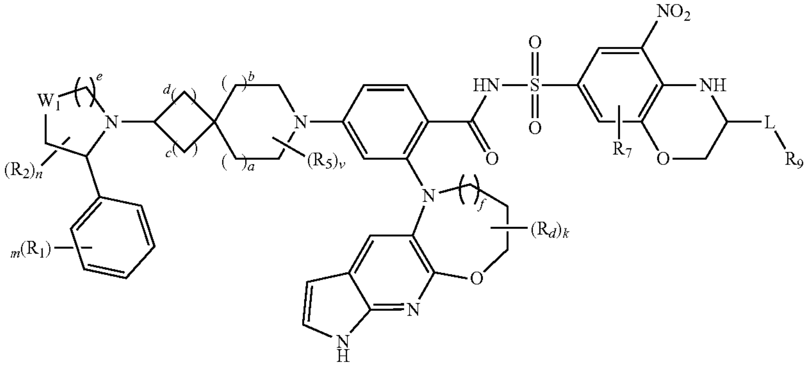

can be prepared by schemes similar to the Scheme A-5 by using appropriate staring materials and intermediates.

Similarly, the compounds of

Formula (C)

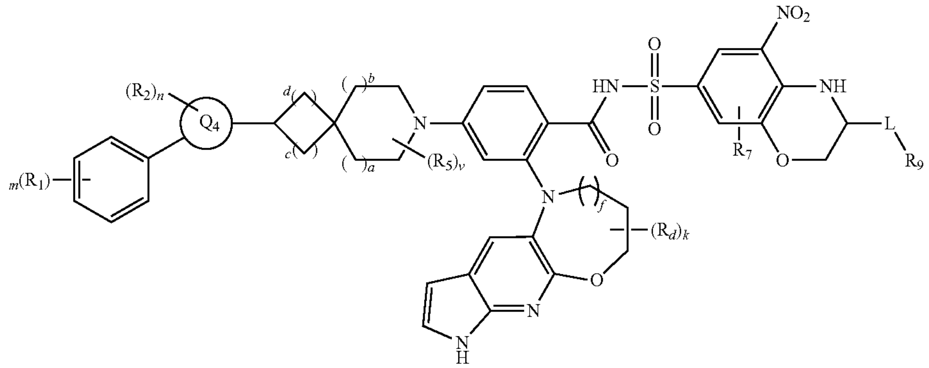

can be prepared by schemes similar to the Scheme A-5 by using appropriate staring materials and intermediates.

Similarly, the compounds of

Formula (B)

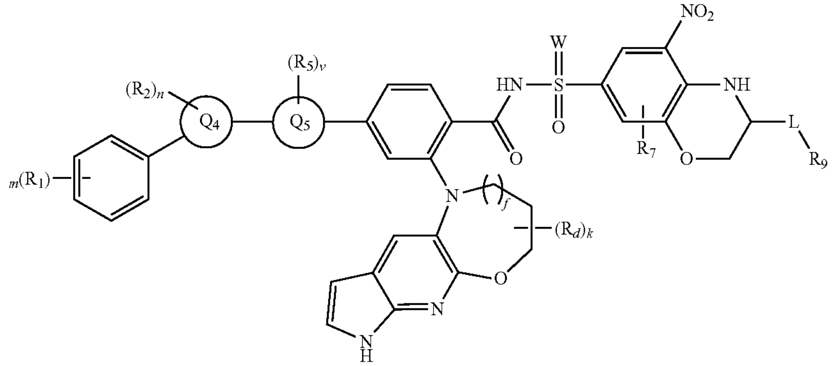

can be prepared by schemes similar to the Scheme A-5 by using appropriate staring materials and intermediates.

Similarly, the compounds of

Formula (A)

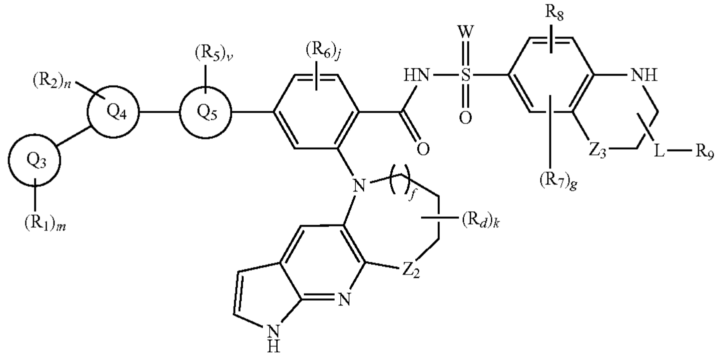

can be prepared by schemes similar to the Scheme A-5 by using appropriate staring materials and intermediates.

An approach to synthesize of target compounds of
Formula (VI)
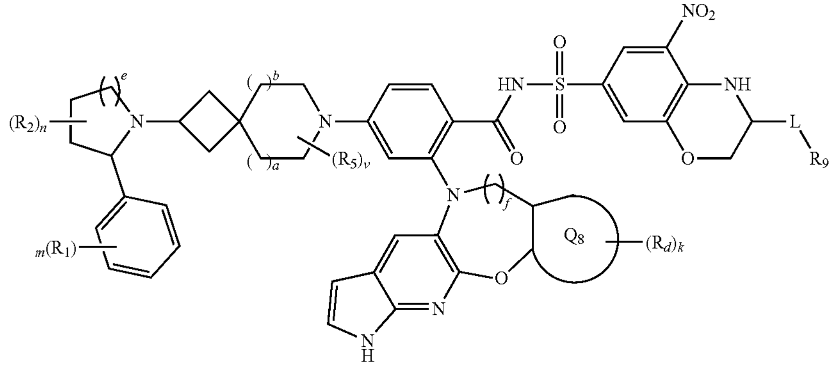
is described in Scheme A-7:
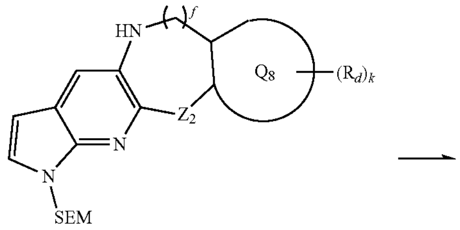
A-7-1
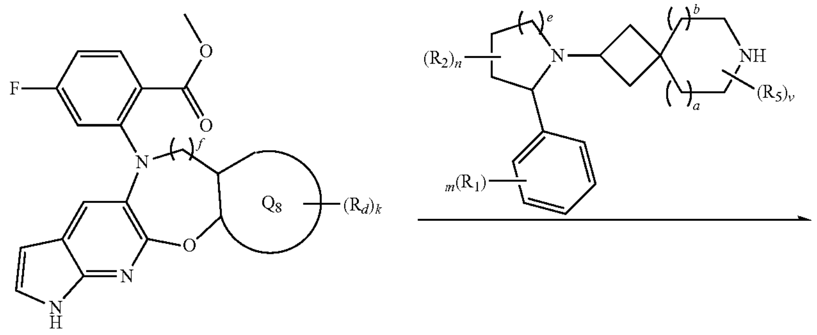
A-7-2
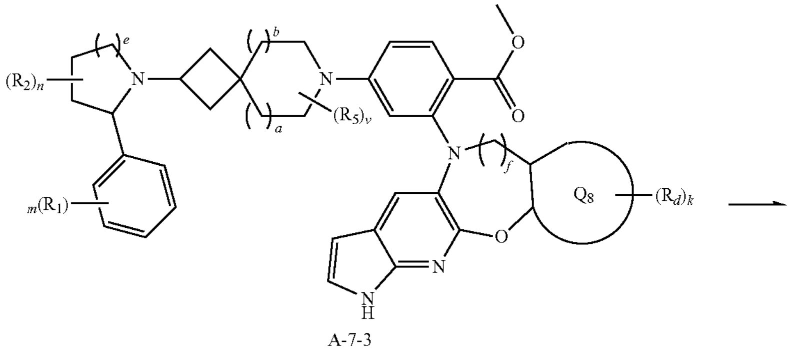
A-7-3

-continued

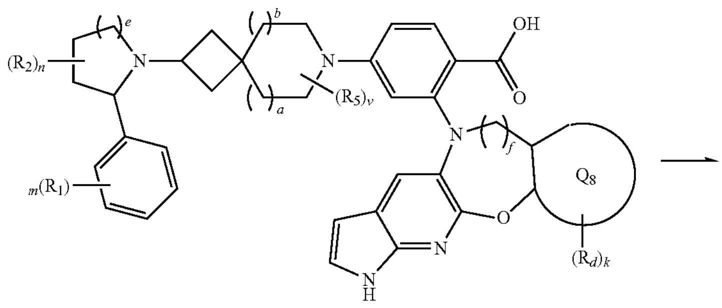

A-7-4

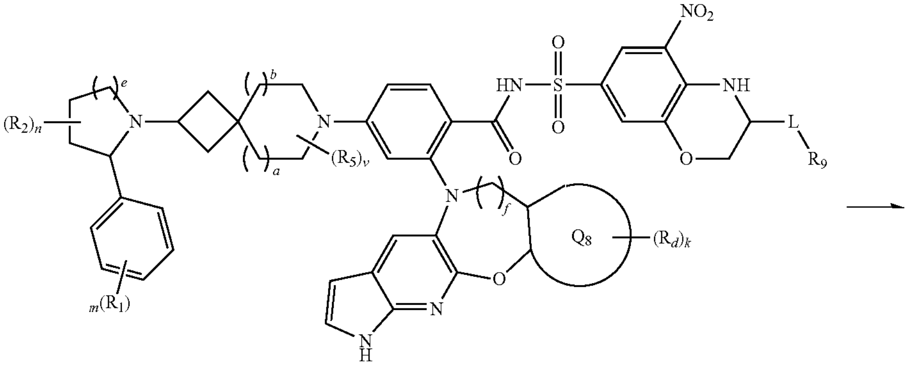

A-7-5

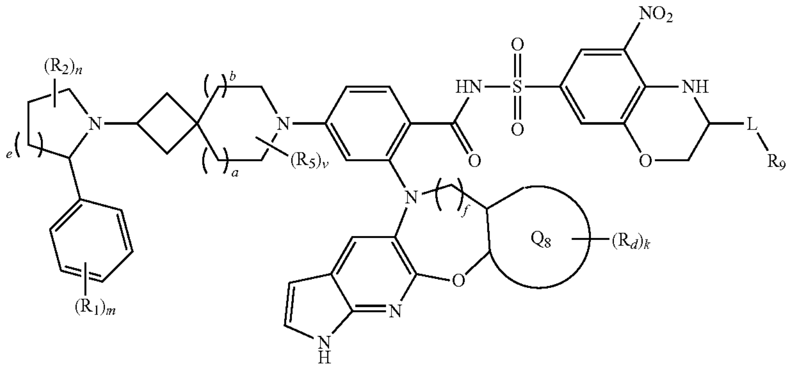

Formula (VI)

In Scheme A-7, the intermediate A-7-1 can be prepared by standard organic reactions or by the methods similar to those described in International Application Publication Nos. WO/2017/132474, WO/2019/040573, WO/2019/040550, WO2020041405, WO2020041406, PCT/US2020/020010, WO/2020/140005. A-7-1 can reaction with methyl 2,4-difluorobenzoate to form the intermediate A-7-2, which can react with A-7-1 to afford the intermediate A-7-3. The hydrolysis of A-7-3 in basic condition will lead to A-7-4, which can react with appropriate side chain followed by deprotection of SEM group to afford the target compounds.

Similarly, the compounds of

Formula (IV)

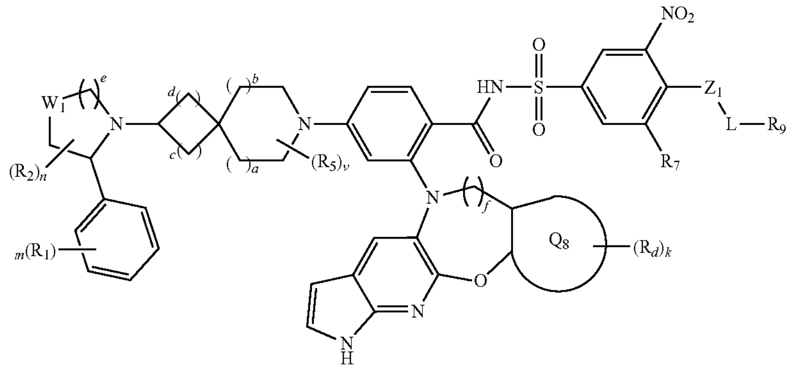

can be prepared by schemes similar to the Scheme A-7 by using appropriate staring materials and intermediates.

Similarly, the compounds of

Formula (III)

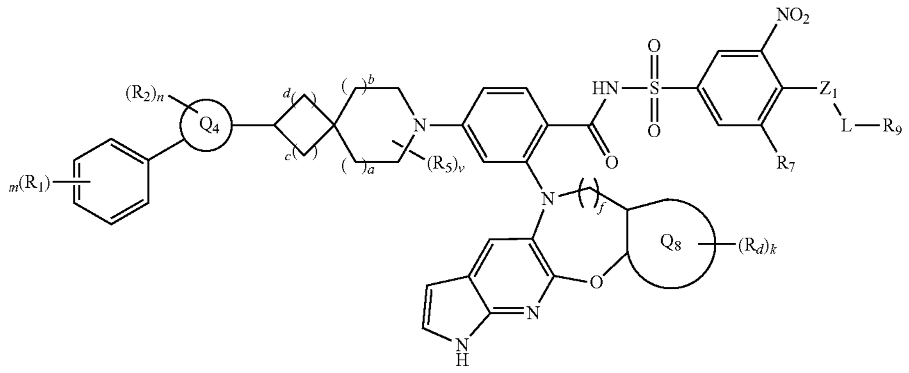

can be prepared by schemes similar to the Scheme A-7 by using appropriate staring materials and intermediates.

Similarly, the compounds of

Formula (II)

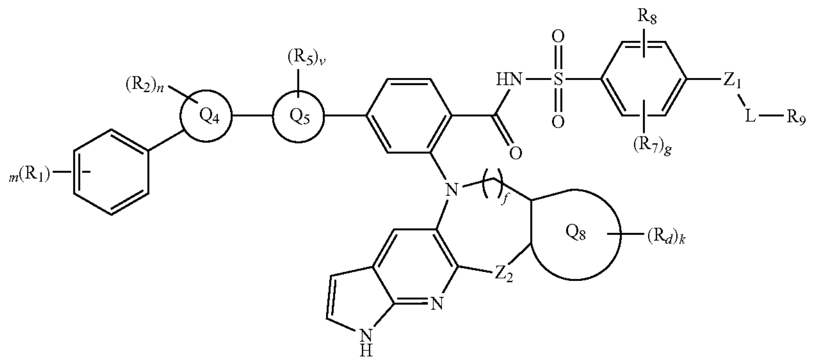

can be prepared by schemes similar to the Scheme A-7 by using appropriate staring materials and intermediates.

Similarly, the compounds of

Formula (I)

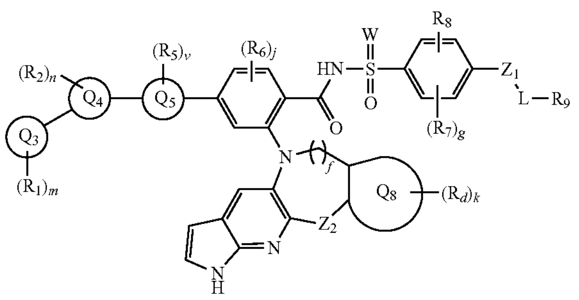

can be prepared by schemes similar to the Scheme A-7 by using appropriate staring materials and intermediates.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1H$ spectra were obtained on XL400 (400 MHz) and are reported as ppm down field from Me4Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example INT-1: Preparation of 1-((4'-chloro-5,5-dimethyl-3,4,5,6-tetrahydro-[1,1'-biphenyl]-2-yl)methyl)piperazine Synthesis of 2-bromo-4,4-dimethylcyclohex-1-enecarbaldehyde 2: A solution of anhydrous chloroform (57 ml) and anhydrous N,N-dimethylformamide (9 mL) were cooled to ~3° C. (internal temperature) under nitrogen before phosphorus tribromide (10 mL, 0.1 mol) was introduced dropwise at a rate so that the reaction was maintained at ~3° C. After the addition was complete the reaction was allowed to warm slowly to ~10° C. and then the temperature was raised to 70° C. where it was maintained for 30 min. The reaction was cooled to rt and 3,3-dimethylcyclohexanone 1 (5 g, 0.04 mol) was added slowly over 20 min. After the addition was complete the reaction was warmed to 70° C. and it was stirred for 1.5 h. The mixture was then cooled to 0° C. and a solution of 4M sodium acetate (53 ml) was added slowly. The pH of the resulting solution was adjusted to ~7 using a solution of 5M NaOH and the mixture was then extracted with heptanes (100 mL×3). The combined organic fractions were dried ($Na_2SO_4$), filtered and concentrated under reduced pressure to give 2-bromo-4,4-dimethylcyclohex-1-enecarbaldehyde 2 (4 g, 49%) as a yellow oil.

Synthesis of 2-(4-chlorophenyl)-4,4-dimethylcyclohex-1-enecarbaldehyde 3: To a degassed solution of 2-bromo-4,4-dimethylcyclohex-1-enecarbaldehyde 2 (5 g, 0.023 mol) and 4-chlorophenyl boronic acid (3.6 g, 0.023 mol) in 1,4-dioxane (50 mL) at rt was added a solution of 2M $Na_2CO_3$ (20.4 ml). Nitrogen was bubbled through the mixture for 2 min and then $PdCl_2$(dppf) (0.5 g) was added. The reaction flask was heated to 120° C. where it was maintained for 3 h. After this time the suspension was cooled to rt and filtered through Celite.

The collected solids were washed with additional dichloromethane and the combined filtrate and washings were concentrated under reduced pressure. Purification by column chromatography on silica with PE:EA=20:1 gave 2-(4-chlorophenyl)-4,4-dimethylcyclohex-1-enecarbaldehyde 3 (3 g, 53%) as a white solid. MS: 249[M+H]$^+$ Synthesis of (2-(4-chlorophenyl)-4,4-dimethylcyclohex-1-enyl)methanol 4: A solution of 2-(4-chlorophenyl)-4,4-dimethylcyclohex-1-enecarbaldehyde 3 (20 g, 80.6 mmol) in MeOH (100 mL) was cooled to 0° C., $NaBH_4$ (3.1 g, 80.6 mmol) was added portionwise to the reaction at a rate so that the reaction was maintained at 0-5° C. After added, the mixture was stirred for 1 h at 0° C. Water was added slowly to the mixture and extracted with EA (200 mL×3), the organic layer was washed with brine and dried $Na_2SO_4$, filtered and concentrated under reduced pressure to give (2-(4-chlorophenyl)-4,4-dimethylcyclohex-1-enyl)methanol 4 (15 g, 75%) as a white solid. MS: 233[M+H-$H_2O$]$^+$ Synthesis of 1-(2-(bromomethyl)-5,5-dimethylcyclohex-1-enyl)-4-chlorobenzene 5: A solution of (2-(4-chlorophenyl)-4,4-dimethylcyclohex-1-enyl)methanol 4 (15 g, 0.060 mol) and in $Et_2O$ (300 ml) was cooled to 0° C. before phosphorus tribromide (7.5 mL) was added dropwise to the mixture, after added, the mixture was stirred for 1 h at 0° C. for 90 minutes. The reaction mixture was added $H_2O$ before being extracted with EA. The organic layer was washed with a saturated $NaHCO_3$ solution and brine and dried $Na_2SO_4$, filtered and concentrated under reduced pressure to give 1-(2-(bromomethyl)-5,5-dimethylcyclohex-1-enyl)-4-chlorobenzene 5 (18 g, 96%) as a colorless oil.

Synthesis of tert-butyl 4-((2-(4-chlorophenyl)-4,4-dimethylcyclohex-1-enyl)methyl)piperazine-1-carboxylate—To a solution of 1-bromo-2-(bromomethyl)-5,5-dimethylcyclohex-1-ene 5 (21 g, 0.067 mol) and tert-butyl piperazine-1-carboxylate (12.4 g, 0.067 mol) in dichloromethane (200 ml) at rt was added TEA (12.2 g, 0.12 mol). The reaction was stirred for 2 h. The reaction mixture was concentrated under reduced pressure to give the crude product. Purification by column chromatography on silica with PE:EA=20:1 provided tert-butyl 4-((2-(4-chlorophenyl)-4,4-dimethylcyclohex-1-enyl)methyl)piperazine-1-carboxylate 6 (21 g, 75%).

Synthesis of 1-((2-(4-chlorophenyl)-4,4-dimethylcyclohex-1-enyl)methyl)piperazine hydrogen chloride: To a solution of tert-butyl 4-((2-(4-chlorophenyl)-4,4-dimethylcyclohex-1-enyl)methyl)piperazine-1-carboxylate 6 (30 g, 0.072 mol) in MeOH (20 ml) was added conc. HCl (50 mL). The reaction was stirred for 24 hours and then concentrated under reduced pressure. A saturated solution of $Na_2CO_3$ was added to adjust the pH to ~8-9 and the mixture was extracted with dichloromethane (×2). The combined extracts were washed with brine, dried ($Na_2SO_4$), filtered and concentrated under reduced pressure. The oil product was treated with MeOH/HCl(g) (3M, 500 mL) and stirred for 1 hour, then concentrated under reduced pressure to get the product 1-((2-(4-chlorophenyl)-4,4-dimethylcyclohex-1-enyl)methyl)piperazine hydrogen chloride IM-14-1 (23 g, 83%). MS: 319[M+H]$^+$ $^1H$ NMR (400 MHz, DMSO) δ 11.51 (s, 1H), 9.60 (s, 1H), 9.18 (s, 1H), 7.45 (d, J=8.2 Hz, 2H), 7.15 (d, J=8.0 Hz, 2H), 3.43 (s, 8H), 2.84 (s, 2H), 2.39 (s, 2H), 2.03 (s, 2H), 1.45 (t, J=6.0 Hz, 2H), 0.96 (s, 6H).

Example INT-2: Preparation of 3-nitro-4-(((tetrahydro-2H-pyran-4-yl)methyl)amino)benzenesulfonamide To a 500 mL three-neck RB flask equipped with a mechanical stirrer were charged the 4-chloro-3-nitrobenzenesulfonamide (23.7 g, 100 mmol), DIPEA (12.9 g, 100 mmol), (tetrahydro-2H-pyran-4-yl)methanamine (11.5 g, 100 mmol) and acetonitrile (200 mL). The reaction mixture was adjusted to an internal temperature of 80° C. and agitated for no less than 12 hours. The product solution was cooled down to 40° C. and agitated for no less than 1 hour until precipitation observed. The product slurry was further cooled to 20° C. Water (80 mL) was slowly charged over no less than 1 hour, and the mixture cooled to 10° C. and agitated for no less than 2 hours before collected by filtration. The wet cake was washed with 1:1 mix of acetonitrile: water (40 mL). The wet cake was rinsed with water (80 mL) at 40° C. for no less than 1 hour before collected by filtration. The wet cake was rinsed with water (20 mL), and dried at 75° C. under vacuum to give the 3-nitro-4-(((tetrahydro-2H-pyran-4-yl)methyl)amino)benzenesulfonamide (24.5 g, 78%) as an orange solid. $^1$H NMR (400 MHz, DMSO) δ 8.60 (t, J=5.9 Hz, 1H), 8.48 (d, J=2.2 Hz, 1H), 7.84 (dd, J=9.2, 2.0 Hz, 1H), 7.54-7.18 (m, 3H), 3.86 (dd, J=11.3, 3.2 Hz, 2H), 3.35 (s, 2H), 3.27 (t, J=10.9 Hz, 2H), 1.92 (ddd, J=11.2, 7.4, 3.9 Hz, 1H), 1.62 (d, J=11.4 Hz, 2H), 1.27 (qd, J=12.3, 4.4 Hz, 2H).

Example INT-3: Preparation of 4-[[(4-fluorooxan-4-yl)methyl]amino]-3-nitrobenzene-1-sulfonamide Into a 50-mL round-bottom flask, was placed (4-fluorooxan-4-yl)methanamine hydrochloride (500 mg, 2.95 mmol, 1.00 equiv), 4-fluoro-3-nitrobenzene-1-sulfonamide (650 mg, 2.95 mmol, 1.00 equiv), tetrahydrofuran (15 mL), $Cs_2CO_3$ (2.8 g, 8.59 mmol, 3.00 equiv). The resulting solution was stirred for 14 h at 50° C. in an oil bath. The reaction mixture was cooled to room temperature. The resulting mixture was filtered and concentrated under vacuum. The residue was applied onto a silica gel column with ethyl acetate/petroleum ether (4:1). This resulted in 650 mg (66%) of 4-[[(4-fluorooxan-4-yl)methyl]amino]-3-nitrobenzene-1-sulfonamide as a yellow solid. LCMS (ES, m/z): M+1: 334. H-NMR: (300 MHz, DMSO, ppm): δ 8.58 (t, J=6.3 Hz, 1H), 8.49 (d, J=2.1 Hz, 1H), 7.90-7.80 (m, 1H), 7.44 (d, J=9.3 Hz, 1H), 7.34 (s, 2H), 3.87-3.70 (m, 4H), 3.61-3.50 (m, 2H), 1.95-1.70 (m, 4H).

Example INT-4: Preparation of (S)-4-((1,4-dioxan-2-yl)methylamino)-3-nitrobenzenesulfonamide Synthesis of (R)-1-chloro-3-(2-chloroethoxy)propan-2-ol: (R)-2-(chloromethyl)oxirane (500.0 g, 5.4 mol, 1.00 equiv) was slowly added to a stirred solution of 2-chloroethanol (870.0, 10.8 mol, 2.00 equiv) and $BF_3 \cdot Et_2O$ (38.0 g, 27 mmol, 0.05 equiv) at 45° C. The reaction mixture was heated on an oil bath for 3 h at 45° C. The reaction mixture was cooled to R,T and Diethyl ether (100 mL) was added to this solution. The organic layer was washed with water (2×300 mL), dried over magnesium sulfate, and concentrated to yield a light brown liquid (R)-1-chloro-3-(2-chloroethoxy)propan-2-ol (800.0 g, quantitative). H-NMR: (300 MHz, DMSO-$d_6$, ppm) δ: 3.85-3.47 (m, 9H).

Synthesis of (R)-2-((2-chloroethoxy)methyl)oxirane. (R)-1-chloro-3-(2-chloroethoxy)propan-2-ol (800.0 g, crude, 4.7 mol, 1.0 eq) was added dropwise to a stirred solution of NaOH (465.0 g, 11.6 mol, 2.5 eq) in water (500 mL) on an ice-bath. The ice-bath was immediately removed after addition of (R)-1-chloro-3-(2-chloroethoxy)propan-2-ol. After stirring 2 h at an ambient temperature, diethyl ether (1.5 L) and water (500 mL) were added. The organic layer was washed with water (1×50 mL), dried over sodium sulfate, and concentrated to give a light brown liquid (R)-2-((2-chloroethoxy)methyl)oxirane (400.0 g). H-NMR: (300 MHz, CDCL3, ppm) δ: 3.82-3.52 (m, 5H), 3.40-3.35 (m, 1H), 3.11-3.09 (m, 1H), 2.75-2.73.

Synthesis of (S)-(1,4-dioxan-2-yl)methanol. (R)-2-((2-chloroethoxy)methyl)oxirane (400.0 g, 2.94 mol, 1.0 eq) was added to a solution of NaOH (294.0 g, 7.35 mol, 2.5 eq) in water (2900 mL) at room temperature. The reaction mixture was heated on an oil bath for 2 h at 90° C. The resulting solution was cooled to R,T and adjusted PH value to 5 by HCl (6 M). The mixture was concentrated and the residue was distilled (90-95° C., 0.1 kPa) under vacuum pump to give a colorless oil (S)-(1,4-dioxan-2-yl)methanol (110 g, 31.7%). H-NMR: (300 MHz, CDCL3, ppm) δ: 3.85-3.42 (m, 9H), 2.15 (bs, 1H).

Synthesis of (R)-(1,4-dioxan-2-yl)methyl methanesulfonate. A mixture of (S)-(1, 4-dioxan-2-yl)methanol (50.0 g, 0.42 mol, 1.0 eq), TEA (63.6 g, 0.63 mol, 1.5 eq) and DCM (500 mL) at ice-bath, MsCl (48.1 g, 0.42 mol, 1.0 eq) was added dropwise. And then, the ice-bath removed and the mixture was stirred at R,T for 2 hours. The reaction mixture was washed by water (2×50 mL) and the organic phase was dried over sodium sulfate, and concentrated to give a light brown oil (R)-(1,4-dioxan-2-yl)methyl methanesulfonate (71.0 g, 83%). H-NMR: (300 MHz, CDCL3, ppm) δ: 4.23-4.20 (m, 2H), 3.82-3.56 (m, 6H), 3.50-3.40 (m, 1H), 3.02 (m, 3H).

Synthesis of (S)-(1,4-dioxan-2-yl)methanamine: In 1000 mL autoclave, to a solution of (R)-(1,4-dioxan-2-yl)methyl methanesulfonate (70.0 g, 0.36 mol, 1.0 eq) in $NH_3 \cdot MeOH$ (7 M, 500 mL) was stirred at 80° C. for 12 hours, the reaction mixture was cooled to R,T and concentrated to give a light brown oil (S)-(1,4-dioxan-2-yl)methanamine (30.0 g, 73%). NMR: (300 MHz, DMSO-$d_6$, ppm) δ: 8.27 (bs, 2H), 3.82-3.42 (m, 6H), 3.24-3.20 (m, 1H), 2.98-2.62 (m, 2H).

Synthesis of (S)-4-((1,4-dioxan-2-yl)methylamino)-3-nitrobenzenesulfonamide: A mixture of (S)-(1,4-dioxan-2-yl) methanamine (25.0 g, 0.21 mol, 1.0 eq), 4-fluoro-3-nitrobenzenesulfonamide (46.0 g, 0.21 mol, 1.0 eq) and $Cs_2CO_3$ (137.3 g, 0.42 mol, 2.0 eq) in THF (700 mL) was stirred at 50° C. for 6 hours, LCMS showed material was consumed completely, the reaction mixture was cooled R,T and poured into water (3500 mL). The mixture was filtrated and collected filtrate cake and dried by oven to give a yellow solid (S)-4-((1,4-dioxan-2-yl)methylamino)-3-nitrobenzenesulfonamide (60.0 g, 89.5%). H-NMR: (300 MHz, DMSO-$d_6$, ppm) δ: 8.52-8.47 (m, 2H), 7.86-7.83 (m, 1H), 7.28-7.00 (m, 3H), 3.82-3.29 (m, 9H).

Example INT-5: Preparation of methyl 2-bromo-4-(4-[[2-(4-chlorophenyl)-4,4-dimethylcyclohex-1-en-1-yl]methyl]piperazin-1-yl)benzoate Into a 250-mL round-bottom flask, was placed a solution of Example 1-1, i.e, 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS: (ES, m/z): M+1=533, 531.

Example INT-6: Preparation of 2-bromo-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide Synthesis of methyl 2-bromo-4-(4-((2-(4-chlorophenyl)-4,4-dimethylcyclohex-1-enyl)methyl)piperazin-1-yl)benzoate Into a 20000-mL round-bottom flask, was placed 1-((2-(4-chlorophenyl)-4,4-dimethylcyclohex-1-enyl)methyl)piperazine dihydrochloride (600 g, 1.53 mol, 1 equiv), methyl 2-bromo-4-fluorobenzoate (357 g, 1.53 mol, 1 equiv), DBU (319 g, 6.12 mol, 4 equiv) and DMSO (8000 mL). The resulting solution was stirred for 20 h at 70 degrees C. LCMS showed material was completely consumed. The resulting mixture was cooled to R,T and poured into water (32 L). The mixture was filtrated, collection of filter cake and the filter cake was washed by water (3000 mL×3) and dried by oven to give product 740 g (Y: 91%) methyl 2-bromo-4-(4-((2-(4-chlorophenyl)-4,4-dimethylcyclohex-1-enyl)methyl)piperazin-1-yl)benzoate as a white solid. H-NMR—PH-PHNW-4-55-400: (300 MHz, DMSO-$d_6$, ppm) δ: 7.73 (d, J=9.0 Hz, 1H), 7.42-7.39 (m, 2H), 7.18-7.12 (m, 3H), 6.97-6.94 (m, 1H), 4.00-3.84 (m, 2H), 3.76 (s, 2H), 3.57 (s, 3H), 3.51-3.33 (m, 4H), 2.79-2.60 (m, 2H), 2.32-2.30 (m, 2H), 2.03-1.97 (m, 2H), 1.47-1.45 (m, 2H), 0.96 (s, 6H).

Synthesis of 2-bromo-4-(4-((2-(4-chlorophenyl)-4,4-dimethylcyclohex-1-enyl) methyl)piperazin-1-yl)benzoic acid: Into a 20000-mL round-bottom flask, was placed methyl 2-bromo-4-(4-((2-(4-chlorophenyl)-4,4-dimethylcyclohex-1-enyl)methyl)piperazin-1-yl)benzoate (730 g, 1.37 mol, 1 equiv), LiOH (131.5 g, 5.48 mol, 4 equiv) and MeOH/THF/water (4500 mL/3000 mL/1000 mL). The resulting solution was stirred for 16 h at 70 degrees C. LCMS showed material was completely consumed. The resulting mixture was cooled to R,T and concentrated. The residue was diluted with water (5000 mL) and the mixture was adjust PH to 3-5 with HCl (6 M), followed by filtrated, collection of filter cake and dried by oven to give product 650 g (Y: 93%) 2-bromo-4-(4-((2-(4-chlorophenyl)-4,4-dimethylcyclohex-1-enyl)methyl)piperazin-1-yl)benzoic acid as a white solid. H-NMR—PH-PHNW-4-55-400: (300 MHz, DMSO-$d_6$, ppm) δ: 10.60 (bs, 1H), 7.73 (d, J=8.4 Hz, 1H), 7.42-7.39 (m, 2H), 7.14-7.11 (m, 3H), 6.95-6.92 (m, 1H), 4.00-3.84 (m, 2H), 3.76 (s, 2H), 3.51-3.33 (m, 4H), 2.79-2.60 (m, 2H), 2.32-2.30 (m, 2H), 2.03-1.97 (m, 2H), 1.47-1.45 (m, 2H), 0.97 (s, 6H).

Synthesis of 2-bromo-4-(4-((2-(4-chlorophenyl)-4,4-dimethylcyclohex-1-enyl) methyl)piperazin-1-yl)-N-(3-nitro-4-((tetrahydro-2H-pyran-4-yl)methylamino)phenylsulfonyl) benzamide: Into a 20000-mL round-bottom flask, was placed 2-bromo-4-(4-((2-(4-chlorophenyl)-4,4-dimethylcyclohex-1-enyl)methyl)piperazin-1-yl)benzoic acid (583 g, 1.13 mol, 1 equiv), DCM (10 L), 3-nitro-4-[[(oxan-4-yl) methyl]amino]benzene-1-sulfonamide (338 g, 1.07 mol, 0.95 equiv), EDCI (326 g, 1.7 mol, 1.5 equiv), DMAP (551 g, 4.52 mol, 4 equiv). The resulting solution was stirred for overnight at 25 degrees C. LCMS showed material was completely consumed. The resulting mixture is followed by dilute hydrochloric acid (1.0 M) (1000 mL×3), saturated sodium bicarbonate (1000 mL×3) and brine (1000 mL×1), and then the organic phase was dried by $Na_2SO_4$, filtrated. The filtrate was concentrated to give product 857 g (Y: 93%) as a light brown yellow solid 2-bromo-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino) phenylsulfonyl)benzamide as a brown yellow solid. LC-MS: (ES, m/z): M+1=814/816/818, R,T=2.01 min. H-NMR—PH-PHNW-4-55-400: (300 MHz, DMSO-$d_6$, ppm) δ: 8.63-8.61 (m, 2H), 7.94-7.92 (m, 1H), 7.37-7.35 (m, 3H), 7.27-7.24 (m, 1H), 7.05-7.02 (m, 3H), 6.86-6.83 (m, 1H), 3.87-3.82 (m, 2H), 3.37-3.23 (m, 8H), 2.92 (s, 2H), 2.50-2.38 (m, 4H), 2.22-2.20 (m, 2H), 2.00-1.97 (m, 2H), 1.64-1.60 (m, 2H), 1.48-1.46 (m, 2H), 1.26-1.20 (m, 2H), 0.97 (s, 6H).

Example INT-6: Preparation of methyl 2-((1H-pyrrolo[2,3-b]pyridin-5-yl) oxy)-4-bromobenzoate A mixture of methyl 4-bromo-2-fluorobenzoate (116.5 g, 0.5 mol), 1H-pyrrolo[2,3-b]pyridin-5-ol (67 g, 0.5 mol) and $K_2CO_3$ (138 g, 1.0 mol) in DMF (500 mL) was heated at 95° C. for about 16 h. The reaction mixture was cooled to ambient temperature, filtered and the filtrate was diluted with DCM (1 L). The resulting solution was washed with $H_2O$ (500 mL×2) and concentrated. The residue was recrystallized from EA (200 mL) and PE (400 mL), the cake (68 g) was collected as the first batch. The filtrate was concentrated and dissolved in EA (500 mL). The solution was washed with $H_2O$ (200 mL×2), concentrated, and slurried with EA (25 mL) and PE (25 mL) at reflux for 1 h, cooled to ambient temperature, filtered to give the product (38 g) as the second batch. The two batches of product were combined to afford the product (106 g, 61.3%) as a brown solid. MS (ESI, m/e) $[M+1]^+$ 346.9, 348.9.

Example INT-7: Preparation of 2-(2-cyclopropylphenyl) pyrrolidine

Step 1: tert-butyl 2-(2-bromophenyl) pyrrolidine-1-carboxylate: A mixture solution of 2-(2-bromophenyl) pyrrolidine (1.13 g, 5 mmol), $Boc_2O$ (2.16 g, 10 mmol), TEA (1.01 g, 10 mmol) and DMAP (cat) in DCM (20 mL) was stirred at room temperature for 16 hrs. Then the mixture solution was concentrated, and the residue was purified by chromatography on silica-gel (eluting with 100% PE to PE/EA=5/1) to give the product (1.6 g, 98.1%) as a colorless oil. MS (ESI, m/e) $[M+1]^+$ 270.0, 272.0

Step 2: tert-butyl 2-(2-cyclopropylphenyl) pyrrolidine-1-carboxylate: Under a nitrogen atmosphere, a mixture of tert-butyl 2-(2-bromophenyl) pyrrolidine-1-carboxylate (1.56 g, 4.7 mmol), cyclopropyl boronic acid (1.23 g, 14.3 mmol), Pd $(PPh_3)_4$ (540 mg, 0.47 mmol) and $K_2CO_3$ (1.99 g, 14.3 mmol) in 1,4-dioxane/$H_2O$ (9: 1, 20 mL) was stirred at 90° C. for 16 hours. Then the reaction mixture was filtered and concentrated, the crude product (1.4 g) was used directly in next step without purification. MS (ESI, m/e) [M+1]+ 232.1.

Step 3: 2-(2-cyclopropylphenyl) pyrrolidine: A mixture solution of tert-butyl 2-(2-cyclopropylphenyl) pyrrolidine-1-carboxylate (1.4 g) and TFA (5 mL) in DCM (50 mL) was stirred at room temperature for 16 hours. Then the mixture was concentrated to give a product (1.2 g, crude) as a yellow oil. MS (ESI, m/e) $[M+1]^+$ 188.1.

Example INT-8: Preparation of 1-(4-bromophenyl)-2-phenylpyrrolidine

To a degassed solution of 2-phenylpyrrolidine (588 mg, 4 mmol), 1-bromo-4-iodobenzene (1.132 g, 16 mmol), BINAP (497 mg, 0.8 mmol) and K-OtBu (1.2 g, 12 mmol) in toluene (25 ml) was added Pd 2 $(dba)_3$ (366 mg, 0.4 mmol). Nitrogen was bubbled through the mixture for 5 min, then heated to 90° C. and stirred overnight. After cooled to room temperature, the reaction mixture was washed with water and brine in sequence. The organic layer was dried over anhydrous $Na_2SO_4$, then filtered, concentrated and purified by column chromatography with 5%~20% EA/PE as eluent to give 1-(4-bromophenyl)-2-phenylpyrrolidine (750 mg, 62%) as a colorless oil. MS (ESI, m/e) $[M+1]^+$ 302.0, 304.1.

Example INT-9: Preparation of (S)-2-(2-(2-cyclopropylphenyl) pyrrolidin-1-yl)-7-azaspiro[3.5] nonane Step 1: tert-butyl (S)-2-(2-bromophenyl) pyrrolidine-1-carboxylate: To a solution of (S)-2-(2-bromophenyl) pyrrolidine (70 g, 311 mmol) in DCM (200 mL) were added Boc 20 (72.6 g, 333 mmol) and DMAP (cat) at 0° C. After addition, the mixture was stirred at room temperature for 1 hour. Then the mixture solution was washed with saturated aq. $NaHCO_3$ (100 mL×3), brine. The organic phase was dried with anhydrous $NaSO_4$, filtered, and concentrated to obtain pale brown solid (95 g, crude), which was not further purified for next step. MS (ESI, m/e) $[M+1]^+$ 326.1/328.2.

Step 2: tert-butyl (S)-2-(2-cyclopropylphenyl) pyrrolidine-1-carboxylate: Under a $N_2$ atmosphere, a mixture of tert-butyl (S)-2-(2-bromophenyl) pyrrolidine-1-carboxylate (88 g, 270 mmol), cyclopropyl boronic acid (68.9 g, 810 mmol), Pd $(dppf)_2Cl_2$ (19.7 g, 27 mmol) and $K_2CO_3$ (150 g, 1.08 mol) in 1,4-dioxane (270 mL) and $H_2O$ (30 mL) was stirred at 90° C. for 16 hours. After the reaction mixture was cooled to room temperature, the mixture was filtered, and the filtrate was concentrated in vacuum. The residue was purified by chromatography column on silica (eluent: DCM/$CH_3OH$=20/1) to obtain tert-butyl (S)-2-(2-cyclopropylphenyl) pyrrolidine-1-carboxylate as pale yellow oil 70 g (yield: 90%). MS (ESI, m/e) $[M+1]^+$ 288.1.

Step 3: (S)-2-(2-cyclopropylphenyl) pyrrolidine: To a solution of tert-butyl (S)-2-(2-cyclopropylphenyl) pyrrolidine-1-carboxylate (70 g, 244 mmol) in DCM (200 mL) was added HCl solution (200 mL, 4M in dioxane). After addition, the mixture was stirred for overnight at room temperature. After removal of solvent, the residue was diluted with water (200 mL) and EA (100 mL) under stirring, the separated water phase was adjusted to PH~11 and exacted with DCM (100 mL×2). The combined organic phase was dried with anhydrous $NaSO_4$, filtered, and concentrated to obtain (S)-2-(2-cyclopropylphenyl) pyrrolidine (42 g, crude) as brown oil. MS (ESI, m/e) $[M+1]^+$ 188.2.

Step 4: tert-butyl (S)-2-(2-(2-cyclopropylphenyl) pyrrolidin-1-yl)-7-azaspiro[3.5]nonane-7-carboxylate: To the mixture of (S)-2-(2-cyclopropylphenyl) pyrrolidine (3.74 g, 20 mmol) and tert-butyl 2-oxo-7-azaspiro[3.5] nonane-7-carboxylate (4.78 g, 20 mmol) in DCM (100 mL) was added NaBH $(AcO)_3$ (8.48 g, 40 mmol) at room temperature and stirred for 2 hours. The reaction mixture was quenched with aq. $NaHCO_3$ solution (200 mL), and then extracted with DCM (200 mL×2). The organic layer was combined, washed with brine and dried over $Na_2SO_4$. After evaporation in vacuum, the crude product (8.21 g) was obtained as a colorless oil without further purification for next step. MS (ESI, m/e) [M+1]+411.0.

Step 5: (S)-2-(2-(2-cyclopropylphenyl) pyrrolidin-1-yl)-7-azaspiro[3.5] nonane: To a solution of tert-butyl (S)-2-(2-(2-cyclopropylphenyl) pyrrolidin-1-yl)-7-azaspiro[3.5] nonane-7-carboxylate (8.2 g, 20 mmol) in DCM (200 mL) was added TFA (40 mL) at 20° C. and stirred at room temperature overnight. The mixture was concentrated in vacuum and diluted with DCM (200 mL) and aq. NaOH solution (1N, 200 mL) was added under stirring.

Then the organic layer was collected and dried over $Na_2SO_4$. After evaporation in vacuum, the crude product (6.2 g) was obtained as a brown oil without further purification for next step. $^1H$ NMR (400 MHz, $CDCl_3$) δ ppm: 7.61 (dd, J=8.0 Hz, J=4.0 Hz, 1H), 7.22-7.11 (m, 2H), 7.00-6.96 (m, 1H), 3.94 (t, J=8.0 Hz, 1H), 3.23-3.03 (m, 2H), 2.71-2.60 (m, 4H), 2.42-2.20 (m, 2H), 2.07-1.55 (m, 10H), 1.41-1.37 (m, 3H), 0.95-0.87 (m, 2H), 0.64-0.53 (m, 2H). MS (ESI, m/e) $[M+1]^+$ 311.0.

Example INT-10: Preparation of 2-(2-(2-cyclopropylphenyl)-4-methylpiperazin-1-yl)-7-azaspiro[3.5] nonane Step 1: methyl 2-bromo-2-(2-bromophenyl) acetate: To a solution of methyl 2-(2-bromophenyl) acetate (25 g, 109.14 mmol) in $CCl_4$ (250 mL) was added NBS (21.37 g, 120.65 mmol) and BPO (1.32 g, 5.46 mmol). The mixture was stirred at 85° C. for 5 hours.

TLC showed reactant was consumed completely. The mixture was poured into $H_2O$ (200 mL) and extracted with DCM (200 mL×3), washed with brine, dried over $Na_2SO_4$, filtered and concentrated. The residue was purified by prep-MPLC. Methyl 2-bromo-2-(2-bromophenyl) acetate (20 g) was obtained as a colorless oil. $^1H$ NMR (400 MHz, $CDCl_3$)$_6$ ppm: 7.79 (dd, J=1.0, 8.0 Hz, 1H), 7.58 (dd, J=1.0, 8.0 Hz, 1H), 7.40-7.34 (m, 1H), 7.21 (dt, J=1.5, 7.7 Hz, 1H), 5.98-5.83 (m, 1H), 3.82 (s, 3H).

Step 2: 3-(2-bromophenyl) piperazin-2-one: To a solution of methyl 2-bromo-2-(2-bromophenyl) acetate (20 g, 64.94 mmol) in MeOH (200 mL) was added DIEA (12.67 g, 98.04 mmol) and ethane-1,2-diamine (7.86 g, 130.72 mmol). The mixture was stirred at 25° C. for 12 hours. TLC showed reactant was consumed completely. The mixture was diluted with $H_2O$ (200 mL) and extracted with EA (200 mL×3), washed with brine, dried over Na $2SO_4$, filtered and concentrated to give crude 3-(2-bromophenyl) piperazin-2-one (14 g) as a white solid, which used in next step without further purification.

Step 3: tert-butyl 2-(2-(2-bromophenyl)-3-oxopiperazin-1-yl)-7-azaspiro[3.5]nonane-7-carboxylate: To a solution of 3-(2-bromophenyl) piperazin-2-one (7 g, 27.44 mmol) and tert-butyl 2-oxo-7-azaspiro[3.5] nonane-7-carboxylate (7.22 g, 30.18 mmol) in DCE (150 mL) was added AcOH (3.3 g, 54.88 mmol) and NaBH $(OAc)_3$ (11.63 g, 54.88 mmol). The mixture was stirred at 25° C. for 12 hours. TLC showed reactant was consumed completely. The reaction mixture was extracted with aq. $Na_2CO_3$ (150 mL) and EA (150 mL×3), dried over $Na_2SO_4$, filtered and concentrated. The residue was purified by prep-MPLC. Tert-butyl 2-(2-(2-bromophenyl)-3-oxopiperazin-1-yl)-7-azaspiro[3.5] nonane-7-carboxylate (8 g) was obtained as a white solid.

Step 4: tert-butyl 2-(2-(2-cyclopropylphenyl)-3-oxopiperazin-1-yl)-7-azaspiro[3.5]nonane-7-carboxylate: To a solution of tert-butyl 2-(2-(2-bromophenyl)-3-oxopiperazin-1-yl)-7-azaspiro[3.5] nonane-7-carboxylate (8 g, 16.72 mmol) and cyclopropylboronic acid (2.15 g, 25.08 mmol) in dioxane (100 mL) and $H_2O$ (10 mL) was added $Cs_2CO_3$ (16.34 g, 50.16 mmol) and Pd (dppf) $Cl_2$ (1.22 g, 1.67 mmol) under $N_2$ atmosphere. The mixture was stirred at 85° C. for 2 hours. LC/MS showed reactant was consumed completely and one main peak with desired MS signal. The reaction mixture was filtered and concentrated. The residue was diluted with $H_2O$ (50 mL)/EA (50 mL) and extracted with EA (50 mL×2), dried over $Na_2SO_4$, filtered and concentrated. The residue was purified by prep-MPLC. Tert-butyl 2-(2-(2-cyclopropylphenyl)-3-oxopiperazin-1-yl)-7-azaspiro[3.5] nonane-7-carboxylate (5 g, 68.02% yield) was obtained as a yellow solid. MS (ESI, m/e) $[M+1]^+$ 440.2.

Step 5: tert-butyl 2-(2-(2-cyclopropylphenyl)-4-methyl-3-oxopiperazin-1-yl)-7-azaspiro[3.5] nonane-7-carboxylate: To a solution of tert-butyl 2-(2-(2-cyclopropylphenyl)-3-oxopiperazin-1-yl)-7-azaspiro[3.5] nonane-7-carboxylate (5 g, 11.37 mmol) in THF (50 mL) was added NaH (0.5 g, 12.51 mmol, 60%) at 0° C. The mixture was stirred at 0° C. for 10 minutes. Then Mel (3.23 g, 22.75 mmol) was added at 0° C. The mixture was stirred at 25° C. for 5 hours. LC/MS showed reactant was consumed completely and one main peak with desired MS signal. The reaction mixture was diluted with $H_2O$ (50 mL) and extracted with EA (50 mL×3), dried over $Na_2SO_4$, filtered and concentrated. The residue was purified by prep-MPLC. Tert-butyl 2-(2-(2-cyclopropylphenyl)-4-methyl-3-oxopiperazin-1-yl)-7-azaspiro[3.5] nonane-7-carboxylate (4.7 g, 91.09% yield) was obtained as a white solid. MS (ESI, m/e) $[M+1]^+$ 454.2.

Step 6: tert-butyl 2-(2-(2-cyclopropylphenyl)-4-methylpiperazin-1-yl)-7-azaspiro[3.5] nonane-7-carboxylate: A mixture of tert-butyl 2-(2-(2-cyclopropylphenyl)-4-methyl-3-oxopiperazin-1-yl)-7-azaspiro[3.5] nonane-7-carboxylate (4.7 g, 10.36 mmol, 1 eq) in BH 3. THF (50 mL) was stirred at 70° C. for 12 hours. LC/MS showed reactant was consumed completely and one main peak with desired MS signal. The reaction mixture was quenched by MeOH (50 mL) at 0° C. and stirred at 25° C. for 30 minutes. Then the mixture was concentrated to afford tert-butyl 2-(2-(2-cyclopropylphenyl)-4-methylpiperazin-1-yl)-7-azaspiro[3.5] nonane-7-carboxylate (4.5 g). MS (ESI, m/e) $[M+1]^+$ 440.3.

Step 7: 2-(2-(2-cyclopropylphenyl)-4-methylpiperazin-1-yl)-7-azaspiro[3.5]nonane: A mixture of tert-butyl 2-(2-(2-cyclopropylphenyl)-4-methylpiperazin-1-yl)-7-azaspiro [3.5] nonane-7-carboxylate (4.5 g, 10.24 mmol) in DCM (25 mL) and TFA (25 mL) was stirred at 25° C. for 1 hr. LC/MS showed reactant was consumed completely and one main peak with desired MS signal. The reaction mixture was concentrated under reduced pressure to remove solvent. The residue was purified by prep-HPLC (TFA condition). The desired collection was concentrated and was dilute with $H_2O$ (20 mL) and added aq. $Na_2CO_3$ to adjust pH to ~9. The mixture was extracted with EA (20 mL×3), dried over $Na_2SO_4$, filtered and concentrated under reduced pressure to remove solvent. 2-(2-(2-cyclopropylphenyl)-4-methylpiperazin-1-yl)-7-azaspiro[3.5] (1.2 g) was obtained as a white solid. $^1H$ NMR (400 MHz, $CDCl_3$) δ ppm: 7.48 (s, 1H), 7.22-7.12 (m, 2H), 7.01 (s, 1H), 6.39 (s, 1H), 3.96 (d, J=7.3 Hz, 1H), 3.04-2.96 (m, 1H), 2.95-2.87 (m, 2H), 2.85-2.65 (m, 5H), 2.30 (s, 3H), 2.27 (s, 2H), 2.12 (s, 1H), 1.99 (s, 1H), 1.90-1.81 (m, 1H), 1.75-1.66 (m, 1H), 1.60-1.43 (m, 4H), 1.38-1.28 (m, 1H), 1.11 (d, J=4.4, 7.2, 11.5 Hz, 1H), 0.99-0.91 (m, 2H), 0.70 (s, 1H), 0.63-0.52 (m, 1H). MS (ESI, m/e) $[M+1]^+$ 340.3.

Example 1: Preparation of 4-(4-[[2-(4-chlorophenyl)-4,4-dimethylcyclohex-1-en-1-yl]methyl]piperazin-1-yl)-2-[methyl(1H-pyrrolo[2,3-b]pyridin-5-yl)phosphoroso]-N-[3-nitro-4-[(oxan-4-ylmethyl)amino]benzenesulfonyl]benzamide Synthesis of 5-(methylphosphoroso)-1-[[2-(trimethylsilyl)ethoxy]methyl]pyrrolo[2,3-b]pyridine: Into a 250-mL 3-necked round-bottom flask purged and maintained with an inert atmosphere of nitrogen, was added 5-bromo-1-[[2-(trimethylsilyl)ethoxy]methyl]pyrrolo[2,3-b]pyridine (10 g, 30.55 mmol, 1.00 equiv), tetrahydrofuran (100 mL). This was followed by the addition of butyllithium (12.22 mL, 30.55 mmol, 1.00 equiv) dropwise with stirring at −78° C. The resulting solution was stirred for 1 h at −78° C. Ethyl methylphosphinate (1.65 g, 15.27 mmol, 0.50 equiv) was added and allowed to react, for an additional 1 h at −78° C. The reaction was then quenched by the addition of 100 mL of 0.5M HCl. The resulting solution was extracted with 3×100 mL of dichloromethane. The resulting mixture was washed with 100 mL of brine. The mixture was dried over anhydrous sodium sulfate and concentrated. The residue was applied onto a silica gel column with dichloromethane/methanol (100:0-90:10). This resulted in 1.2 g (12.65%) of 5-(methylphosphoroso)-1-[[2-(trimethylsilyl)ethoxy]methyl]pyrrolo[2,3-b]pyridine as light yellow oil. LC-MS: (ES, m/z): 311 $[M-H]^-$ Synthesis of 4-(4-[[2-(4-chlorophenyl)-4,4-dimethylcyclohex-1-en-1-yl]methyl]piperazin-1-yl)-2-[methyl(1-[[2-(trimethylsilyl)ethoxy]methyl]pyrrolo[2,3-b]pyridin-5-yl)phosphoroso]-N-[3-nitro-4-[(oxan-4-ylmethyl)amino]benzenesulfonyl]benzamide: Into a 40-mL vial purged and maintained with an inert atmosphere of nitrogen, was added 2-bromo-4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]benzamide (315.15 mg, 0.387 mmol, 1.2 equiv), 5-(methylphosphoroso)-1-[[2-(trimethylsilyl)ethoxy]methyl]pyrrolo[2,3-b]pyridine (100.00 mg, 0.322 mmol, 1.00 equiv), dioxane, $Cs_2CO_3$ (209.93 mg, 0.644 mmol, 2 equiv), copper(I) iodide (61.35 mg, 0.322 mmol, 1 equiv), methyl[2-(methylamino)ethyl]amine (10.58 mg, 0.032 mmol, 0.1 equiv). The resulting solution was stirred for 4 h at 110° C. The reaction mixture was cooled to RT. The resulting solution was diluted with 20 mL of $H_2O$. The resulting solution was extracted with 4×20 mL of dichloromethane. The resulting mixture was washed with 30 mL of brine. The mixture was dried over anhydrous sodium sulfate and concentrated. The residue was applied onto a silica gel column with dichloromethane/methanol (100:0-90:10). This resulted in 230 mg (22.78%) of 4-(4-[[2-(4-chlorophenyl)-4,4-dimethylcyclohex-1-en-1-yl]methyl]piperazin-1-yl)-2-[methyl(1-[[2-(trimethylsilyl)ethoxy]methyl]pyrrolo[2,3-b]pyridin-5-yl)phosphoroso]-N-[3-nitro-4-[(oxan-4-ylmethyl)amino]benzenesulfonyl]benzamide as yellow solid. LC-MS: (ES, m/z): 1044 $[M-H]^-$ Synthesis of 4-(4-[[2-(4-chlorophenyl)-4,4-dimethylcyclohex-1-en-1-yl]methyl]piperazin-1-yl)-2-[methyl(1H-pyrrolo[2,3-b]pyridin-5-yl)phosphoroso]-N-[3-nitro-4-[(oxan-4-ylmethyl)amino]benzenesulfonyl]benzamide: Into a 40-mL vial, was added 4-(4-[[2-(4-chlorophenyl)-4,4-dimethylcyclohex-1-en-1-yl]methyl]piperazin-1-yl)-2-[methyl(1-[[2-(trimethylsilyl)ethoxy]methyl]pyrrolo[2,3-b]pyridin-5-yl)phosphoroso]-N-[3-nitro-4-[(oxan-4-ylmethyl)amino]benzenesulfonyl]benzamide (225.00 mg, 0.215 mmol, 1.00 equiv), THF (5.00 mL). This was followed by the addition of TBAF (1M in THF) (4.3. mL, 4.30 mmol, 20 equiv). To this was added ethane-1,2-diamine (379.71 mg, 4.30 mmol, 20.00 equiv). The resulting solution was stirred for 4 h at 70° C. The reaction mixture was cooled to RT. The resulting solution was diluted with 30 mL of $H_2O$. The resulting solution was extracted with 4×20 mL of dichloromethane. The resulting mixture was washed with 20 mL of brine. The mixture was dried over anhydrous sodium sulfate and concentrated. The residue was applied onto a silica gel column with dichloromethane/methanol (5:95). The crude product (70 mg) was purified by Prep-HPLC with the following conditions (IntelFlash-1): Column, c18 silica gel; mobile phase, $CH_3CN$:$H_2O$=65% 0.5% $NH_3 \cdot H_2O$; Detector, UV 220 nm. 19 mg product was obtained. This resulted in 19 mg (9.65%) of 4-(4-[[2-(4-chlorophenyl)-4,4-dimethylcyclohex-1-en-1-yl]methyl]piperazin-1-yl)-2-[methyl(1H-pyrrolo[2,3-b]pyridin-5-yl)phosphoroso]-N-[3-nitro-4-[(oxan-4-ylmethyl)amino]benzenesulfonyl]benzamide as yellow solid. LC-MS: (ES, m/z): 914 $[M-H]^-$, $^1H$ NMR (300 MHz, DMSO, ppm):) δ 10.24 (s, 1H), 8.73 (m, 1H), 8.38 (s, 1H), 8.31-7.73 (m, 4H), 7.26 (s, 2H), 6.98 (m, 2H), 6.83 (s, 1H), 6.70 (m, 1H), 6.42 (s, 1H), 4.25-3.92 (m, 2H), 3.74-3.38 (m, 3H), 3.39-3.04 (m, 8H), 2.88 (s, 3H), 2.72 (s, 1H), 2.37 (s, 6H) 2.24 (m, 6H), 2.02 (s, 3H), 1.97 (m, 2H), 1.74 (m, 1H), 1.46 (s, 4H), 1.41-1.33 (m, 2), 1.03 (m, 2H), 0.99 (m, 10H), 0.09 (s, 3H).

Example 2: Preparation of 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-[1H-pyrrolo[2,3-b]pyridin-5-yl]-3,4-dihydroisoquinolin-1-one Synthesis of 5-bromo-1-[[2-(trimethylsilyl)ethoxy]methyl]pyrrolo[2,3-b]pyridine: Into a 500-mL 3-necked round-bottom flask purged and maintained with an inert atmosphere of nitrogen, was placed a solution of 5-bromo-1H-pyrrolo[2,3-b]pyridine (20.00 g, 101.505 mmol, 1.00 equiv) in N,N-dimethylformamide (200.00 mL). This was followed by the addition of sodium hydride (3.65 g, 152.257 mmol, 1.50 equiv), in portions at 0° C. After 0.5 h stirring, to this was added SEM-Cl (25.38 g, 152.231 mmol, 1.50 equiv) dropwise with stirring at 0° C. The resulting solution was allowed to react with stirring for an additional 3 h at room temperature. The reaction was then quenched by the addition of 400 mL of water. The resulting solution was extracted with 2×300 mL of ethyl acetate The resulting mixture was washed with 2×300 ml of brine. The mixture was dried over anhydrous sodium sulfate and concentrated under vacuum. The residue was applied onto a silica gel column with ethyl acetate/petroleum ether (1:3). This resulted in 18 g (54.18%) of 5-bromo-1-[[2-(trimethylsilyl)ethoxy]methyl]pyrrolo[2,3-b]pyridine as dark yellow oil. LCMS (ES, m/z): M+1=328

Synthesis of tert-butyl 2-cyano-2-(1-[[2-(trimethylsilyl)ethoxy]methyl]pyrrolo[2,3-b]pyridin-5-yl) acetate: Into a 250-mL round-bottom flask purged and maintained with an inert atmosphere of nitrogen, was placed 5-bromo-1-[[2-(trimethylsilyl)ethoxy]methyl]pyrrolo[2,3-b]pyridine (8.50 g, 25.970 mmol, 1.00 equiv), dioxane (100.00 mL, 1180.408 mmol, 45.45 equiv), tert-butyl 2-cyanoacetate (7.33 g, 0.052 mmol, 2.0 equiv), t-BuOK (7.29 g, 0.065 mmol, 2.5 equiv), BrettPhos Pd G3 (2.35 g, 0.003 mmol, 0.1 equiv). The resulting solution was stirred for 16 h at 110° C. in an oil bath. The reaction was diluted with 100 mL of water. The resulting solution was extracted with 2×100 mL of ethyl acetate The resulting mixture was washed with 2×100 ml of brine. The mixture was dried over anhydrous sodium sulfate and concentrated under vacuum. The residue was applied onto a silica gel column with ethyl acetate/petroleum ether (1:3). This resulted in 5.3 g (52.66%) of tert-butyl 2-cyano-2-(1-[[2-(trimethylsilyl)ethoxy]methyl]pyrrolo[2,3-b]pyridin-5-yl)acetate as yellow oil. LCMS (ES, m/z): M+1=388

Synthesis of 2-(1-[[2-(trimethylsilyl)ethoxy]methyl]pyrrolo[2,3-b]pyridin-5-yl)acetonitrile: Into a 250-mL round-bottom flask, was placed tert-butyl 2-cyano-2-(1-[[2-(trimethylsilyl)ethoxy]methyl]pyrrolo[2,3-b]pyridin-5-yl)acetate (5.30 g, 13.675 mmol, 1.00 equiv), DMSO (60.00 mL, 844.714 mmol, 61.77 equiv), $H_2O$ (15.00 mL, 832.626 mmol, 60.88 equiv), NaCl (4.00 g, 68.443 mmol, 5.00 equiv). The resulting solution was stirred for 3 h at 120° C. in an oil bath. The reaction mixture was cooled to room temperature and diluted with 100 mL of $H_2O$. The resulting solution was extracted with 2×100 mL of ethyl acetate. The resulting mixture was washed with 2×100 ml of brine. The mixture was dried over anhydrous sodium sulfate and concentrated under vacuum. The residue was applied onto a silica gel column with ethyl acetate/petroleum ether (1:3). This resulted in 3.0 g (76.32%) of 2-(1-[[2-(trimethylsilyl)ethoxy]methyl] pyrrolo[2,3-b]pyridin-5-yl)acetonitrile as light yellow oil. LCMS (ES, m/z): M+1=288

Synthesis of methyl 2-bromo-4-(4-[[2-(4-chlorophenyl)-4,4-dimethylcyclohex-1-en-1-yl]methyl] piperazin-1-yl) benzoate: Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100° C. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS (ES, m/z): M+1=533, 531.

Synthesis of methyl 4-(4-[[2-(4-chlorophenyl)-4,4-dimethylcyclohex-1-en-1-yl]methyl]piperazin-1-yl)-2-[cyano(1-[[2-(trimethylsilyl)ethoxy]methyl]pyrrolo[2,3-b]pyridin-5-yl)methyl]benzoate: Into a 8-mL sealed tube purged and maintained with an inert atmosphere of nitrogen, was placed 2-(1-[[2-(trimethylsilyl) ethoxy]methyl]pyrrolo[2,3-b]pyridin-5-yl)acetonitrile (100.00 mg, 0.348 mmol, 1.00 equiv), dioxane (1.5 mL), methyl 2-bromo-4-(4-[[2-(4-chlorophenyl)-4,4-dimethylcyclohex-1-en-1-yl]methyl]piperazin-1-yl)benzoate (370.11 mg, 0.696 mmol, 2.00 equiv), t-BuOK (78.08 mg, 0.696 mmol, 2.0 equiv), X-Phos (66.34 mg, 0.139 mmol, 0.4 equiv), $Pd(OAC)_2$ (15.62 mg, 0.070 mmol, 0.2 equiv). The resulting solution was stirred for 16 h at 100° C. in an oil bath. The reaction was diluted with 5 mL of water. The resulting solution was extracted with 2×5 mL of ethyl acetate. The resulting mixture was washed with 2×5 ml of brine. The mixture was dried over anhydrous sodium sulfate and concentrated under vacuum. The residue was applied onto a silica gel column with ethyl acetate/petroleum ether (1:2). This reaction was repeated 26 times and obtained 1.0 g (14.99%) of methyl 4-(4-[[2-(4-chlorophenyl)-4,4-dimethylcyclohex-1-en-1-yl]methyl]piperazin-1-yl)-2-

[cyano(1-[[2-(trimethylsilyl)ethoxy]methyl]pyrrolo[2,3-b]pyridin-5-yl)methyl]benzoate as light yellow oil. LC-MS (ES, m/z): M+1=738.

Synthesis of 6-(4-[[2-(4-chlorophenyl)-4,4-dimethylcyclohex-1-en-1-yl]methyl]piperazin-1-yl)-4-(1-[[2-(trimethylsilyl)ethoxy]methyl]pyrrolo[2,3-b]pyridin-5-yl)-3,4-dihydro-2H-isoquinolin-1-one: Into a 100-mL 3-necked round-bottom flask purged and maintained with an inert atmosphere of nitrogen, was placed methyl 4-(4-[[2-(4-chlorophenyl)-4,4-dimethylcyclohex-1-en-1-yl]methyl]piperazin-1-yl)-2-[cyano(1-[[2-(trimethylsilyl)ethoxy]methyl] pyrrolo[2,3-b]pyridin-5-yl)methyl]benzoate (1.00 g, 1.354 mmol, 1.00 equiv), Toluene (6.00 mL), MeOH (18.00 mL), $CoCl_2 \cdot 6H_2O$ (0.64 g, 0.003 mmol, 2.0 equiv). This was followed by the addition of $NaBH_4$ (0.51 g, 0.014 mmol, 10 equiv) at 0° C. The resulting solution was stirred for 4 h at 0 degrees C. in an ice/salt bath. The reaction was then quenched by the addition of 50 mL water. The resulting solution was extracted with 2×50 mL of ethyl acetate. The resulting mixture was washed with 2×50 ml of brine. The mixture was dried over anhydrous sodium sulfate and concentrated under vacuum. The residue was applied onto a silica gel column with ethyl acetate/petroleum ether (EA). This resulted in 300 mg (31.18%) of 6-(4-[[2-(4-chlorophenyl)-4,4-dimethylcyclohex-1-en-1-yl]methyl]piperazin-1-yl)-4-(1-[[2-(trimethylsilyl)ethoxy]methyl]pyrrolo[2,3-b]pyridin-5-yl)-3,4-dihydro-2H-isoquinolin-1-one as yellow oil. LC-MS (ES, m/z): M+1=710

Synthesis of 6-(4-[[2-(4-chlorophenyl)-4,4-dimethylcyclohex-1-en-1-yl]methyl]piperazin-1-yl)-2-(4-fluoro-3-nitrobenzenesulfonyl)-4-(1-[[2-(trimethylsilyl)ethoxy]methyl]pyrrolo[2,3-b]pyridin-5-yl)-3,4-dihydroisoquinolin-1-one: Into a 8-mL sealed tube purged and maintained with an inert atmosphere of nitrogen, was placed 6-(4-[[2-(4-chlorophenyl)-4,4-dimethylcyclohex-1-en-1-yl]methyl]piperazin-1-yl)-4-(1-[[2-(trimethylsilyl)ethoxy]methyl]pyrrolo[2,3-b]pyridin-5-yl)-3,4-dihydro-2H-isoquinolin-1-one (10.00 mg, 0.014 mmol, 1.00 equiv), THF (0.50 mL). This was followed by the addition of NaH (1.01 mg, 0.042 mmol, 3.0 equiv) at 0° C. To this was added 4-fluoro-3-nitrobenzenesulfonyl chloride (6.75 mg, 0.028 mmol, 2.00 equiv) at 0° C. The resulting solution was stirred for 2 h at room temperature. The reaction was then quenched by the addition of 3 mL water. The resulting solution was extracted with 2×5 mL of ethyl acetate. The resulting mixture was washed with 2×5 ml of brine. The mixture was dried over anhydrous sodium sulfate and concentrated under vacuum. The residue was applied onto a silica gel column with ethyl acetate/petroleum ether (1:2). This reaction was repeated 20 times and obtained 110 mg (42.8%) of 6-(4-[[2-(4-chlorophenyl)-4,4-dimethylcyclohex-1-en-1-yl]methyl]piperazin-1-yl)-2-(4-fluoro-3-nitrobenzenesulfonyl)-4-(1-[[2-(trimethylsilyl)ethoxy]methyl]pyrrolo[2,3-b]pyridin-5-yl)-3,4-dihydroisoquinolin-1-one as a light yellow solid. LC-MS (ES, m/z): M+1=913.

Synthesis of 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-(1-[[2-(trimethylsilyl)ethoxy]methyl] pyrrolo[2,3-b]pyridin-5-yl)-3,4-dihydroisoquinolin-1-one: Into a 8-mL sealed tube, was placed 6-(4-[[2-(4-chlorophenyl)-4,4-dimethylcyclohex-1-en-1-yl]methyl]piperazin-1-yl)-2-(4-fluoro-3-nitrobenzenesulfonyl)-4-(1-[[2-(trimethylsilyl)ethoxy]methyl]pyrrolo[2,3-b]pyridin-5-yl)-3,4-dihydroisoquinolin-1-one (110.00 mg, 0.120 mmol, 1.00 equiv), ACN (2.0 mL), 1-[(2S)-1,4-dioxan-2-yl]methanamine hydrochloride (36.99 mg, 0.241 mmol, 2.00 equiv), $Cs_2CO_3$ (78.46 mg, 0.241 mmol, 2.0 equiv). The resulting solution was stirred for 2 h at room temperature. The resulting solution was diluted with 5 mL of $H_2O$. The resulting solution was extracted with 2×5 mL of ethyl acetate. The resulting solution was extracted with 2×5 mL of ethyl acetate. The resulting mixture was washed with 2×5 ml of brine. The mixture was dried over anhydrous sodium sulfate and concentrated under vacuum. The residue was applied onto a silica gel column with ethyl acetate/petroleum ether (4:1). This resulted in 90 mg (73.95%) of 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-(1-[[2-(trimethylsilyl)ethoxy]methyl]pyrrolo[2,3-b]pyridin-5-yl)-3,4-dihydroisoquinolin-1-one as a yellow solid. LC-MS (ES, m/z): M+1=1010.

Synthesis of 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-[1H-pyrrolo[2,3-b]pyridin-5-yl]-3,4-dihydroisoquinolin-1-one: Into a 8-mL sealed tube, was placed 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-(1-[[2-(trimethylsilyl)ethoxy]methyl] pyrrolo[2,3-b]pyridin-5-yl)-3,4-dihydroisoquinolin-1-one (30.00 mg, 0.030 mmol, 1.00 equiv), DCM (0.30 mL, 4.719 mmol, 158.99 equiv), TFA (0.10 mL, 1.346 mmol, 45.36 equiv), the resulting solution was stirred for 16 h at room temperature. The resulting mixture was concentrated under vacuum. The crude product was placed ACN (0.50 mL, 9.512 mmol, 320.48 equiv), ethylenediamine (5.35 mg, 0.089 mmol, 3.00 equiv). The resulting solution was stirred for 24 h at room temperature. The resulting mixture was concentrated under vacuum. The crude product was purified by Prep-HPLC with the following conditions: Column, XBridge Shield RP18 OBD Column, Sum, 19*150 mm; mobile phase, Water (0.05% $NH_3 \cdot H_2O$) and ACN (80% Phase B up to 90% in 7 min); Detector, UV 254/220 nm. This resulted in 8 mg (30.61%) of 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-[1H-pyrrolo[2,3-b]pyridin-5-yl]-3,4-dihydroisoquinolin-1-one as a yellow solid. LC-MS: (ES, m/z): M+1: 880. $^1H$ NMR (300 MHz, DMSO-$d_6$, ppm) δ 11.62 (s, 1H), 8.55 (s, 1H), 8.32 (s, 1H), 8.14 (s, 1H), 7.76 (d, J=8.4 Hz, 1H), 7.43 (s, 1H), 7.36-7.20 (m, 4H), 7.05 (d, J=7.81 Hz, 2H), 6.94 (d, J=8.49 Hz, 1H), 6.78-6.70 (m, 1H), 6.66 (s, 1H), 6.26 (s, 1H), 4.52 (d, J=19.6 Hz, 2H), 4.23 (d, J=12.4 Hz, 1H), 3.79 (d, J=7.05 Hz, 3H), 3.69-3.59 (m, 2H), 3.54-3.42 (m, 2H), 3.25-3.22 (m, 4H), 2.74 (s, 3H), 2.19 (s, 7H), 1.97 (s, 2H), 1.40 (s, 2H), 0.94 (s, 6H).

Example 3: Preparation of 2-(1-(1H-pyrrolo[2,3-b]pyridin-5-yl)vinyl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide Into a 8-mL sealed tube, was placed 6-(4-[[2-(4-chlorophenyl)-4,4-dimethylcyclohex-1-en-1-yl]methyl]piperazin-1-yl)-2-(4-[[(2S)-1,4-dioxan-2-ylmethyl]amino]-3-nitrobenzenesulfonyl)-4-(1-[[2-(trimethylsilyl)ethoxy]methyl]pyrrolo[2,3-b]pyridin-5-yl)-3,4-dihydroisoquinolin-1-one (60.00 mg, 0.059 mmol, 1.00 equiv), ethylenediamine (7.14 mg, 0.119 mmol, 2.00 equiv), TBAF (1M in THF, 2 mL). The resulting solution was stirred for 16 h at 50° C. in an oil bath. The resulting solution was diluted with 5 mL of $H_2O$. The resulting solution was extracted with 2×5 mL of ethyl acetate The resulting mixture was washed with 2×5 ml of brine. The mixture was dried over anhydrous sodium sulfate and concentrated under vacuum. The crude product was purified by Prep-HPLC with the following conditions: Column, XBridge Shield RP18 OBD Column, Sum, 19*150 mm; mobile phase, Water (0.05% $NH_3 \cdot H_2O$) and ACN (25% Phase B up to 45% in 8 min); Detector, UV 254/220 nm. This resulted in 10 mg (19.13%) of (S)—N-((4-(((1,4-dioxan-2-yl)methyl)amino)-3-nitrophenyl)sulfonyl)-2-(1-(1H-pyrrolo[2,3-b]pyridin-5-yl)vinyl)-4-(4-((4'-chloro-5,5-dimethyl-3,4,5,6-tetrahydro-[1,1'-biphenyl]-2-yl)methyl) piperazin-1-yl)benzamide as a yellow solid. LC-MS (ES, m/z): M+1: 880. $^1H$ NMR (300 MHz, DMSO-$d_6$, ppm) δ: 11.31 (s, 1H), 8.50 (s, 1H), 8.26 (d, J=2.1 Hz, 1H), 7.96 (s, 1H), 7.46 (s, 2H), 7.37 (d, J=8.0 Hz, 2H), 7.31-7.29 (m, 1H), 7.08 (d, J=8.1 Hz, 2H), 6.94 (d, J=8.6 Hz, 1H), 6.91 (d, J=8.7 Hz, 1H), 6.72 (d, J=1.8 Hz, 1H), 6.21 (s, 1H), 5.47 (s, 1H), 5.04 (s, 1H), 3.87-3.80 (m, 3H), 3.71-3.63 (m, 2H), 3.56-3.44 (m, 2H), 3.24-3.17 (m, 8H), 2.77 (d, J=20.0 Hz, 2H), 2.29 (s, 4H), 2.20 (s, 2H), 1.99 (s, 2H), 1.42 (t, J=5.24 Hz, 2H), 0.96 (s, 6H).

Example 4: Preparation of N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide Synthesis of tert-butyl 2-(2-bromophenyl)pyrrolidine-1-carboxylate: Into a 250-mL 3-necked round-bottom flask, was placed 2-(2-bromophenyl)pyrrolidine (4.50 g, 19.901 mmol, 1.00 equiv), DCM (60 mL), TEA (4.03 g, 39.802 mmol, 2.0 equiv), DMAP (0.24 g, 1.990 mmol, 0.1 equiv). This was followed by the addition of $Boc_2O$ (8.69 g, 39.817 mmol, 2.00 equiv) at 0° C. The resulting solution was stirred for overnight at room temperature. The resulting mixture was concentrated under vacuum. The residue was applied onto a silica gel column with ethyl acetate/petroleum ether (1:5). This resulted in 4.8 g (Y=73.93%) of tert-butyl 2-(2-bromophenyl)pyrrolidine-1-carboxylate as light yellow oil. LC-MS: (ES, m/z): M-$CH_3$+1=311.

Synthesis of tert-butyl 2-(2-cyclopropylphenyl)pyrrolidine-1-carboxylate: Into a 250-mL round-bottom flask purged and maintained with an inert atmosphere of nitrogen, was placed tert-butyl 2-(2-bromophenyl)pyrrolidine-1-carboxylate (4.80 g, 14.713 mmol, 1.00 equiv), dioxane (54.00 mL), $H_2O$ (6.00 mL), cyclopropylboronic acid (3.79 g, 44.140 mmol, 3.00 equiv), $K_2CO_3$ (6.10 g, 44.137 mmol, 3.00 equiv), $Pd(PPh_3)_4$ (1.70 g, 1.471 mmol, 0.10 equiv). The resulting solution was stirred for overnight at 90° C. in an oil bath. The solids were filtered out and the reaction was quenched with 100 mL water. The resulting solution was extracted with 2×100 mL of ethyl acetate. The resulting mixture was washed with 2×100 ml of brine. The mixture was dried over anhydrous sodium sulfate and concentrated under vacuum. The residue was applied onto a silica gel column with ethyl acetate/petroleum ether (1:5). This resulted in 3.8 g (Y=89.86%) of tert-butyl 2-(2-cyclopropylphenyl)pyrrolidine-1-carboxylate as light yellow oil. LC-MS: (ES, m/z): M-$CH_3$+1=273. $^1H$ NMR (300 MHz, DMSO-d6, ppm) δ 7.17-7.09 (m, 2H), 7.00 (d, J=8.1 Hz, 2H), 5.30 (s, 1H), 3.59 (dt, J=10.4, 6.1 Hz, 1H), 3.48 (dt, J=10.7, 7.4 Hz, 1H), 2.43-2.23 (m, 1H), 1.93 (d, J=6.1 Hz, 1H), 1.83 (q, J=6.8 Hz, 2H), 1.72-1.62 (m, 1H), 1.08 (s, 9H), 0.98-0.89 (m, 2H), 0.71-0.52 (m, 2H).

Synthesis of 2-(2-cyclopropylphenyl)pyrrolidine: Into a 100-mL round-bottom flask, was placed tert-butyl 2-(2-cyclopropylphenyl) pyrrolidine-1-carboxylate (3.80 g, 13.222 mmol, 1.00 equiv), DCM (50.00 mL), TFA (5.00 mL). The resulting solution was stirred for 16 h at room temperature. The resulting mixture was concentrated under vacuum.

The resulting solution was extracted with 50 mL of ethyl acetate (discard) and the aqueous layers combined. The pH value of the solution was adjusted to $NaHCO_3$(aq) with 7-8. The resulting solution was extracted with 2×100 mL of dichloromethane and the organic layers combined. The resulting mixture was washed with 2×100 ml of brine. The mixture was dried over anhydrous sodium sulfate and concentrated under vacuum. This resulted in 2.1 g crude of 2-(2-cyclopropylphenyl)pyrrolidine as brown oil. LC-MS: (ES, m/z): M+1=188 Synthesis of tert-butyl 2-[2-(2-cyclopropylphenyl)pyrrolidin-1-yl]-7-azaspiro[3.5]nonane-7-carboxylate: Into a 100-mL round-bottom flask, was placed 2-(2-cyclopropylphenyl)pyrrolidine (2.10 g, 11.213 mmol, 1.00 equiv), DCM (30.00 mL), tert-butyl 2-oxo-7-azaspiro[3.5]nonane-7-carboxylate (2.68 g, 11.199 mmol, 1.00 equiv), $NaBH(OAc)_3$ (4.75 g, 22.426 mmol, 2.0 equiv). The resulting solution was stirred for 2 h at room temperature. The reaction was then quenched by the addition of 50 mL of water. The resulting solution was extracted with 2×100 mL of dichloromethane. The resulting mixture was washed with 2×100 ml of brine. The mixture was dried over anhydrous sodium sulfate and concentrated under vacuum. The residue was applied onto a silica gel column with ethyl acetate/petroleum ether (1:2). This resulted in 4.0 g (Y=86.88%) of tert-butyl 2-[2-(2-cyclopropylphenyl)pyrrolidin-1-yl]-7-azaspiro[3.5]nonane-7-carboxylate as light yellow oil. LC-MS: (ES, m/z): M+1=411.

Synthesis of 2-[2-(2-cyclopropylphenyl)pyrrolidin-1-yl]-7-azaspiro[3.5]nonane: Into a 100-mL round-bottom flask, was placed tert-butyl 2-[2-(2-cyclopropylphenyl)pyrrolidin-1-yl]-7-azaspiro[3.5]nonane-7-carboxylate (2.00 g, 4.871 mmol, 1.00 equiv), DCM (20.00 mL), TFA (4.00 mL). The resulting solution was stirred for 4 h at room temperature. The resulting mixture was concentrated. The resulting solution was diluted with 20 mL of water. The pH value of the solution was adjusted to 10-11 with NaOH (1 mol/L). The resulting solution was extracted with 2×50 mL of dichloromethane and the organic layers combined and dried over anhydrous sodium sulfate and concentrated. This resulted in 1.2 g crude of 2-[2-(2-cyclopropylphenyl)pyrrolidin-1-yl]-7-azaspiro[3.5]nonane as yellow oil. LC-MS: (ES, m/z): M+1=311

Synthesis of methyl 2-bromo-4-[2-[2-(2-cyclopropylphenyl)pyrrolidin-1-yl]-7-azaspiro[3.5] nonan-7-yl]benzoate: Into a 50-mL round-bottom flask, was placed 2-[2-(2-cyclopropylphenyl)pyrrolidin-1-yl]-7-azaspiro[3.5]nonane (1.20 g, 3.865 mmol, 1.00 equiv), DMF (15.00 mL), methyl 2-bromo-4-fluorobenzoate (1.80 g, 0.008 mmol, 2.00 equiv), $Na_2CO_3$ (0.82 g, 0.008 mmol, 2.0 equiv). The resulting solution was stirred for 4 h at 105° C. in an oil bath. The resulting solution was diluted with 30 mL of $H_2O$. The resulting solution was extracted with 2×50 mL of ethyl acetate. The resulting mixture was washed with 2×50 ml of brine. The mixture was dried over anhydrous sodium sulfate and concentrated under vacuum. The residue was applied onto a silica gel column with ethyl acetate/petroleum ether (1:1). This resulted in 1.1 g (Y=54.37%) of methyl 2-bromo-4-[2-[2-(2-cyclopropylphenyl) pyrrolidin-1-yl]-7-azaspiro[3.5]nonan-7-yl] benzoate as light yellow oil. LC-MS: (ES, m/z): M+1=523.

Synthesis of methyl 4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoate: Into a 40-mL sealed tube purged and maintained with an inert atmosphere of nitrogen, was placed methyl 2-bromo-4-[2-[2-(2-cyclopropylphenyl)pyrrolidin-1-yl]-7-azaspiro[3.5]nonan-7-yl]benzoate (300.00 mg, 0.573 mmol, 1.00 equiv), dioxane (3.00 mL), 7-((2-(trimethylsilyl)ethoxy)methyl)-1,3,4,7-tetrahydro-2H-pyrrolo[3',2':5,6]pyrido[2,3-b][1,4]oxazepine (219.69 mg, 0.688 mmol, 1.20 equiv), $Cs_2CO_3$ (373.42 mg, 1.146 mmol, 2.0 equiv), X-antphos Pd G2 (50.83 mg, 0.057 mmol, 0.1 equiv). The resulting solution was stirred for 2 h at 100° C. in an oil bath. The solids were filtered out. The resulting solution was diluted with 15 mL of $H_2O$. The resulting solution was extracted with 2×20 mL of ethyl acetate. The resulting mixture was washed with 2×20 ml of brine. The mixture was dried over anhydrous sodium sulfate and concentrated under vacuum. The residue was applied onto a silica gel column with ethyl acetate/petroleum ether (1:1). This resulted in 150 mg (Y=34.35%) of methyl 4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoate as a light yellow solid. LC-MS: (ES, m/z): M+1=762. $^1H$ NMR (300 MHz, DMSO-$d_6$, ppm) δ 7.66 (dd, J=5.2, 3.8 Hz, 1H), 7.46 (d, J=9.2 Hz, 1H), 7.35-7.30 (m, 3H), 7.13-7.07 (m, 1H), 7.04 (s, 1H), 6.58 (d, J=7.6 Hz, 2H), 6.23 (d, J=3.5 Hz, 1H), 5.45 (s, 2H), 5.08-5.02 (m, 2H), 4.41 (t, J=5.1 Hz, 2H), 4.03-3.92 (m, 1H), 3.52-3.45 (m, 5H), 3.36 (s, 3H), 3.18 (s, 2H), 3.07 (s, 2H), 2.23-2.05 (m, 7H), 1.97 (s, 2H), 1.65-1.33 (m, 6H), 1.00 (dd, J=9.1, 6.5 Hz, 2H), 0.87-0.78 (m, 2H), 0.69 (d, J=5.4 Hz, 2H), −0.08 (s, 9H).

Synthesis of 4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl) benzoic acid Into a 8-mL sealed tube, was placed methyl 4-(2-(2-(2-cyclopropylphenyl) pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoate (150.00 mg, 0.197 mmol, 1.00 equiv), MeOH (1.00 mL), THF (1.00 mL), $H_2O$ (1.00 mL) The resulting solution was stirred for 36 h at 70° C. in an oil bath. The resulting mixture was concentrated. The resulting solution was diluted with 5 mL of $H_2O$. The pH value of the solution was adjusted to 3-4 with HCl (1 mol/L). The solids were collected by filtration. This resulted in 120 mg crude of 4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoic acid as a light yellow solid. LC-MS: (ES, m/z): M+1=748.

Synthesis of N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzamide: Into a 8-mL sealed tube, was placed 4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzoic acid (120.00 mg, 0.160 mmol, 1.00 equiv), DCM (3.00 mL), 4-[[(2S)-1,4-dioxan-2-ylmethyl]amino]-3-nitrobenzenesulfonamide (61.08 mg, 0.192 mmol, 1.20 equiv), EDC.HCl (36.90 mg, 0.192 mmol, 1.2 equiv), DMAP (39.20 mg, 0.321 mmol, 2 equiv). The resulting solution was stirred for 48 h at 35° C. in an oil bath. The resulting mixture was concentrated under vacuum. The residue was applied onto a silica gel column with dichloromethane/methanol (10:1). This resulted in 60 mg (Y=35.71%) of N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzamide as a light yellow solid. LC-MS: (ES, m/z): M+1=1047.

Synthesis of N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide hydrochloride: Into a 8-mL sealed tube, was placed N-((4-((((S)-1,4-dioxan-2-yl)methyl)amino)-3-nitrophenyl)sulfonyl)-4-(2-(2-(2-cyclopropylphenyl) pyrrolidin-1-yl)-7-azaspiro[3.5]nonan-7-yl)-2-(7-((2-(trimethylsilyl)ethoxy)methyl)-3,4-dihydro-2H-pyrrolo[3',2':5,6]pyrido[2,3-b][1,4]oxazepin-1(7H)-yl)benzamide (60.00 mg, 0.057 mmol, 1.00 equiv), THF (2.00 mL), ethylenediamine (34.43 mg, 0.573 mmol, 10.00 equiv), TBAF (1M in THF, 0.3 mL). The resulting solution was stirred for 48 h at 80° C. in an oil bath. The resulting mixture was concentrated under vacuum. The crude product was purified by Prep-HPLC with the following conditions: Column, Sunfire C18 OBD; mobile phase, Water (0.1% HCl) and ACN (32% Phase B up to 48% in 7 min); Detector, UV 254/220 nm. This resulted in 4 mg (Y=7.61%) of N-((4-((((S)-1,4-dioxan-2-yl)methyl)amino)-3-nitrophenyl)sulfonyl)-4-(2-(2-(2-cyclopropylphenyl)pyrrolidin-1-yl)-7-azaspiro[3.5]nonan-7-yl)-2-(3,4-dihydro-2H-pyrrolo[3',2':5,6]pyrido[2,3-b][1,4]oxazepin-1(7H)-yl)benzamide hydrochloride as a light yellow solid. LC-MS: (ES, m/z): M+1=917. $^1H$ NMR (300 MHz, Methanol-$d_4$, ppm) δ 8.57 (d, J=2.2 Hz, 1H), 7.75 (dd, J=9.2, 2.3 Hz, 1H), 7.68 (dd, J=5.6, 3.4 Hz, 1H), 7.47 (d, J=8.7 Hz, 1H), 7.37 (dd, J=5.8, 3.3 Hz, 2H), 7.32 (s, 1H), 7.21 (dd, J=3.7, 1.7 Hz, 1H), 7.19-7.17 (m, 1H), 6.96-6.91 (m, 1H), 6.83 (d, J=8.7 Hz, 1H), 6.26 (d, J=3.5 Hz, 1H), 5.21-5.16 (m, 1H), 4.64 (s, 2H), 4.05-4.00 (m, 1H), 3.91-3.82 (m, 5H), 3.81 (d, J=2.3 Hz, 1H), 3.77 (d, J=2.9 Hz, 1H), 3.72 (s, 1H), 3.65 (dd, J=11.0, 2.9 Hz, 1H), 3.60 (d, J=2.9 Hz, 1H), 3.57-3.52 (m, 1H), 3.51-3.45 (m, 1H), 3.45-3.40 (m, 1H), 3.38 (dd, J=6.9, 3.1 Hz, 4H), 2.67-2.57 (m, 1H), 2.40-2.28 (m, 3H), 2.22 (d, J=8.1 Hz, 4H), 2.10 (s, 1H), 1.83-1.74 (m, 4H), 1.69 (d, J=6.2 Hz, 2H), 1.56-1.43 (m, 1H), 1.30 (s, 1H), 1.09 (d, J=8.2 Hz, 2H), 0.73 (dd, J=20.1, 5.5 Hz, 2H).

Example 5: Preparation of 4-[2-[2-(2-cyclopropylphenyl)pyrrolidin-1-yl]-7-azaspiro[3.5]nonan-7-yl]-2-[(12R)-12-methyl-13-oxa-2,4,10-triazatricyclo[7.4.0.0^[3,7]]trideca-1(9),2,5,7-tetraen-10-yl]-N-[3-nitro-4-[(oxan-4-ylmethyl)amino]benzenesulfonyl]benzamide Synthesis of 2-bromo-4-[2-[2-(2-cyclopropylphenyl)pyrrolidin-1-yl]-7-azaspiro[3.5]nonan-7-yl] benzoic acid: Into a 50-mL round-bottom flask, was placed methyl 2-bromo-4-[2-[2-(2-cyclopropylphenyl)pyrrolidin-1-yl]-7-azaspiro[3.5]nonan-7-yl]benzoate (300.00 mg, 0.573 mmol, 1.00 equiv), MeOH (2.00 mL), THF (2.00 mL), $H_2O$ (2.00 mL), NaOH (91.68 mg, 2.292 mmol, 4.00 equiv). The resulting solution was stirred for 36 h at 60° C. in an oil bath. The resulting mixture was concentrated under vacuum. The resulting solution was diluted with 15 mL of $H_2O$. The pH value of the solution was adjusted to 3-4 with HCl (1 mol/L). The solids were collected by filtration. This resulted in 220 mg crude of 2-bromo-4-[2-[2-(2-cyclopropylphenyl) pyrrolidin-1-yl]-7-azaspiro[3.5] nonan-7-yl]benzoic acid as a brown solid. LC-MS: (ES, m/z): M+1=509

Synthesis of 2-bromo-4-[2-[2-(2-cyclopropylphenyl)pyrrolidin-1-yl]-7-azaspiro[3.5]nonan-7-yl]-N-[3-nitro-4-[(oxan-4-ylmethyl)amino]benzenesulfonyl]benzamide: Into a 40-mL sealed tube, was placed 2-bromo-4-[2-[2-(2-cyclopropylphenyl)pyrrolidin-1-yl]-7-azaspiro[3.5]nonan-7-yl] benzoic acid (220.00 mg, 0.432 mmol, 1.00 equiv), DMF (5 mL), 3-nitro-4-[(oxan-4-ylmethyl)amino]benzenesulfonamide (163.40 mg, 0.518 mmol, 1.20 equiv), EDC.HCl (99.33 mg, 0.518 mmol, 1.2 equiv), DMAP (105.51 mg, 0.864 mmol, 2.0 equiv). The resulting solution was stirred for overnight at room temperature. The resulting mixture was concentrated under vacuum. The residue was applied onto a silica gel column with dichloromethane/methanol (10:1). This resulted in 200 mg (Y=57.41%) of 2-bromo-4-[2-[2-(2-cyclopropylphenyl)pyrrolidin-1-yl]-7-azaspiro[3.5]nonan-7-yl]-N-[3-nitro-4-[(oxan-4-ylmethyl)amino] benzenesulfonyl]benzamide as a yellow solid. LC-MS: (ES, m/z): M+1=806

Synthesis of 4-[2-[2-(2-cyclopropylphenyl)pyrrolidin-1-yl]-7-azaspiro[3.5]nonan-7-yl]-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]-N-[3-nitro-4-[(oxan-4-ylmethyl)amino]benzenesulfonyl]benzamide: Into a 40-mL sealed tube purged and maintained with an inert atmosphere of nitrogen, was placed 2-bromo-4-[2-[2-(2-cyclopropylphenyl)pyrrolidin-1-yl]-7-azaspiro[3.5]nonan-7-yl]-N-[3-nitro-4-[(oxan-4-ylmethyl)amino]benzenesulfonyl]benzamide (200.00 mg, 0.248 mmol, 1.00 equiv), DMF (3.00 mL), (12R)-12-methyl-4-[[2-(trimethylsilyl)ethoxy]methyl]-13-oxa-2,4,10-triazatricyclo[7.4.0.0^[3,7]]trideca-1(9),2,5,7-tetraene (79.19 mg, 0.248 mmol, 1.00 equiv), $Cs_2CO_3$ (161.53 mg, 0.496 mmol, 2.0 equiv), CuI (23.61 mg, 0.124 mmol, 0.5 equiv), $N^1$,$N^2$-bis(4-hydroxy-2,6-dimethylphenyl)oxalamide (40.70 mg, 0.124 mmol, 0.5 equiv). The resulting solution was stirred for 1 h at 100° C. in an oil bath. The solids were filtered out. The reaction was then quenched by the addition of 20 mL of water. The resulting solution was extracted with 2×30 mL of ethyl acetate. The resulting mixture was washed with 2×30 ml of brine. The mixture was dried over anhydrous sodium sulfate and concentrated under vacuum. The residue was applied onto a silica gel column with ethyl acetate/petroleum ether (EA). This resulted in 120 mg (Y=46.31%) of 4-[2-[2-(2-cyclopropylphenyl)pyrrolidin-1-yl]-7-azaspiro[3.5]nonan-7-yl]-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]-N-[3-nitro-4-[(oxan-4-ylmethyl)amino]benzenesulfonyl]benzamide as a yellow solid. LC-MS: (ES, m/z): M+1=1045

Synthesis of 4-[2-[2-(2-cyclopropylphenyl)pyrrolidin-1-yl]-7-azaspiro[3.5]nonan-7-yl]-2-[(12R)-12-methyl-13-oxa-2,4,10-triazatricyclo[7.4.0.0^[3,7]]trideca-1(9),2,5,7-tetraen-10-yl]-N-[3-nitro-4-[(oxan-4-ylmethyl)amino] benzenesulfonyl]benzamide: Into a 50-mL round-bottom flask, was placed 4-[2-[2-(2-cyclopropylphenyl)pyrrolidin-1-yl]-7-azaspiro[3.5]nonan-7-yl]-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]-N-[3-nitro-4-[(oxan-4-ylmethyl)amino]benzenesulfonyl] benzamide (80.00 mg, 0.077 mmol, 1.00 equiv), THF (3 mL), ethylenediamine (45.99 mg, 0.765 mmol, 10.00 equiv), TBAF (1M in THF, 0.4 mL).

The resulting solution was stirred for 48 h at 80° C. in an oil bath. The resulting mixture was concentrated under vacuum. The crude product was purified by Prep-HPLC with the following conditions: Column, XBridge Shield RP18 OBD Column, Sum, 19*150 mm; mobile phase, Water (0.05% $NH_3 \cdot H_2O$) and ACN (44% Phase B up to 70% in 8 min); Detector, UV 254/220 nm. This resulted in 8 mg (Y=11.42%) of 4-[2-[2-(2-cyclopropylphenyl)pyrrolidin-1-yl]-7-azaspiro[3.5]nonan-7-yl]-2-[(12R)-12-methyl-13-oxa-2,4,10-triazatricyclo[7.4.0.0^[3,7]]trideca-1(9),2,5,7-tetraen-10-yl]-N-[3-nitro-4-[(oxan-4-ylmethyl)amino] benzenesulfonyl]benzamide as a yellow solid. LC-MS: (ES, m/z): M+1=915, $^1H$ NMR (300 MHz, Methanol-$d_4$, ppm) δ 8.54 (s, 1H), 8.40 (s, 1H), 7.63-7.50 (m, 2H), 7.31-7.22 (m, 3H), 7.11-7.08 (m, 1H), 6.96 (d, J=3.4 Hz, 1H), 6.78 (d, J=8.9 Hz, 2H), 6.66 (d, J=2.0 Hz, 2H), 5.97 (s, 1H), 4.63-4.54 (m, 1H), 4.00 (dd, J=11.6, 3.1 Hz, 2H), 3.56-3.43 (m, 5H), 3.29-3.25 (m, 2H), 3.14 (d, J=28.4 Hz, 5H), 2.46 (s, 1H), 2.14-1.91 (m, 7H), 1.76 (d, J=13.2 Hz, 2H), 1.63-1.50 (m, 3H), 1.45-1.38 (m, 9H), 1.02 (d, J=8.6 Hz, 2H), 0.69-0.66 (m, 2H).

Synthesis of tert-butyl 2-(2-bromophenyl) pyrrolidine-1-carboxylate: Into a 250-mL 3-necked round-bottom flask, was placed 2-(2-bromophenyl)pyrrolidine (4.50 g, 19.901 mmol, 1.00 equiv), DCM (60 mL), TEA (4.03 g, 39.802 mmol, 2.0 equiv), DMAP (0.24 g, 1.990 mmol, 0.1 equiv). This was followed by the addition of $Boc_2O$ (8.69 g, 39.817 mmol, 2.00 equiv) at 0° C. The resulting solution was stirred for overnight at room temperature. The resulting mixture was concentrated under vacuum. The residue was applied onto a silica gel column with ethyl acetate/petroleum ether (1:5). This resulted in 4.8 g (Y=73.93%) of tert-butyl 2-(2-bromophenyl) pyrrolidine-1-carboxylate as light yellow oil. LC-MS: (ES, m/z): M-t-Bu+MeCN+1=311, 313.

Synthesis of tert-butyl 2-(2-cyclopropylphenyl)pyrrolidine-1-carboxylate: Into a 250-mL round-bottom flask purged and maintained with an inert atmosphere of nitrogen, was placed tert-butyl 2-(2-bromophenyl)pyrrolidine-1-carboxylate (4.80 g, 14.713 mmol, 1.00 equiv), dioxane (54.00 mL), $H_2O$ (6.00 mL), cyclopropylboronic acid (3.79 g, 44.140 mmol, 3.00 equiv), $K_2CO_3$ (6.10 g, 44.137 mmol, 3.00 equiv), $Pd(PPh_3)_4$ (1.70 g, 1.471 mmol, 0.10 equiv). The resulting solution was stirred for overnight at 90° C. in an oil bath. The solids were filtered out and the reaction was quenched with 100 mL water. The resulting solution was extracted with 2×100 mL of ethyl acetate. The resulting mixture was washed with 2×100 ml of brine. The mixture was dried over anhydrous sodium sulfate and concentrated under vacuum. The residue was applied onto a silica gel column with ethyl acetate/petroleum ether (1:5). This resulted in 3.8 g (Y=89.86%) of tert-butyl 2-(2-cyclopropylphenyl)pyrrolidine-1-carboxylate as light yellow oil. LC-MS: (ES, m/z): M-t-Bu+MeCN+1=273, $^1H$ NMR (300 MHz, DMSO-$d_6$, ppm) δ 7.17-7.09 (m, 2H), 7.00 (d, J=8.1 Hz, 2H), 5.30 (s, 1H), 3.59 (dt, J=10.4, 6.1 Hz, 1H), 3.48 (dt, J=10.7, 7.4 Hz, 1H), 2.43-2.23 (m, 1H), 1.93 (d, J=6.1 Hz, 1H), 1.83 (q, J=6.8 Hz, 2H), 1.72-1.62 (m, 1H), 1.08 (s, 9H), 0.98-0.89 (m, 2H), 0.71-0.52 (m, 2H).

Synthesis of 2-(2-cyclopropylphenyl)pyrrolidine: Into a 100-mL round-bottom flask, was placed tert-butyl 2-(2-cyclopropylphenyl) pyrrolidine-1-carboxylate (3.80 g, 13.222 mmol, 1.00 equiv), DCM (50.00 mL), TFA (5.00 mL). The resulting solution was stirred for 16 h at room temperature. The resulting mixture was concentrated under vacuum. The resulting solution was extracted with 50 mL of ethyl acetate (discard) and the aqueous layers combined. The pH value of the solution was adjusted to $NaHCO_3$(aq) with 7-8. The resulting solution was extracted with 2×100 mL of dichloromethane and the organic layers combined. The resulting mixture was washed with 2×100 ml of brine. The mixture was dried over anhydrous sodium sulfate and concentrated under vacuum. This resulted in 2.1 g crude of 2-(2-cyclopropylphenyl)pyrrolidine as brown oil. LC-MS: (ES, m/z): M+1=188.

Synthesis of tert-butyl 2-[2-(2-cyclopropylphenyl)pyrrolidin-1-yl]-7-azaspiro[3.5]nonane-7-carboxylate: Into a 100-mL round-bottom flask, was placed 2-(2-cyclopropylphenyl)pyrrolidine (2.10 g, 11.213 mmol, 1.00 equiv), DCM (30.00 mL), tert-butyl 2-oxo-7-azaspiro[3.5]nonane-7-carboxylate (2.68 g, 11.199 mmol, 1.00 equiv), NaBH$(OAc)_3$ (4.75 g, 22.426 mmol, 2.0 equiv). The resulting solution was stirred for 2 h at room temperature. The reaction was then quenched by the addition of 50 mL of water. The resulting solution was extracted with 2×100 mL of dichloromethane. The resulting mixture was washed with 2×100 ml of brine. The mixture was dried over anhydrous sodium sulfate and concentrated under vacuum. The residue was applied onto a silica gel column with ethyl acetate/petroleum ether (1:2). This resulted in 4.0 g (Y=86.88%) of tert-butyl 2-[2-(2-cyclopropylphenyl) pyrrolidin-1-yl]-7-azaspiro[3.5]nonane-7-carboxylate as light yellow oil. LC-MS: (ES, m/z): M+1=411

Synthesis of 2-[2-(2-cyclopropylphenyl) pyrrolidin-1-yl]-7-azaspiro[3.5]nonane: Into a 100-mL round-bottom flask, was placed tert-butyl 2-[2-(2-cyclopropylphenyl)pyrrolidin-1-yl]-7-azaspiro[3.5]nonane-7-carboxylate (2.00 g, 4.871 mmol, 1.00 equiv), DCM (20.00 mL), TFA (4.00 mL). The resulting solution was stirred for 4 h at room temperature. The resulting mixture was concentrated. The resulting solution was diluted with 20 mL of water. The pH value of the solution was adjusted to 10-11 with NaOH (1 mol/L). The resulting solution was extracted with 2×50 mL of dichloromethane and the organic layers combined and dried over anhydrous sodium sulfate and concentrated. This resulted in 1.2 g crude of 2-[2-(2-cyclopropylphenyl) pyrrolidin-1-yl]-7-azaspiro[3.5]nonane as yellow oil. LC-MS: (ES, m/z): M+1=311.

Synthesis of methyl 2-bromo-4-[2-[2-(2-cyclopropylphenyl)pyrrolidin-1-yl]-7-azaspiro[3.5] nonan-7-yl]benzoate: Into a 50-mL round-bottom flask, was placed 2-[2-(2-cyclopropylphenyl)pyrrolidin-1-yl]-7-azaspiro[3.5]nonane (1.20 g, 3.865 mmol, 1.00 equiv), DMF (15.00 mL), methyl 2-bromo-4-fluorobenzoate (1.80 g, 0.008 mmol, 2.00 equiv), $Na_2CO_3$ (0.82 g, 0.008 mmol, 2.0 equiv). The resulting solution was stirred for 4 h at 105° C. in an oil bath. The resulting solution was diluted with 30 mL of $H_2O$. The resulting solution was extracted with 2×50 mL of ethyl acetate. The resulting mixture was washed with 2×50 ml of brine. The mixture was dried over anhydrous sodium sulfate and concentrated under vacuum. The residue was applied onto a silica gel column with ethyl acetate/petroleum ether (1:1). This resulted in 1.1 g (Y=54.37%) of methyl 2-bromo-4-[2-[2-(2-cyclopropylphenyl) pyrrolidin-1-yl]-7-azaspiro[3.5] nonan-7-yl]benzoate as light yellow oil. LC-MS: (ES, m/z): M+1=523.

Synthesis of (E)-2-(2-ethoxyvinyl)-4,4,5,5-tetramethyl-1,3,2-dioxaborolane Into a 3 L 4-necked round-bottom flask, was placed ethyl vinyl ether (1000.00 g, 13.9 mol, 3.50 equiv), 4,4,5,5-tetramethyl-1,3,2-dioxaborolane (508.00 g, 3.97 mol, 1.00 equiv). This solution was cooled to 5 degrees C. in an ice/salt bath. This followed by the addition of $Pd(OAc)_2$ (50.00 g, 222 mmol, 0.02 equiv) in portions at 5 degrees C. The resulting solution was stirred for 18 h at room temperature. The resulting solution was diluted with 5 L of PE. The resulting mixture was concentrated. This resulted in 1100 g (crude, Y=50%) of 2-[(E)-2-ethoxyethenyl]-4,4,5,5-tetramethyl-1,3-dioxolane as light yellow oil. LC-MS-1: M+1=199, H-NMR-1 (300 MHz, DMSO-$d_6$, ppm): δ 6.91-6.95 (m, 1H), 4.30-4.34 (m, 1H), 3.78-3.82 (m, 2H), 1.14-1.24 (m, 15H).

Synthesis of N-[(2R)-2-hydroxypropyl]acetamide Into a 250-mL 3-necked round-bottom flask purged and maintained with an inert atmosphere of nitrogen, was placed (2R)-1-aminopropan-2-ol (100 g, 1.3 mol, 1 equiv), DCM (1 L), TEA (160 g, 1.6 mol, 1.2 equiv). This was followed by the addition of a solution of acetyl acetate (136 g, 1.3 mol, 1.0 equiv) in 100 ml (DCM) dropwise with stirring at 0-10° C. The resulting solution was stirred for 14 hr at room temperature. The resulting mixture was concentrated. The residue was applied onto a silica gel column with dichloromethane/methanol (100:5). This resulted in 250 g (crude) of N-[(2R)-2-hydroxypropyl]acetamide as a yellow oil. H-NMR-2: (300 MHz, $CDCl_3$-d, ppm): δ 6.02 (s, 1H), 3.88-3.98 (m, 1H), 3.41-3.49 (m, 1H), 3.08-3.15 (m, 2H), 2.06 (s, 3H).

Synthesis of 5-bromo-6-fluoropyridin-2-amine Into a 50 L 4-necked round-bottom flask, was placed 6-fluoropyridin-2-amine (4500.00 g, 40.178 mol, 1.00 equiv), ACN (20.00 L). This was followed by the addition of NBS (7035.17 g, 41.383 mol, 1.03 equiv) in portions at R.T degrees C. The resulting solution was stirred for 3 h at room temperature. The resulting solution was diluted with 40 L of water. The resulting solution was extracted with 2×36 L of ethyl acetate. The resulting mixture was washed with 10 L of brine. The mixture was dried over anhydrous sodium sulfate and concentrated. The resulting mixture was washed with 3×9 L of PE. This mixture was dried by oven to give product 7634 g (Y=90%) of 5-bromo-6-fluoropyridin-2-amine as a light brown solid. LC-MS-3: M+1=191

Synthesis of 5-bromo-6-fluoro-3-iodopyridin-2-amine Into a 50 L 4-necked round-bottom flask, was placed 5-bromo-6-fluoropyridin-2-amine (7000.00 g, 36.842 mol, 1.00 equiv), AcOH (34.00 L). The solution was cooled to 10 degree C. in a water/ice bath. This was followed by the addition of NIS (8290 g, 36.8 mol, 1.00 equiv) in portions at 10 degrees C. The resulting solution was stirred for 3 h at room temperature. The resulting solution was diluted with 100 L of water. The mixture was filtrated, collection of filter cake and the filter cake was washed by water (35 L×2) and dried by oven to give product 9840 g (Y=90%) of 5-bromo-6-fluoro-3-iodopyridin-2-amine as a brown solid. LC-MS-4: M+1=317

Synthesis of 5-bromo-3-(2-ethoxyvinyl)-6-fluoropyridin-2-amine Into a 20 L 4-necked round-bottom flask purged and maintained with an inert atmosphere of nitrogen, was placed 5-bromo-6-fluoro-3-iodopyridin-2-amine (855.00 g, 2705.696 mmol, 1.00 equiv), i-PrOH (10000.00 mL), 2-[(E)-2-ethoxyethenyl]-4,4,5,5-tetramethyl-1,3-dioxolane (1000.00 g, 5050.505 mmol, 1.87 equiv), $K_3PO_4$ (1720.00 g, 8113.207 mmol, 3.00 equiv), Ruphos (12.00 g, 27.060 mmol, 0.02 equiv), $Pd(OAc)_2$ (20.00 g, 88 mmol, 0.02 equiv). The resulting solution was stirred for 12 h at room temperature. The solids were filtered out. The filter cake was washed by 3×2 L DCM. The organic layer was collected and concentrated. The residue was applied onto a silica gel column and eluted with ethyl acetate/petroleum ether (1:5). This concentrated and resulted in 680 g (80%) of 5-bromo-3-[(E, Z)-2-ethoxyethenyl]-6-fluoropyridin-2-amine (Z, E mixtures) as dark brown oil. LC-MS-5: M+1=261, 263

Synthesis of 5-bromo-6-fluoro-1H-pyrrolo[2,3-b] pyridine Into a 10 L 4-necked round-bottom flask purged and maintained with an inert atmosphere of nitrogen, was placed 5-bromo-3-[(E)-2-ethoxyethenyl]-6-fluoropyridin-2-amine (680.00 g, 2605.364 mmol, 1.00 equiv), EtOH (5000.00 mL), HCl (1000.00 mL). The resulting solution was stirred for 5 h at room temperature. The resulting mixture was concentrated. The pH value of the solution was adjusted to 6 with NaOH (4 mol/L). The solids were collected by filtration and washed with 3×500 mL water. This resulted in 560 g (Q-NMR=70%) of 5-bromo-6-fluoro-1H-pyrrolo[2,3-b] pyridine as a light brown solid. LC-MS-6: M+1=215, 217

Synthesis of 5-bromo-6-fluoro-1-((2-(trimethylsilyl) ethoxy) methyl)-1H-pyrrolo[2,3-b]pyridine Into a 10 L 4-necked round-bottom flask was placed 5-bromo-6-fluoro-1H-pyrrolo[2,3-b] pyridine (560.00 g, 2.6 mol, 1.00 equiv), DMF (5000.00 mL). This solution was cooled to 0 degrees C. in a water/ice bath. This was followed by the addition of NaH (156 g, 3.9 mol, 1.5 equiv) in portions at 0 degrees C. To this was added SEM-Cl (561 g, 3.38 mol, 1.3 equiv) dropwise with stirring at 0 degrees C. The resulting solution was stirred for 1 h at room temperature. The reaction was then quenched by the addition of 2000 mL of water/ice. The resulting solution was diluted with 5 L of water. The resulting solution was extracted with 2×10 L of ethyl acetate and the organic layers combined. The resulting mixture was washed with 3×5 L of water. The resulting mixture was washed with 3 L of brine. The mixture was dried over anhydrous sodium sulfate and concentrated. The residue was applied onto a silica gel column and eluted with ethyl acetate/petroleum ether (1:20). This resulted in 550 g (87%) of 5-bromo-6-fluoro-1-[[2-(trimethylsilyl) ethoxy] methyl] pyrrolo[2,3-b] pyridine as light yellow oil. LC-MS-7: M+1=345, 347

Synthesis of (R)—N-(2-(5-bromo-1-((2-(trimethylsilyl) ethoxy)methyl)-1H-pyrrolo[2,3-b] pyidin-6-yloxy)propyl) acetamide Into a 50-mL round-bottom flask, was placed N-[(2R)-2-hydroxypropyl] acetamide (crude, 81.6 g, 697 mmol, 3.00 equiv), dioxane (800 ml).

This was followed by the addition of NaH (28 g, 697 mmol, 3 equiv), in portions at 5° C.-15° C. The resulting solution was stirred for 30 min at RT. To this was added a solution of 5-bromo-6-fluoro-1-((2-(trimethylsilyl) ethoxy) methyl)-1H-pyrrolo[2,3-b] pyridine (80 g, 232 mmol, 1 equiv) in dioxane (100 ml). The resulting solution was stirred for 4 hr at 80° C. in an oil bath. The reaction was then quenched by the addition of 50 ml of water at 10° C. The resulting solution was concentrated and diluted with 500 ml $H_2O$. The resulting solution was extracted with 3×500 ml of ethyl acetate. The resulting mixture was washed with 1×300 ml of NaCl (aq). The mixture was dried over anhydrous sodium sulfate and concentrated. The residue was applied onto a silica gel column with PE/EA (100:20). This resulted in 40 g (pure) and 30 g (70%) of (R)—N-(2-(5-bromo-1-((2-(trimethylsilyl) ethoxy) methyl)-1H-pyrrolo[2,3-b] pyridin-6-yloxy) propyl) acetamide as a yellow oil. LC-MS-8: M+1=442, 444

Synthesis of 1-[(12R)-4-(trimethylsilyl) ethoxy) methyl)-12-methyl-13-oxa-2, 4, 10-triazatricyclo[7.4.0.0^[3,7]]trideca-1(9),2,5,7-tetraen-10-yl]ethan-1-one Into a 1 L round-bottom flask purged and maintained with an inert atmosphere of nitrogen, was placed (R)—N-(2-(5-bromo-1-((2-(trimethylsilyl)ethoxy)methyl)-1H-pyrrolo[2,3-b]pyridin-6-yloxy) propyl) acetamide (40 g, 90.7 mmol, 1 equiv), dioxane (500 mL), $Cs_2CO_3$ (88 g, 272 mmol, 3 equiv), BrettPhos Pd G3 (4.1 g, 4.5 mmol, 0.05 equiv). The mixture was stirred for 14 h at 80 degrees C. under $N_2$. The resulting solution was cooled to R.T in ice-water and concentrated. The mixture was diluted with 300 ml $H_2O$. The resulting solution was extracted with 3×300 ml of ethyl acetate. The resulting mixture was washed with 1×200 mL of NaCl (aq). The mixture was dried over anhydrous sodium sulfate and concentrated. The residue was applied onto a silica gel column with ethyl acetate/petroleum ether (2:5). This resulted in 33 g (crude, 70%) of 1-[(12R)-4-(trimethylsilyl) ethoxy)methyl)-12-methyl-13-oxa-2,4,10-triazatricyclo [7.4.0.0^[3,7]] trideca-1(9),2,5,7-tetraen-10-yl]ethan-1-one as brown oil. H-NMR-9: (300 MHz, $CDCl_3$-d, ppm) δ 7.23 (s, 1H), 6.47 (s, 1H), 5.60 (s, 1H), 4.55-4.59 (m, 2H), 3.51-3.59 (m, 2H), 2.37 (s, 3H), 1.50 (s, 3H), 0.89-0.94 (m, 2H), 0.01 (s, 9H).

Synthesis of (12R)-4-(trimethylsilyl)ethoxy)methyl)-12-methyl-13-oxa-2,4,10-triazatricyclo[7.4.0.0^[3,7]]trideca-1(9),2,5,7-tetraene Into a 1-L round-bottom flask, was placed 1-[(12R)-4-(trimethylsilyl)ethoxy) methyl)-12-methyl-13-oxa-2,4,10-triazatricyclo[7.4.0.0 [3,7]] trideca-1(9),2,5,7-tetraen-10-yl]ethan-1-one (33 g), methanol (300 mL), sodium hydroxide (2M, 300 ml). The resulting solution was stirred for 14 h at 80° C. in an oil bath. The resulting solution was concentrated (MeOH) and extracted with 3×200 ml of ethyl acetate. The resulting mixture was washed with 1×200 mL of NaCl (aq). The mixture was dried over anhydrous sodium sulfate and concentrated. The residue was applied onto a silica gel column with ethyl acetate/petroleum ether (1:1). This resulted in 16.2 g of (12R)-4-(trimethylsilyl) ethoxy)methyl)-12-methyl-13-oxa-2,4,10-triazatricyclo [7.4.0.0 [3,7]]trideca-1(9),2,5,7-tetraene as brown oil. LC-MS-10: M+1=320.

Example 6: Preparation of 2-[(11R,15S)-13,16-dioxa-2,4,10-triazatetracyclo[7.7.0.0^[3,7]0.0^[11,15]] hexadeca-1(9),2,5,7-tetraen-10-yl]-4-[2-[(2S)-2-(2-isopropylphenyl)pyrrolidin-1-yl]-7-azaspiro[3.5] nonan-7-yl]-N-[3-nitro-4-[(oxan-4-ylmethyl)amino] benzenesulfonyl]benzamide (assumed) and 2-[(11S,15R)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-[(oxan-4-ylmethyl)amino]benzenesulfonyl]benzamide (assumed)

Synthesis of N-[(trans)-4-hydroxyoxolan-3-yl]-4-methylbenzenesulfonamide: Into a 250-mL round-bottom flask purged and maintained with an inert atmosphere of nitrogen, was placed 3,6-dioxabicyclo[3.1.0]hexane (5.00 g, 58.079 mmol, 1.00 equiv), dioxane (100.00 mL), p-toluenesulfonamide (11.93 g, 69.681 mmol, 1.20 equiv), TEBAC (1.33 g, 5.833 mmol, 0.10 equiv), $K_2CO_3$ (0.80 g, 5.788 mmol, 0.10 equiv). The resulting solution was stirred for 3 days at 90 degrees C. in an oil bath. The reaction mixture was cooled to room temperature. The solids were filtered out. The resulting mixture was concentrated under vacuum. The residue was applied onto a silica gel column with ethyl acetate/petroleum ether (2:1). This resulted in 10.69 g (25.75%) of N-[(trans)-4-hydroxyoxolan-3-yl]-4-methylbenzenesulfonamide as a white solid. LC-MS: (ES, m/z): M+1=258.

Synthesis of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide: Into a 250-mL round-bottom flask purged and maintained with an inert atmosphere of nitrogen, was placed N-[(trans)-4-hydroxyoxolan-3-yl]-4-methylbenzenesulfonamide (10.50 g, 14.691 mmol, 1.30 equiv, 36%), THF (100 mL). This was followed by the addition of NaH (2.71 g, 67.756 mmol, 6.01 equiv, 60%), in portions at 0 degrees C. The resulting solution was stirred for 30 min at 0 degrees C. To this was added 5-bromo-6-fluoro-1-[[2-(trimethylsilyl)ethoxy]

methyl]pyrrolo[2,3-b]pyridine (3.89 g, 11.266 mmol, 1.00 equiv) at 0 degrees C. The resulting solution was stirred for 4 hr at 70 degrees C. in an oil bath. The reaction mixture was cooled to room temperature. The reaction was then quenched by the addition of 500 mL of aqueous $NH_4Cl$. The resulting solution was extracted with 3×300 mL of ethyl acetate and the organic layers combined. The resulting mixture was washed with 1×1500 mL of brine. The mixture was dried over anhydrous sodium sulfate and concentrated under vacuum. The residue was applied onto a silica gel column with ethyl acetate/petroleum ether (1:2). This resulted in 3 g (45.71%) of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide as light yellow oil. $^1$H NMR (300 MHz, Chloroform-d, ppm) δ 8.04 (s, 1H), 7.78-7.61 (m, 2H), 7.25-7.10 (m, 3H), 6.43 (d, J=3.6 Hz, 1H), 5.67 (d, J=10.8 Hz, 1H), 5.60 (d, J=5.7 Hz, 1H), 5.49 (d, J=10.8 Hz, 1H), 5.40 (dt, J=6.1, 3.1 Hz, 1H), 4.27 (dd, J=10.5, 5.9 Hz, 1H), 4.21-4.03 (m, 1H), 4.03-3.86 (m, 2H), 3.70-3.52 (m, 3H), 2.32 (s, 3H), 0.93 (ddt, J=10.6, 5.5, 2.6 Hz, 2H), −0.02 (s, 9H).

Synthesis of (trans)-10-(4-methylbenzenesulfonyl)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene: Into a 250-mL round-bottom flask purged and maintained with an inert atmosphere of nitrogen, was placed N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide (3.00 g, 5.149 mmol, 1.00 equiv), DMF (50.00 mL), phen (743.00 mg, 4.123 mmol, 0.80 equiv), CuI (785.00 mg, 4.122 mmol, 0.80 equiv), $K_2CO_3$ (2.14 g, 15.484 mmol, 3.01 equiv). The resulting solution was stirred for 2 days at 120 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 mL of brine. The mixture was dried over anhydrous sodium sulfate and concentrated under vacuum. The residue was applied onto a silica gel column with ethyl acetate/petroleum ether (1:2). This resulted in 2.5 g (82.26%) of (trans)-10-(4-methylbenzenesulfonyl)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraene as yellow oil. LC-MS: (ES, m/z) M+1=502.

Synthesis of (11S,15R)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) and (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed): Into a 100-mL round-bottom flask, was placed Mg (2.04 g, 83.933 mmol, 19.81 equiv), MeOH (30.00 mL), (trans)(11R,15S)-10-(4-methylbenzenesulfonyl)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (2.50 g, 4.236 mmol, 1.00 equiv, 85%). The resulting solution was stirred for 2 hr at 60 degrees C. in an oil bath. The reaction mixture was cooled to room temperature. The resulting solution was diluted with 300/300 mL of $NaHCO_3$ and $CH_2Cl_2$. The solids were filtered out and the organic was separated. The mixture was dried over anhydrous sodium sulfate and concentrated under vacuum. The residue was applied onto a silica gel column with ethyl acetate/petroleum ether (1:3). The crude product was purified by Chiral-Prep-HPLC with the following conditions: Mobile phase: A: n-Hexane (0.1% DEA) B:ETOH; Flow rate: 20 mL/min; Column: DAICEL CHIRALPAK IA, 250*20 mm, Sum; Gradient: 12% B in 20 min; 220 nm. This resulted in 350 mg (23.78%) of (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) as yellow oil. and 400 mg (27.18%) of (11S,15R)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraene (assumed) as yellow oil. Peak 1: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H). Peak 2: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H).

Synthesis of (S)—N-[(2-bromophenyl)methylidene]-2-methylpropane-2-sulfinamide: Into a 3000-mL round-bottom flask, was placed 2-bromo-benzaldehyde (120.00 g, 648.579 mmol, 1.00 equiv), THF (2000.00 mL), (S)-2-methylpropane-2-sulfinamide (79.00 g, 651.815 mmol, 1.00 equiv), $Ti(OEt)_4$ (297.00 g, 1302.009 mmol, 2.01 equiv). The resulting solution was stirred overnight at 55 degrees C. in an oil bath. The reaction mixture was cooled to room temperature. The resulting mixture was concentrated under vacuum. The resulting solution was diluted with 2000/2000 mL of $H_2O$ and EtOAc. The solids were filtered out. The organic layer was separated from the filtration. The mixture was dried over anhydrous sodium sulfate and concentrated under vacuum. This resulted in 181 g (96.83%) of (S)—N-[(2-bromophenyl)methylidene]-2-methylpropane-2-sulfinamide as yellow oil. LC-MS: (ES, m/z): M+1: 288; H-NMR (300 MHz, DMSO-$d_6$, ppm) δ 8.81 (d, J=1.7 Hz, 1H), 8.03 (dt, J=6.6, 1.7 Hz, 1H), 7.84-7.74 (m, 1H), 7.54 (dp, J=5.6, 3.7, 2.4 Hz, 2H), 1.19 (d, J=1.7 Hz, 9H).

Synthesis of (S)—N-[(1S)-1-(2-bromophenyl)-3-(1,3-dioxan-2-yl)propyl]-2-methylpropane-2-sulfinamide: Into a 1000-mL 3-necked round-bottom flask purged and maintained with an inert atmosphere of nitrogen, was placed Mg (37.13 g, 1527.669 mmol, 3.97 equiv), $I_2$ (9.82 g, 38.691 mmol, 0.10 equiv), THF (300.00 mL), the resulting solution was warmed to 65 degrees C., followed by the addition of 2-(2-bromoethyl)-1,3-dioxane (30.00 g, 153.8020 mmol, 0.4 equiv) in THF (50 mL) at 65 degrees C. After addition completed, the mixture was cooled to room temperature, another 2-(2-bromoethyl)-1,3-dioxane (270.00 g, 1384.615 mmol, 3.6 equiv) in THF (150 mL) was added. Another 3000-mL 3-necked round-bottom flask purged and maintained with an inert atmosphere of nitrogen, was placed a solution of (S)—N-[(2-bromophenyl)methylidene]-2-methylpropane-2-sulfinamide (111.00 g, 385.149 mmol, 1.00 equiv) in DCM (800 mL). The above solution was added dropwise at −40 degrees C. The resulting solution was stirred for 1 hr at −40 degrees C. in a liquid nitrogen bath. The reaction was then quenched by the addition of 2000 mL of aqueous $NH_4Cl$. The resulting solution was extracted with 3×1000 mL of dichloromethane and the organic layers combined. The resulting mixture was washed with 1×3000 ml of brine. The mixture was dried over anhydrous sodium sulfate and concentrated under vacuum. This resulted in 150 g (96.32%) of (S)—N-[(1S)-1-(2-bromophenyl)-3-(1,3-dioxan-2-yl)propyl]-2-methylpropane-2-sulfinamide as yellow oil. LC-MS: (ES, m/z): M+1: 404

Synthesis of (2S)-2-(2-bromophenyl)pyrrolidine: Into a 2000-mL round-bottom flask, was placed (S)—N-[(1S)-1-(2-bromophenyl)-3-(1,3-dioxan-2-yl)propyl]-2-methylpropane-2-sulfinamide (150.00 g, 370.957 mmol, 1.00 equiv), TFA (360.00 mL), $H_2O$ (90 mL), the resulting solution was stirred for 1 h at room temperature. TFA (1350.00 mL), triethylsilane (129.40 g, 1112.841 mmol, 3.00 equiv) was added. The resulting solution was stirred overnight at room temperature. The resulting mixture was concentrated. The resulting solution was diluted with 2000 mL of $H_2O$. The resulting solution was extracted with 2×500 mL of MTBE and the organic layers combined. The resulting mixture was washed with 1×1000 ml of HCl (2 mol/L). The pH value of the aqueous was adjusted to 13 with NaOH (4 mol/L). The resulting solution was extracted with 3×500 mL of dichloromethane and the organic layers combined and dried over anhydrous sodium sulfate and concentrated. This resulted in 40 g (47.69%) of (2S)-2-(2-bromophenyl)pyrrolidine as yellow oil. Its optically pure enantiomer was recrystallized by dibenzoyl-L-taratric acid salt in EA. LC-MS: (ES, m/z): M+1:226; H-NMR (300 MHz, DMSO-$d_6$, ppm) δ 7.67 (dd, J=7.8, 1.8 Hz, 1H), 7.53 (dd, J=7.9, 1.3 Hz, 1H), 7.34 (td, J=7.5, 1.3 Hz, 1H), 7.13 (td, J=7.6, 1.8 Hz, 1H), 4.33 (t, J=7.4 Hz, 1H), 3.10-2.87 (m, 2H), 2.35-2.18 (m, 1H), 1.80-1.64 (m, 2H), 1.40-1.20 (m, 1H).

Synthesis of tert-butyl 2-[(2S)-2-(2-bromophenyl)pyrrolidin-1-yl]-7-azaspiro[3.5]nonane-7-carboxylate: Into a 250-mL round-bottom flask, was placed (2S)-2-(2-bromophenyl)pyrrolidine (6.18 g, 27.331 mmol, 1.00 equiv), DCM (100.00 mL), tert-butyl 2-oxo-7-azaspiro[3.5]nonane-7-carboxylate (6.56 g, 27.412 mmol, 1.00 equiv), NaBH$(OAc)_3$ (11.65 g, 54.968 mmol, 2.01 equiv). The resulting solution was stirred for 2 hr at room temperature. The resulting mixture was concentrated under vacuum. The residue was applied onto a silica gel column with ethyl acetate/petroleum ether (1:1). This resulted in 7.9 g (64.31%) of tert-butyl 2-[(2S)-2-(2-bromophenyl)pyrrolidin-1-yl]-7-azaspiro[3.5]nonane-7-carboxylate as yellow oil. LC-MS: (ES, m/z): M+1:449

Synthesis of tert-butyl 2-[(2S)-2-[2-(prop-1-en-2-yl)phenyl]pyrrolidin-1-yl]-7-azaspiro[3.5]nonane-7-carboxylate: Into a 250-mL round-bottom flask purged and maintained with an inert atmosphere of nitrogen, was placed tert-butyl 2-[(2S)-2-(2-bromophenyl)pyrrolidin-1-yl]-7-azaspiro[3.5]nonane-7-carboxylate (7.15 g, 15.909 mmol, 1.00 equiv), dioxane (72.00 mL), $H_2O$ (8.00 mL), 4,4,5,5-tetramethyl-2-(prop-1-en-2-yl)-1,3,2-dioxaborolane (6.39 g, 38.027 mmol, 2.39 equiv), $K_2CO_3$ (6.61 g, 47.827 mmol, 3.01 equiv), Pd(dppf)$Cl_2$·$CH_2Cl_2$ (1.30 g, 1.596 mmol, 0.10 equiv). The resulting solution was stirred overnight at 80 degrees C. in an oil bath. The reaction mixture was cooled to room temperature. The resulting mixture was concentrated under vacuum. The residue was applied onto a silica gel column with ethyl acetate/petroleum ether (1:2). This resulted in 4.34 g (66.44%) of tert-butyl 2-[(2S)-2-[2-(prop-1-en-2-yl)phenyl]pyrrolidin-1-yl]-7-azaspiro[3.5]nonane-7-carboxylate as yellow oil. LC-MS: (ES, m/z): M+1:411

Synthesis of tert-butyl 2-[(2S)-2-(2-isopropylphenyl)pyrrolidin-1-yl]-7-azaspiro[3.5]nonane-7-carboxylate: Into a 100-mL pressure tank reactor (10 atm), was placed tert-butyl 2-[(2S)-2-[2-(prop-1-en-2-yl)phenyl]pyrrolidin-1-yl]-7-azaspiro[3.5]nonane-7-carboxylate (3.58 g, 8.719 mmol, 1.00 equiv), EtOH (50.00 mL), 10% Pd/C (500.00 mg, 4.698 mmol, 0.54 equiv), to the above $H_2$ was introduced in. The resulting solution was stirred overnight at 50 degrees C. in an oil bath. The solids were filtered out. The resulting mixture was concentrated under vacuum. The residue was applied onto a silica gel column with ethyl acetate/petroleum ether (1:2). This resulted in 2.6 g (72.27%) of tert-butyl 2-[(2S)-2-(2-isopropylphenyl)pyrrolidin-1-yl]-7-azaspiro[3.5]nonane-7-carboxylate as yellow oil. LC-MS: (ES, m/z): M+1:413

Synthesis of 2-[(2S)-2-(2-isopropylphenyl)pyrrolidin-1-yl]-7-azaspiro[3.5]nonane hydrochloride: Into a 100-mL round-bottom flask, was placed tert-butyl 2-[(2S)-2-(2-isopropylphenyl)pyrrolidin-1-yl]-7-azaspiro[3.5]nonane-7-carboxylate (2.60 g, 6.301 mmol, 1.00 equiv), HCl(gas) in 1,4-dioxane (20.00 mL). The resulting solution was stirred for 1 hr at room temperature. The resulting mixture was concentrated under vacuum. This resulted in 2.1 g (95.50%) of 2-[(2S)-2-(2-isopropylphenyl)pyrrolidin-1-yl]-7-azaspiro[3.5]nonane hydrochloride as a red solid. LC-MS: (ES, m/z): M+1:313

Synthesis of methyl 2-bromo-4-[2-[(2S)-2-(2-isopropylphenyl)pyrrolidin-1-yl]-7-azaspiro[3.5]nonan-7-yl]benzoate: Into a 100-mL round-bottom flask, was placed 2-[(2S)-2-(2-isopropylphenyl)pyrrolidin-1-yl]-7-azaspiro[3.5]nonane hydrochloride (1.32 g, 3.783 mmol, 1.00 equiv), DMSO (20.00 mL), methyl 2-bromo-4-fluorobenzoate (1.76 g, 7.552 mmol, 2.00 equiv), $Na_2CO_3$ (1.61 g, 15.190 mmol, 4.02 equiv). The resulting solution was stirred for 7 hr at 110 degrees C. in an oil bath. The reaction mixture was cooled to room temperature. The resulting solution was diluted with 200 mL of water. The resulting solution was extracted with 3×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with ethyl acetate/petroleum ether (1:2). This resulted in 1.05 g (52.82%) of methyl 2-bromo-4-[2-[(2S)-2-(2-isopropylphenyl)pyrrolidin-1-yl]-7-azaspiro[3.5]nonan-7-yl]benzoate as yellow oil. LC-MS: (ES, m/z): M+1:579; H-NMR (300 MHz, Chloroform-d, ppm) δ 7.80 (d, J=8.9 Hz, 1H), 7.64 (d, J=7.4 Hz, 1H), 7.27-7.14 (m, 3H), 7.06 (d, J=2.6 Hz, 1H), 6.73 (dd, J=9.0, 2.4 Hz, 1H), 3.87 (s, 3H), 3.68 (t, J=8.0 Hz, 1H), 3.34 (dq, J=13.7, 6.8, 6.1 Hz, 1H), 3.28-3.04 (m, 6H), 2.39 (q, J=8.8 Hz, 1H), 2.22 (dt, J=19.5, 8.2 Hz, 1H), 1.88 (dq, J=31.2, 10.5, 10.1 Hz, 4H), 1.75-1.42 (m, 6H), 1.26 (t, J=7.0 Hz, 6H).

Synthesis of methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraen-10-yl]benzoate (assumed): Into a 40-mL vial purged and maintained with an inert atmosphere of nitrogen, was placed methyl 2-bromo-4-[2-[(2S)-2-(2-isopropylphenyl)pyrrolidin-1-yl]-7-azaspiro[3.5]nonan-7-yl]benzoate (770.00 mg, 1.465 mmol, 1.70 equiv), toluene (10.00 mL), (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) (300.00 mg, 0.863 mmol, 1.00 equiv), $Cs_2CO_3$ (843.00 mg, 2.587 mmol, 3.00 equiv), Xantphos (100.00 mg, 0.173 mmol, 0.20 equiv), $Pd_2(dba)_3$·$CHCl_3$ (89.00 mg, 0.086 mmol, 0.10 equiv). The resulting solution was stirred for 5 hr at 100 degrees C. in an oil bath. The reaction mixture was cooled to room temperature. The resulting mixture was concentrated under vacuum. The residue was applied onto a silica gel column with ethyl acetate/petroleum ether (1:1). This resulted in 600 mg (87.74%) of methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraen-10-yl]benzoate (assumed) as a yellow solid. LC-MS: (ES, m/z): M+1:792

Synthesis of methyl 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed): Into a 40-mL vial, was placed methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0^[3,7]0.0^[11,15]] hexadeca-1(9),2,5,7-tetraen-10-yl]benzoate (assumed) (600.00 mg, 0.757 mmol, 1.00 equiv), TBAF in THF (10.00 mL), ethylenediamine (910.00 mg, 15.141 mmol, 19.99 equiv). The resulting solution was stirred for 8 hr at 70 degrees C. in an oil bath. The reaction mixture was cooled to room temperature. The resulting solution was diluted with 200 mL of water. The resulting solution was extracted with 2×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with ethyl acetate/petroleum ether (2:1). This resulted in 300 mg (59.84%) of methyl 2-[(11R,15S)-13,16-dioxa-2,4,10-triazatetracyclo[7.7.0.0 [3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl] benzoate (assumed) as a yellow solid. LC-MS: (ES, m/z): M+1:662

Synthesis of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed): Into a 100-mL round-bottom flask, was placed methyl 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed) (300.00 mg, 0.453 mmol, 1.00 equiv), MeOH (5.00 mL), dioxane (5.00 mL), NaOH (2.00 mL). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 2×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with dichloromethane/methanol (10:1). This resulted in 240 mg (81.73%) of 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) as a yellow solid. LC-MS: (ES, m/z): M+1:648

Synthesis of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-[(oxan-4-ylmethyl)amino]benzenesulfonyl]benzamide (assumed): Into a 40-mL vial, was placed 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) (80.00 mg, 0.123 mmol, 1.00 equiv), DCM (5.00 mL), 3-nitro-4-[(oxan-4-ylmethyl)amino]benzenesulfonamide (39.00 mg, 0.124 mmol, 1.00 equiv), EDCI (47.00 mg, 0.245 mmol, 1.99 equiv), DMAP (60.00 mg, 0.491 mmol, 3.98 equiv). The resulting solution was stirred overnight at 30 degrees C. The resulting mixture was concentrated under vacuum. The residue was applied onto a silica gel column with dichloromethane/methanol (10:1). The crude product was purified by Prep-HPLC with the following conditions (2 #SHIMADZU (HPLC-01)): Column, XBridge Shield RP18 OBD Column, 19*150 mm, Sum; mobile phase, Water (0.05% $NH_3 \cdot H_2O$) and ACN (44% Phase B up to 53% in 7 min); Detector, UV. This resulted in 15 mg (12.85%) of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-[(oxan-4-ylmethyl)amino]benzenesulfonyl]benzamide (assumed) as a yellow solid. LC-MS: (ES, m/z): M+1:945; H-NMR (300 MHz, DMSO-$d_6$, ppm) δ 12.30 (s, 1H), 11.10 (d, J=55.7 Hz, 1H), 8.51 (s, 1H), 8.31 (d, J=2.3 Hz, 1H), 7.55 (s, 2H), 7.44-7.02 (m, 5H), 6.93-6.61 (m, 3H), 6.57 (s, 1H), 6.02 (ddd, J=13.3, 3.4, 1.8 Hz, 1H), 4.62 (s, 1H), 4.46 (q, J=8.4 Hz, 1H), 4.29 (s, 1H), 4.09 (t, J=7.2 Hz, 1H), 3.85 (t, J=11.4 Hz, 4H), 3.70-3.38 (m, 3H), 3.30-2.94 (m, 9H), 2.28 (d, J=2.0 Hz, 2H), 2.07-1.01 (m, 21H).

Synthesis of methyl 4-[2-[(2S)-2-(2-isopropylphenyl)pyrrolidin-1-yl]-7-azaspiro[3.5]nonan-7-yl]-2-[(11S,15R)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraen-10-yl]benzoate (assumed): Into a 40-mL vial purged and maintained with an inert atmosphere of nitrogen, was placed methyl 2-bromo-4-[2-[(2S)-2-(2-isopropylphenyl)pyrrolidin-1-yl]-7-azaspiro[3.5]nonan-7-yl]benzoate (257.00 mg, 0.489 mmol, 1.70 equiv), toluene (5.00 mL), (11S,15R)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) (100.00 mg, 0.288 mmol, 1.00 equiv), $Cs_2CO_3$ (281.00 mg, 0.862 mmol, 3.00 equiv), Xantphos (33.00 mg, 0.057 mmol, 0.20 equiv), $Pd_2(dba)_3 \cdot CHCl_3$ (30.00 mg, 0.029 mmol, 0.10 equiv). The resulting solution was stirred for 5 hr at 100 degrees C. in an oil bath. The reaction mixture was cooled to room temperature. The resulting mixture was concentrated under vacuum. The residue was applied onto a silica gel column with ethyl acetate/petroleum ether (1:1). This resulted in 220 mg (96.51%) of methyl 4-[2-[(2S)-2-(2-isopropylphenyl)pyrrolidin-1-yl]-7-azaspiro[3.5]nonan-7-yl]-2-[(11S,15R)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraen-10-yl]benzoate (assumed) as yellow oil. LC-MS: (ES, m/z): M+1:792

Synthesis of methyl 2-[(11S,15R)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed): Into a 40-mL vial, was placed methyl 4-[2-[(2S)-2-(2-isopropylphenyl)pyrrolidin-1-yl]-7-azaspiro[3.5]nonan-7-yl]-2-[(11S,15R)-4-[[2-(trimethylsilyl)ethoxy]methyl]-13,16-dioxa-2,4,10-triazatetracyclo[7.7.0.0^[3,7]0.0^[11,15]] hexadeca-1(9),2,5,7-tetraen-10-yl]benzoate (assumed) (220.00 mg, 0.278 mmol, 1.00 equiv), TBAF in THF (10.00 mL), ethylenediamine (334.01 mg, 5.563 mmol, 20.01 equiv). The resulting solution was stirred for 8 hr at 70 degrees C. in an oil bath. The reaction mixture was cooled to room temperature. The resulting solution was diluted with 200 mL of water. The resulting solution was extracted with 2×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with ethyl acetate/petroleum ether (2:1). This resulted in 100 mg (54.40%) of methyl 2-[(11S,15R)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl] benzoate (assumed) as a yellow solid. LC-MS: (ES, m/z): M+1:662

Synthesis of 2-[(11S,15R)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed): Into a 40-mL vial, was placed methyl 2-[(11S,15R)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed) (100.00 mg, 0.151 mmol, 1.00 equiv), MeOH (5.00 mL), dioxane (5.00 mL), NaOH (4N, 2.00 mL). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 3×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with dichloromethane/methanol (10:1). This resulted in 90 mg (91.95%) of 2-[(11S,15R)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) as a light yellow solid. LC-MS: (ES, m/z): M+1:648

Synthesis of 2-[(11S,15R)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-[(oxan-4-ylmethyl)amino]benzenesulfonyl]benzamide (assumed): Into a 40-mL vial, was placed 2-[(11S,15R)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) (90.00 mg, 0.139 mmol, 1.00 equiv), DCM (5.00 mL), 3-nitro-4-[(oxan-4-ylmethyl)amino]benzenesulfonamide (44.00 mg, 0.140 mmol, 1.00 equiv), EDCI (53.00 mg, 0.276 mmol, 1.99 equiv), DMAP (68.00 mg, 0.557 mmol, 4.01 equiv). The resulting solution was stirred overnight at 30 degrees C. The resulting mixture was concentrated under vacuum. The residue was applied onto a silica gel column with dichloromethane/methanol (10:1). The crude product was purified by Prep-HPLC with the following conditions (2 #SHIMADZU (HPLC-01)): Column, XBridge Shield RP18 OBD Column, 19*150 mm, Sum; mobile phase, Water (0.05% $NH_3 \cdot H_2O$) and ACN (44% Phase B up to 54% in 7 min); Detector, UV. This resulted in 40 mg (30.46%) of 2-[(11S,15R)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-[(oxan-4-ylmethyl)amino]benzenesulfonyl]benzamide (assumed) as a yellow solid. LC-MS: (ES, m/z): M+1:945; H-NMR (300 MHz, DMSO-$d_6$, ppm) δ 12.30 (s, 1H), 11.10 (d, J=55.7 Hz, 1H), 8.51 (s, 1H), 8.31 (d, J=2.3 Hz, 1H), 7.55 (s, 2H), 7.44-7.02 (m, 5H), 6.93-6.61 (m, 3H), 6.57 (s, 1H), 6.02 (ddd, J=13.3, 3.4, 1.8 Hz, 1H), 4.62 (s, 1H), 4.46 (q, J=8.4 Hz, 1H), 4.29 (s, 1H), 4.09 (t, J=7.2 Hz, 1H), 3.85 (t, J=11.4 Hz, 4H), 3.70-3.38 (m, 3H), 3.30-2.94 (m, 9H), 2.28 (d, J=2.0 Hz, 2H), 2.07-1.01 (m, 21H).

Example 7: Preparation of 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1r,4r)-4-hydroxy-4-methylcyclohexyl]methyl]amino)benzenesulfonyl]benzamide (assumed) and 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1s,4s)-4-hydroxy-4-methylcyclohexyl]methyl]amino)benzenesulfonyl]benzamide (assumed)

Synthesis of N-[(trans)-4-hydroxyoxolan-3-yl]-4-methylbenzenesulfonamide: Into a 250-mL round-bottom flask purged and maintained with an inert atmosphere of nitrogen, was placed 3,6-dioxabicyclo[3.1.0]hexane (5.00 g, 58.079 mmol, 1.00 equiv), dioxane (100.00 mL), p-toluenesulfonamide (11.93 g, 69.681 mmol, 1.20 equiv), TEBAC (1.33 g, 5.833 mmol, 0.10 equiv), $K_2CO_3$ (0.80 g, 5.788 mmol, 0.10 equiv). The resulting solution was stirred for 3 days at 90 degrees C. in an oil bath. The reaction mixture was cooled to room temperature. The solids were filtered out. The resulting mixture was concentrated under vacuum. The residue was applied onto a silica gel column with ethyl acetate/petroleum ether (2:1). This resulted in 10.69 g (25.75%) of N-[(trans)-4-hydroxyoxolan-3-yl]-4-methylbenzenesulfonamide as a white solid. LC-MS: (ES, m/z): M+1=258.

Synthesis of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide: Into a 250-mL round-bottom flask purged and maintained with an inert atmosphere of nitrogen, was placed N-[(trans)-4-hydroxyoxolan-3-yl]-4-methylbenzenesulfonamide (10.50 g, 14.691 mmol, 1.30 equiv, 36%), THF (100 mL). This was followed by the addition of NaH (2.71 g, 67.756 mmol, 6.01 equiv, 60%), in portions at 0 degrees C. The resulting solution was stirred for 30 min at 0 degrees C. To this was added 5-bromo-6-fluoro-1-[[2-(trimethylsilyl)ethoxy]methyl]pyrrolo[2,3-b]pyridine (3.89 g, 11.266 mmol, 1.00 equiv) at 0 degrees C. The resulting solution was stirred for 4 hr at 70 degrees C. in an oil bath. The reaction mixture was cooled to room temperature. The reaction was then quenched by the addition of 500 mL of aqueous $NH_4Cl$. The resulting solution was extracted with 3×300 mL of ethyl acetate and the organic layers combined. The resulting mixture was washed with 1×1500 mL of brine. The mixture was dried over anhydrous sodium sulfate and concentrated under vacuum. The residue was applied onto a silica gel column with ethyl acetate/petroleum ether (1:2). This resulted in 3 g (45.71%) of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide as light yellow oil. $^1H$ NMR (300 MHz, Chloroform-d, ppm) δ 8.04 (s, 1H), 7.78-7.61 (m, 2H), 7.25-7.10 (m, 3H), 6.43 (d, J=3.6 Hz, 1H), 5.67 (d, J=10.8 Hz, 1H), 5.60 (d, J=5.7 Hz, 1H), 5.49 (d, J=10.8 Hz, 1H), 5.40 (dt, J=6.1, 3.1 Hz, 1H), 4.27 (dd, J=10.5, 5.9 Hz, 1H), 4.21-4.03 (m, 1H), 4.03-3.86 (m, 2H), 3.70-3.52 (m, 3H), 2.32 (s, 3H), 0.93 (ddt, J=10.6, 5.5, 2.6 Hz, 2H), −0.02 (s, 9H).

Synthesis of (trans)-10-(4-methylbenzenesulfonyl)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene: Into a 250-mL round-bottom flask purged and maintained with an inert atmosphere of nitrogen, was placed N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide (3.00 g, 5.149 mmol, 1.00 equiv), DMF (50.00 mL), phen (743.00 mg, 4.123 mmol, 0.80 equiv), CuI (785.00 mg, 4.122 mmol, 0.80 equiv), $K_2CO_3$ (2.14 g, 15.484 mmol, 3.01 equiv). The resulting solution was stirred for 2 days at 120 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 mL of brine. The mixture was dried over anhydrous sodium sulfate and concentrated under vacuum. The residue was applied onto a silica gel column with ethyl acetate/petroleum ether (1:2). This resulted in 2.5 g (82.26%) of (trans)-10-(4-methylbenzenesulfonyl)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene as yellow oil. LC-MS: (ES, m/z) M+1=502.

Synthesis of (11S,15R)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) and (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed): Into a 100-mL round-bottom flask, was placed Mg (2.04 g, 83.933 mmol, 19.81 equiv), MeOH (30.00 mL), (trans)-10-(4-methylbenzenesulfonyl)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraene (2.50 g, 4.236 mmol, 1.00 equiv, 85%). The resulting solution was stirred for 2 hr at 60 degrees C. in an oil bath. The reaction mixture was cooled to room temperature. The resulting solution was diluted with 300/300 mL of $NaHCO_3$ and $CH_2Cl_2$. The solids were filtered out and the organic was separated. The mixture was dried over anhydrous sodium sulfate and concentrated under vacuum. The residue was applied onto a silica gel column with ethyl acetate/petroleum ether (1:3). The crude product was purified by Chiral-Prep-HPLC with the following conditions: Mobile phase: A:n-Hexane (0.1% DEA) B:ETOH; Flow rate: 20 mL/min; Column: DAICEL CHIRALPAK IA, 250*20 mm, Sum; Gradient:12% B in 20 min; 220 nm. This resulted in 350 mg (23.78%) of (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) as yellow oil. and 400 mg (27.18%) of (11S,15R)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraene (assumed) as yellow oil. Peak 1: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H). Peak 2: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H).

Synthesis of (S)—N-[(2-bromophenyl)methylidene]-2-methylpropane-2-sulfinamide: Into a 3000-mL round-bottom flask, was placed 2-bromo-benzaldehyde (120.00 g, 648.579 mmol, 1.00 equiv), THF (2000.00 mL), (S)-2-methylpropane-2-sulfinamide (79.00 g, 651.815 mmol, 1.00 equiv), $Ti(OEt)_4$ (297.00 g, 1302.009 mmol, 2.01 equiv). The resulting solution was stirred overnight at 55 degrees C. in an oil bath. The reaction mixture was cooled to room temperature. The resulting mixture was concentrated under vacuum. The resulting solution was diluted with 2000/2000 mL of $H_2O$ and EtOAc. The solids were filtered out. The organic layer was separated from the filtration. The mixture was dried over anhydrous sodium sulfate and concentrated under vacuum. This resulted in 181 g (96.83%) of (S)—N-[(2-bromophenyl)methylidene]-2-methylpropane-2-sulfinamide as yellow oil. LC-MS: (ES, m/z): M+1: 288; H-NMR (300 MHz, DMSO-$d_6$, ppm) δ 8.81 (d, J=1.7 Hz, 1H), 8.03 (dt, J=6.6, 1.7 Hz, 1H), 7.84-7.74 (m, 1H), 7.54 (dp, J=5.6, 3.7, 2.4 Hz, 2H), 1.19 (d, J=1.7 Hz, 9H).

Synthesis of (S)—N-[(1S)-1-(2-bromophenyl)-3-(1,3-dioxan-2-yl)propyl]-2-methylpropane-2-sulfinamide: Into a 1000-mL 3-necked round-bottom flask purged and maintained with an inert atmosphere of nitrogen, was placed Mg (37.13 g, 1527.669 mmol, 3.97 equiv), $I_2$ (9.82 g, 38.691 mmol, 0.10 equiv), THF (300.00 mL), the resulting solution was warmed to 65 degrees C., followed by the addition of 2-(2-bromoethyl)-1,3-dioxane (30.00 g, 153.8020 mmol, 0.4 equiv) in THF (50 mL) at 65 degrees C. After addition completed, the mixture was cooled to room temperature, another 2-(2-bromoethyl)-1,3-dioxane (270.00 g, 1384.615 mmol, 3.6 equiv) in THF (150 mL) was added. Another 3000-mL 3-necked round-bottom flask purged and maintained with an inert atmosphere of nitrogen, was placed a solution of (S)—N-[(2-bromophenyl)methylidene]-2-methylpropane-2-sulfinamide (111.00 g, 385.149 mmol, 1.00 equiv) in DCM (800 mL). The above solution was added dropwise at −40 degrees C. The resulting solution was stirred for 1 hr at −40 degrees C. in a liquid nitrogen bath. The reaction was then quenched by the addition of 2000 mL of aqueous $NH_4Cl$. The resulting solution was extracted with 3×1000 mL of dichloromethane and the organic layers combined. The resulting mixture was washed with 1×3000 ml of brine. The mixture was dried over anhydrous sodium sulfate and concentrated under vacuum. This resulted in 150 g (96.32%) of (S)—N-[(1S)-1-(2-bromophenyl)-3-(1,3-dioxan-2-yl)propyl]-2-methylpropane-2-sulfinamide as yellow oil. LC-MS: (ES, m/z): M+1: 404

Synthesis of (2S)-2-(2-bromophenyl)pyrrolidine: Into a 2000-mL round-bottom flask, was placed (S)—N-[(1S)-1-(2-bromophenyl)-3-(1,3-dioxan-2-yl)propyl]-2-methylpropane-2-sulfinamide (150.00 g, 370.957 mmol, 1.00 equiv), TFA (360.00 mL), $H_2O$ (90 mL), the resulting solution was stirred for 1 h at room temperature. TFA (1350.00 mL), triethylsilane (129.40 g, 1112.841 mmol, 3.00 equiv) was added. The resulting solution was stirred overnight at room temperature. The resulting mixture was concentrated. The resulting solution was diluted with 2000 mL of $H_2O$. The resulting solution was extracted with 2×500 mL of MTBE and the organic layers combined. The resulting mixture was washed with 1×1000 ml of HCl (2 mol/L). The pH value of the aqueous was adjusted to 13 with NaOH (4 mol/L). The resulting solution was extracted with 3×500 mL of dichloromethane and the organic layers combined and dried over anhydrous sodium sulfate and concentrated. This resulted in 40 g (47.69%) of (2S)-2-(2-bromophenyl)pyrrolidine as yellow oil. Its optically pure enantiomer was recrystallized from dibenzoyl-L-taratric acid salt in EA. LC-MS: (ES, m/z): M+1:226; H-NMR (300 MHz, DMSO-$d_6$, ppm) δ 7.67 (dd, J=7.8, 1.8 Hz, 1H), 7.53 (dd, J=7.9, 1.3 Hz, 1H), 7.34 (td, J=7.5, 1.3 Hz, 1H), 7.13 (td, J=7.6, 1.8 Hz, 1H), 4.33 (t, J=7.4 Hz, 1H), 3.10-2.87 (m, 2H), 2.35-2.18 (m, 1H), 1.80-1.64 (m, 2H), 1.40-1.20 (m, 1H).

Synthesis of tert-butyl 2-[(2S)-2-(2-bromophenyl)pyrrolidin-1-yl]-7-azaspiro[3.5]nonane-7-carboxylate: Into a 250-mL round-bottom flask, was placed (2S)-2-(2-bromophenyl)pyrrolidine (6.18 g, 27.331 mmol, 1.00 equiv), DCM (100.00 mL), tert-butyl 2-oxo-7-azaspiro[3.5]nonane-7-carboxylate (6.56 g, 27.412 mmol, 1.00 equiv), NaBH$(OAc)_3$ (11.65 g, 54.968 mmol, 2.01 equiv). The resulting solution was stirred for 2 hr at room temperature. The resulting mixture was concentrated under vacuum. The residue was applied onto a silica gel column with ethyl acetate/petroleum ether (1:1). This resulted in 7.9 g (64.31%) of tert-butyl 2-[(2S)-2-(2-bromophenyl)pyrrolidin-1-yl]-7-azaspiro[3.5]nonane-7-carboxylate as yellow oil. LC-MS: (ES, m/z): M+1:449

Synthesis of tert-butyl 2-[(2S)-2-[2-(prop-1-en-2-yl)phenyl]pyrrolidin-1-yl]-7-azaspiro[3.5]nonane-7-carboxylate: Into a 250-mL round-bottom flask purged and maintained with an inert atmosphere of nitrogen, was placed tert-butyl 2-[(2S)-2-(2-bromophenyl)pyrrolidin-1-yl]-7-azaspiro[3.5]nonane-7-carboxylate (7.15 g, 15.909 mmol, 1.00 equiv), dioxane (72.00 mL), $H_2O$ (8.00 mL), 4,4,5,5-tetramethyl-2-(prop-1-en-2-yl)-1,3,2-dioxaborolane (6.39 g, 38.027 mmol, 2.39 equiv), $K_2CO_3$ (6.61 g, 47.827 mmol, 3.01 equiv), $Pd(dppf)Cl_2 \cdot CH_2Cl_2$ (1.30 g, 1.596 mmol, 0.10 equiv). The resulting solution was stirred overnight at 80 degrees C. in an oil bath. The reaction mixture was cooled to room temperature. The resulting mixture was concentrated under vacuum. The residue was applied onto a silica gel column with ethyl acetate/petroleum ether (1:2). This resulted in 4.34 g (66.44%) of tert-butyl 2-[(2S)-2-[2-(prop-1-en-2-yl)phenyl]pyrrolidin-1-yl]-7-azaspiro[3.5]nonane-7-carboxylate as yellow oil. LC-MS: (ES, m/z): M+1:411

Synthesis of tert-butyl 2-[(2S)-2-(2-isopropylphenyl)pyrrolidin-1-yl]-7-azaspiro[3.5]nonane-7-carboxylate: Into a 100-mL pressure tank reactor (10 atm), was placed tert-butyl 2-[(2S)-2-[2-(prop-1-en-2-yl)phenyl]pyrrolidin-1-yl]-7-azaspiro[3.5]nonane-7-carboxylate (3.58 g, 8.719 mmol, 1.00 equiv), EtOH (50.00 mL), 10% Pd/C (500.00 mg, 4.698 mmol, 0.54 equiv), to the above $H_2$ was introduced in. The resulting solution was stirred overnight at 50 degrees C. in an oil bath. The solids were filtered out. The resulting mixture was concentrated under vacuum. The residue was applied onto a silica gel column with ethyl acetate/petroleum ether (1:2). This resulted in 2.6 g (72.27%) of tert-butyl 2-[(2S)-2-(2-isopropylphenyl)pyrrolidin-1-yl]-7-azaspiro[3.5]nonane-7-carboxylate as yellow oil. LC-MS: (ES, m/z): M+1:413

Synthesis of 2-[(2S)-2-(2-isopropylphenyl)pyrrolidin-1-yl]-7-azaspiro[3.5]nonane hydrochloride: Into a 100-mL round-bottom flask, was placed tert-butyl 2-[(2S)-2-(2-isopropylphenyl)pyrrolidin-1-yl]-7-azaspiro[3.5]nonane-7-carboxylate (2.60 g, 6.301 mmol, 1.00 equiv), HCl(gas) in 1,4-dioxane (20.00 mL). The resulting solution was stirred for 1 hr at room temperature. The resulting mixture was concentrated under vacuum. This resulted in 2.1 g (95.50%) of 2-[(2S)-2-(2-isopropylphenyl)pyrrolidin-1-yl]-7-azaspiro[3.5]nonane hydrochloride as a red solid. LC-MS: (ES, m/z): M+1:313

Synthesis of methyl 2-bromo-4-[2-[(2S)-2-(2-isopropylphenyl)pyrrolidin-1-yl]-7-azaspiro[3.5]nonan-7-yl]benzoate: Into a 100-mL round-bottom flask, was placed 2-[(2S)-2-(2-isopropylphenyl)pyrrolidin-1-yl]-7-azaspiro[3.5]nonane hydrochloride (1.32 g, 3.783 mmol, 1.00 equiv), DMSO (20.00 mL), methyl 2-bromo-4-fluorobenzoate (1.76 g, 7.552 mmol, 2.00 equiv), $Na_2CO_3$ (1.61 g, 15.190 mmol, 4.02 equiv). The resulting solution was stirred for 7 hr at 110 degrees C. in an oil bath. The reaction mixture was cooled to room temperature. The resulting solution was diluted with 200 mL of water. The resulting solution was extracted with 3×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with ethyl acetate/petroleum ether (1:2). This resulted in 1.05 g (52.82%) of methyl 2-bromo-4-[2-[(2S)-2-(2-isopropylphenyl)pyrrolidin-1-yl]-7-azaspiro[3.5]nonan-7-yl]benzoate as yellow oil. LC-MS: (ES, m/z): M+1: 579; H-NMR (300 MHz, Chloroform-d, ppm) δ 7.80 (d, J=8.9 Hz, 1H), 7.64 (d, J=7.4 Hz, 1H), 7.27-7.14 (m, 3H), 7.06 (d, J=2.6 Hz, 1H), 6.73 (dd, J=9.0, 2.4 Hz, 1H), 3.87 (s, 3H), 3.68 (t, J=8.0 Hz, 1H), 3.34 (dq, J=13.7, 6.8, 6.1 Hz, 1H), 3.28-3.04 (m, 6H), 2.39 (q, J=8.8 Hz, 1H), 2.22 (dt, J=19.5, 8.2 Hz, 1H), 1.88 (dq, J=31.2, 10.5, 10.1 Hz, 4H), 1.75-1.42 (m, 6H), 1.26 (t, J=7.0 Hz, 6H).

Synthesis of methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraen-10-yl]benzoate (assumed): Into a 40-mL vial purged and maintained with an inert atmosphere of nitrogen, was placed methyl 2-bromo-4-[2-[(2S)-2-(2-isopropylphenyl)pyrrolidin-1-yl]-7-azaspiro[3.5]nonan-7-yl]benzoate (770.00 mg, 1.465 mmol, 1.70 equiv), toluene (10.00 mL), (11R,15S)-4-[[2-(trimethylsilyl)ethoxy]methyl]-13,16-dioxa-2,4,10-triazatetracyclo[7.7.0.0^[3,7].0^[11,15]]hexadeca-1(9),2,5,7-tetraene (assumed) (300.00 mg, 0.863 mmol, 1.00 equiv), $Cs_2CO_3$ (843.00 mg, 2.587 mmol, 3.00 equiv), Xantphos (100.00 mg, 0.173 mmol, 0.20 equiv), $Pd_2(dba)_3 \cdot CHCl_3$ (89.00 mg, 0.086 mmol, 0.10 equiv). The resulting solution was stirred for 5 hr at 100 degrees C. in an oil bath. The reaction mixture was cooled to room temperature. The resulting mixture was concentrated under vacuum. The residue was applied onto a silica gel column with ethyl acetate/petroleum ether (1:1). This resulted in 600 mg (87.74%) of methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0^[3,7]0.0^[11,15]]hexadeca-1(9),2,5,7-tetraen-10-yl]benzoate (assumed) as a yellow solid. LC-MS: (ES, m/z): M+1:792

Synthesis of methyl 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed): Into a 40-mL vial, was placed methyl 4-[2-[(2S)-2-(2-isopropylphenyl)pyrrolidin-1-yl]-7-azaspiro[3.5]nonan-7-yl]-2-[(11R,15S)-4-[[2-(trimethylsilyl)ethoxy]methyl]-13,16-dioxa-2,4,10-triazatetracyclo[7.7.0.0 [3,7]0.0^[11,15]]hexadeca-1(9),2,5,7-tetraen-10-yl]benzoate (assumed) (600.00 mg, 0.757 mmol, 1.00 equiv), TBAF in THF (10.00 mL), ethylenediamine (910.00 mg, 15.141 mmol, 19.99 equiv). The resulting solution was stirred for 8 hr at 70 degrees C. in an oil bath. The reaction mixture was cooled to room temperature. The resulting solution was diluted with 200 mL of water. The resulting solution was extracted with 2×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with ethyl acetate/petroleum ether (2:1). This resulted in 300 mg (59.84%) of methyl 2-[(11R,15S)-13,16-dioxa-2,4,10-triazatetracyclo[7.7.0.0^[3,7]0.0^[11, 15]]hexadeca-1(9),2,5,7-tetraen-10-yl]-4-[2-[(2S)-2-(2-isopropylphenyl)pyrrolidin-1-yl]-7-azaspiro[3.5]nonan-7-yl] benzoate (assumed) as a yellow solid. LC-MS: (ES, m/z): M+1:662

Synthesis of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed): Into a 100-mL round-bottom flask, was placed methyl 2-[(11R, 15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoate (assumed) (300.00 mg, 0.453 mmol, 1.00 equiv), MeOH (5.00 mL), dioxane (5.00 mL), NaOH (2.00 mL). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 2×50 mL of ethyl acetate and the organic layers combined. The resulting mixture was washed with 1×200 ml of brine. The mixture was dried over anhydrous sodium sulfate and concentrated under vacuum. The residue was applied onto a silica gel column with dichloromethane/methanol (10:1). This resulted in 240 mg (81.73%) of 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) as a yellow solid. LC-MS: (ES, m/z): M+1:648

Synthesis of 8-methyl-1,4-dioxaspiro[4.5]decan-8-ol Into a 1-L 3-necked round-bottom flask purged and maintained with an inert atmosphere of nitrogen, was placed 1,4-dioxaspiro[4.5]decan-8-one (100.00 g, 640.283 mmol), THF (500.00 mL). This was followed by the addition of $CH_3MgBr$ (256 ml, 3M), in portions at 0 degrees C. The resulting solution was stirred for 4 h at 0 degrees C. The reaction was then quenched by the addition of $NH_4Cl$(aq). The resulting mixture was concentrated. The residue was dissolved in 500 mL of DCM. The resulting mixture was washed with 3×50 ml of $H_2O$. The mixture was dried over anhydrous sodium sulfate and concentrated. This resulted in 110 g (99.75%) of 8-methyl-1,4-dioxaspiro[4.5]decan-8-ol as white oil. H-NMR: (300 MHz, Chloroform-d) δ: 3.98-3.93 (m, 4H), 2.07-1.52 (m, 8H), 1.27 (s, 3H).

Synthesis of 4-hydroxy-4-methylcyclohexan-1-one: Into a 1-L round-bottom flask, was placed 8-methyl-1,4-dioxaspiro[4.5]decan-8-ol (110.00 g), 0.05N HCl (500.00 mL). The resulting solution was stirred for 4 hr at 70 degrees C. in an oil bath. The resulting solution was extracted with 3×300 mL of ethyl acetate. The resulting mixture was washed with 1×300 ml of $NaHCO_3$ and 1×200 mL of NaCl. The mixture was dried over anhydrous sodium sulfate. The residue was applied onto a silica gel column and purified with ethyl acetate/petroleum ether (1:2). This resulted in 40 g of 4-hydroxy-4-methylcyclohexan-1-one as yellow oil. H-NMR: (300 MHz, Chloroform-d) δ 2.73 (ddd, J=15.3, 12.9, 6.3 Hz, 2H), 2.33-2.18 (m, 2H), 2.06-1.93 (m, 2H), 1.93-1.78 (m, 2H), 1.38 (s, 3H).

Synthesis of 1-methyl-4-(nitromethyl)cyclohex-3-en-1-ol Into a 500-mL round-bottom flask, was placed 4-hydroxy-4-methylcyclohexan-1-one (20.00 g, 156.042 mmol), $CH_3NO_2$ (100.00 mL), methyl[2-(methylamino)ethyl]amine (1.38 g, 15.654 mmol). The resulting solution was stirred for 6 hr at 100 degrees C. in an oil bath. The resulting mixture was concentrated. The residue was applied onto a silica gel column and purified with ethyl acetate/petroleum ether (1:3). This resulted in 21 g (78.61%) of 1-methyl-4-(nitromethyl)cyclohex-3-en-1-ol as brown oil. H-NMR: (300 MHz, Chloroform-d) δ 5.87 (t, J=2.7 Hz, 1H), 4.87 (s, 2H), 2.41-2.11 (m, 4H), 1.85-1.62 (m, 2H), 1.54 (d, J=16.0 Hz, 1H), 1.31 (s, 3H).

Synthesis of 4-(aminomethyl)-1-methylcyclohexan-1-ol Into a 100-mL pressure tank reactor, was placed 1-methyl-4-(nitromethyl)cyclohex-3-en-1-ol (5.00 g, 29.206 mmol), i-PrOH (50 mL), Pt/C (1.14 g, 5.841 mmol). To the above, $H_2$ (g, 20 atm) was introduced in. The resulting solution was stirred for 20 hr at 30 degrees C. in an oil bath. The solids were filtered out. The resulting mixture was concentrated. This resulted in 2.5 g (crude) of 4-(aminomethyl)-1-methylcyclohexan-1-ol as black oil.

Synthesis of 3-nitro-4-([[(1r,4r)-4-hydroxy-4-methylcyclohexyl]methyl]amino)benzenesulfonamide and 3-nitro-4-([[(1s,4s)-4-hydroxy-4-methylcyclohexyl]methyl]amino) benzenesulfonamide Into a 100-mL round-bottom flask, was placed 4-(aminomethyl)-1-methylcyclohexan-1-ol (2.50 g, crude), 4-fluoro-3-nitrobenzenesulfonamide (3.84 g, 17.441 mmol), THF (30 mL), TEA (5.29 g, 52.376 mmol). The resulting solution was stirred for 14 hr at room temperature. The resulting mixture was concentrated. The residue was applied onto a C18 gel column with ($H_2O$:ACN=100:0 to 100:30). This resulted in 1 g of 3-nitro-4-([[(1r,4r)-4-hydroxy-4-methylcyclohexyl]methyl]amino)benzene sulfonamide (assumed) as a yellow solid. H-NMR (400 MHz, DMSO-$d_6$) δ 8.51 (d, J=6.4 Hz, 1H), 8.47 (s, 1H), 7.85 (d, J=9.2 Hz, 1H), 7.36 (s, 2H), 7.27 (dd, J=9.2, 2.5 Hz, 1H), 4.26 (d, J=2.8 Hz, 1H), 3.34 (s, 1H), 2.11 (d, J=17.6 Hz, 0H), 1.69 (d, J=13.6 Hz, 3H), 1.55 (d, J=12.8 Hz, 2H), 1.34 (t, J=12.8 Hz, 2H), 1.16 (d, J=12.8 Hz, 1H), 1.10-1.06 (m, 4H). This resulted in 500 mg of 3-nitro-4-([[(1s,4s)-4-hydroxy-4-methylcyclohexyl]methyl]amino)benzene sulfonamide (assumed) as a yellow solid. H-NMR (400 MHz, DMSO-$d_6$) δ 8.54 (d, J=6.4 Hz, 1H), 8.47 (s, 1H), 7.84 (d, J=9.2 Hz, 1H), 7.34 (s, 2H), 7.26 (d, J=9.2 Hz, 1H), 4.24-4.08 (m, 1H), 3.96 (s, 1H), 3.32 (d, J=6.4 Hz, 2H), 3.20-3.11 (m, 1H), 1.57 (s, 2H), 1.48 (d, J=12.4 Hz, 3H), 1.40 (d, J=12.4 Hz, 2H), 1.23 (td, J=13.2, 3.6 Hz, 3H), 1.08 (s, 3H).

Synthesis of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1r,4r)-4-hydroxy-4-methylcyclohexyl]methyl]amino)benzenesulfonyl] benzamide (assumed) Into a 40-mL vial, was placed 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) (80.00 mg, 0.123 mmol, 1.00 equiv), DCM (5.00 mL), 3-nitro-4-([[(1r,4r)-4-hydroxy-4-methylcyclohexyl]methyl]amino)benzenesulfonamide (42.00 mg, 0.122 mmol, 0.99 equiv), EDCI (47.00 mg, 0.245 mmol, 1.99 equiv), DMAP (60.00 mg, 0.491 mmol, 3.98 equiv). The resulting solution was stirred overnight at 30 degrees C. The resulting mixture was concentrated under vacuum. The residue was applied onto a silica gel column with dichloromethane/methanol (10:1). The crude product was purified by Prep-HPLC with the following conditions (2 #SHIMADZU (HPLC-01)): Column, XBridge Shield RP18 OBD Column, 19*150 mm, Sum; mobile phase, Water (0.05% $NH_3 \cdot H_2O$) and ACN (44% Phase B up to 54% in 7 min); Detector, UV. This resulted in 28 mg (23.30%) of 2-[(11R,15S)-13,16-dioxa-2,4,10-triazatetracyclo[7.7.0.0○

[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1r,4r)-4-hydroxy-4-methylcyclohexyl]methyl]amino)benzenesulfonyl]benzamide (assumed) as a yellow solid. LC-MS: (ES, m/z): M+1:973; H-NMR (300 MHz, DMSO-$d_6$, ppm) δ 8.61-8.21 (m, 2H), 7.55 (s, 2H), 7.41-6.96 (m, 5H), 6.71 (dd, J=62.8, 25.1 Hz, 4H), 6.01 (ddd, J=13.5, 3.4, 1.9 Hz, 1H), 4.65 (s, 1H), 4.54-4.39 (m, 1H), 4.24 (s, 2H), 4.08 (d, J=7.0 Hz, 1H), 3.83 (dd, J=18.7, 9.5 Hz, 1H), 3.50 (dt, J=35.3, 8.8 Hz, 5H), 3.31-2.88 (m, 9H), 2.44-2.02 (m, 2H), 2.04-1.29 (m, 19H), 1.27-1.02 (m, 11H).

Synthesis of 2-[(11R,15S)-13,16-dioxa-2,4,10-triazatetracyclo[7.7.0.0^[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1s,4s)-4-hydroxy-4-methylcyclohexyl]methyl]amino)benzenesulfonyl]benzamide (assumed): Into a 40-mL vial, was placed 2-[(11R,15S)-13,16-dioxa-2,4,10-triazatetracyclo[7.7.0.0^[3,7]0.0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]benzoic acid (assumed) (80.00 mg, 0.123 mmol, 1.00 equiv), DCM (5.00 mL), 3-nitro-4-([[(1s,4s)-4-hydroxy-4-methylcyclohexyl]methyl]amino)benzenesulfonamide (42.00 mg, 0.122 mmol, 0.99 equiv), EDCI (47.00 mg, 0.245 mmol, 1.99 equiv), DMAP (60.00 mg, 0.491 mmol, 3.98 equiv). The resulting solution was stirred overnight at 30 degrees C. The resulting mixture was concentrated under vacuum. The residue was applied onto a silica gel column with dichloromethane/methanol (10:1). The crude product was purified by Prep-HPLC with the following conditions (2 #SHIMADZU (HPLC-01)): Column, XBridge Shield RP18 OBD Column, 19*150 mm, 5um; mobile phase, Water (0.05% $NH_3 \cdot H_2O$) and ACN (44% Phase B up to 54% in 7 min); Detector, UV. This resulted in 15 mg (12.48%) of 2-[(11R,15S)-13,16-dioxa-2,4,10-triazatetracyclo[7.7.0.0◯[3,7].0^[11,15]]hexadeca-1(9),2,5,7-tetraen-10-yl]-4-[2-[(2S)-2-(2-isopropylphenyl)pyrrolidin-1-yl]-7-azaspiro[3.5]nonan-7-yl]-N-[3-nitro-4-([[(1s,4s)-4-hydroxy-4-methylcyclohexyl]methyl]amino)benzenesulfonyl]benzamide (assumed) as a yellow solid. LC-MS: (ES, m/z): M+1:973; H-NMR (300 MHz, DMSO-$d_6$, ppm) δ 8.61-8.21 (m, 2H), 7.55 (s, 2H), 7.41-6.96 (m, 5H), 6.71 (dd, J=62.8, 25.1 Hz, 4H), 6.01 (ddd, J=13.5, 3.4, 1.9 Hz, 1H), 4.65 (s, 1H), 4.54-4.39 (m, 1H), 4.24 (s, 2H), 4.08 (d, J=7.0 Hz, 1H), 3.83 (dd, J=18.7, 9.5 Hz, 1H), 3.50 (dt, J=35.3, 8.8 Hz, 5H), 3.31-2.88 (m, 9H), 2.44-2.02 (m, 2H), 2.04-1.29 (m, 19H), 1.27-1.02 (m, 11H).

Example 8: Preparation of 4-[2-[(2S)-2-(2-isopropylphenyl)pyrrolidin-1-yl]-7-azaspiro[3.5]nonan-7-yl]-N-[(3S)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed) and 4-[2-[(2S)-2-(2-isopropylphenyl)pyrrolidin-1-yl]-7-azaspiro[3.5]nonan-7-yl]-N-[(3R)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed)

Synthesis of (S)—N-[(2-bromophenyl)methylidene]-2-methylpropane-2-sulfinamide: Into a 3000-mL round-bottom flask, was placed 2-bromo-benzaldehyde (120.00 g, 648.579 mmol, 1.00 equiv), THF (2000.00 mL), (S)-2-methylpropane-2-sulfinamide (79.00 g, 651.815 mmol, 1.00 equiv), $Ti(OEt)_4$ (297.00 g, 1302.009 mmol, 2.01 equiv). The resulting solution was stirred overnight at 55 degrees C. in an oil bath. The reaction mixture was cooled to room temperature. The resulting mixture was concentrated under vacuum. The resulting solution was diluted with 2000/2000 mL of $H_2O$ and EtOAc. The solids were filtered out. The organic layer was separated from the filtration. The mixture was dried over anhydrous sodium sulfate and concentrated under vacuum. This resulted in 181 g (96.83%) of (S)—N-[(2-bromophenyl)methylidene]-2-methylpropane-2-sulfinamide as yellow oil. LC-MS: (ES, m/z): M+1: 288; H-NMR (300 MHz, DMSO-$d_6$, ppm) δ 8.81 (d, J=1.7 Hz, 1H), 8.03 (dt, J=6.6, 1.7 Hz, 1H), 7.84-7.74 (m, 1H), 7.54 (dp, J=5.6, 3.7, 2.4 Hz, 2H), 1.19 (d, J=1.7 Hz, 9H).

Synthesis of (S)—N-[(1S)-1-(2-bromophenyl)-3-(1,3-dioxan-2-yl)propyl]-2-methylpropane-2-sulfinamide: Into a 1000-mL 3-necked round-bottom flask purged and maintained with an inert atmosphere of nitrogen, was placed Mg (37.13 g, 1527.669 mmol, 3.97 equiv), $I_2$ (9.82 g, 38.691 mmol, 0.10 equiv), THF (300.00 mL), the resulting solution was warmed to 65 degrees C., followed by the addition of 2-(2-bromoethyl)-1,3-dioxane (30.00 g, 153.8020 mmol, 0.4 equiv) in THF (50 mL) at 65 degrees C. After addition completed, the mixture was cooled to room temperature, another 2-(2-bromoethyl)-1,3-dioxane (270.00 g, 1384.615 mmol, 3.6 equiv) in THF (150 mL) was added. Another 3000-mL 3-necked round-bottom flask purged and maintained with an inert atmosphere of nitrogen, was placed a solution of (S)—N-[(2-bromophenyl)methylidene]-2-methylpropane-2-sulfinamide (111.00 g, 385.149 mmol, 1.00 equiv) in DCM (800 mL). The above solution was added dropwise at −40 degrees C. The resulting solution was stirred for 1 hr at −40 degrees C. in a liquid nitrogen bath. The reaction was then quenched by the addition of 2000 mL of aqueous NH4Cl. The resulting solution was extracted with 3×1000 mL of dichloromethane and the organic layers combined. The resulting mixture was washed with 1×3000 ml of brine. The mixture was dried over anhydrous sodium sulfate and concentrated under vacuum. This resulted in 150 g (96.32%) of (S)—N-[(1S)-1-(2-bromophenyl)-3-(1,3-dioxan-2-yl)propyl]-2-methylpropane-2-sulfinamide as yellow oil. LC-MS: (ES, m/z): M+1:

Synthesis of (2S)-2-(2-bromophenyl)pyrrolidine: Into a 2000-mL round-bottom flask, was placed (S)—N-[(1S)-1-(2-bromophenyl)-3-(1,3-dioxan-2-yl)propyl]-2-methylpropane-2-sulfinamide (150.00 g, 370.957 mmol, 1.00 equiv), TFA (360.00 mL), $H_2O$ (90 mL), the resulting solution was stirred for 1 h at room temperature. TFA (1350.00 mL), triethylsilane (129.40 g, 1112.841 mmol, 3.00 equiv) was added. The resulting solution was stirred overnight at room temperature. The resulting mixture was concentrated. The resulting solution was diluted with 2000 mL of $H_2O$. The resulting solution was extracted with 2×500 mL of MTBE and the organic layers combined. The resulting mixture was washed with 1×1000 ml of HCl (2 mol/L). The pH value of the aqueous was adjusted to 13 with NaOH (4 mol/L). The resulting solution was extracted with 3×500 mL of dichloromethane and the organic layers combined and dried over anhydrous sodium sulfate and concentrated. This resulted in 40 g (47.69%) of (2S)-2-(2-bromophenyl)pyrrolidine as yellow oil. Its optically pure enantiomer was recrystallized from dibenzoyl-L-taratric acid salt in EA. LC-MS: (ES, m/z): M+1:226; H-NMR (300 MHz, DMSO-$d_6$, ppm) δ 7.67 (dd, J=7.8, 1.8 Hz, 1H), 7.53 (dd, J=7.9, 1.3 Hz, 1H), 7.34 (td, J=7.5, 1.3 Hz, 1H), 7.13 (td, J=7.6, 1.8 Hz, 1H), 4.33 (t, J=7.4 Hz, 1H), 3.10-2.87 (m, 2H), 2.35-2.18 (m, 1H), 1.80-1.64 (m, 2H), 1.40-1.20 (m, 1H).

Synthesis of tert-butyl 2-[(2S)-2-(2-bromophenyl)pyrrolidin-1-yl]-7-azaspiro[3.5]nonane-7-carboxylate: Into a 250-mL round-bottom flask, was placed (2S)-2-(2-bromophenyl)pyrrolidine (6.18 g, 27.331 mmol, 1.00 equiv), DCM (100.00 mL), tert-butyl 2-oxo-7-azaspiro[3.5]nonane-7-carboxylate (6.56 g, 27.412 mmol, 1.00 equiv), NaBH$(OAc)_3$ (11.65 g, 54.968 mmol, 2.01 equiv). The resulting solution was stirred for 2 hr at room temperature. The resulting mixture was concentrated under vacuum. The residue was applied onto a silica gel column with ethyl acetate/petroleum ether (1:1). This resulted in 7.9 g (64.31%) of tert-butyl 2-[(2S)-2-(2-bromophenyl)pyrrolidin-1-yl]-7-azaspiro[3.5]nonane-7-carboxylate as yellow oil. LC-MS: (ES, m/z): M+1:449

Synthesis of tert-butyl 2-[(2S)-2-[2-(prop-1-en-2-yl)phenyl]pyrrolidin-1-yl]-7-azaspiro[3.5]nonane-7-carboxylate: Into a 250-mL round-bottom flask purged and maintained with an inert atmosphere of nitrogen, was placed tert-butyl 2-[(2S)-2-(2-bromophenyl)pyrrolidin-1-yl]-7-azaspiro[3.5]nonane-7-carboxylate (7.15 g, 15.909 mmol, 1.00 equiv), dioxane (72.00 mL), $H_2O$ (8.00 mL), 4,4,5,5-tetramethyl-2-(prop-1-en-2-yl)-1,3,2-dioxaborolane (6.39 g, 38.027 mmol, 2.39 equiv), $K_2CO_3$ (6.61 g, 47.827 mmol, 3.01 equiv), $Pd(dppf)Cl_2 \cdot CH_2Cl_2$ (1.30 g, 1.596 mmol, 0.10 equiv). The resulting solution was stirred overnight at 80 degrees C. in an oil bath. The reaction mixture was cooled to room temperature. The resulting mixture was concentrated under vacuum. The residue was applied onto a silica gel column with ethyl acetate/petroleum ether (1:2). This resulted in 4.34 g (66.44%) of tert-butyl 2-[(2S)-2-[2-(prop-1-en-2-yl)phenyl]pyrrolidin-1-yl]-7-azaspiro[3.5]nonane-7-carboxylate as yellow oil. LC-MS: (ES, m/z): M+1:411

Synthesis of tert-butyl 2-[(2S)-2-(2-isopropylphenyl)pyrrolidin-1-yl]-7-azaspiro[3.5]nonane-7-carboxylate: Into a 100-mL pressure tank reactor (10 atm), was placed tert-butyl 2-[(2S)-2-[2-(prop-1-en-2-yl)phenyl]pyrrolidin-1-yl]-7-azaspiro[3.5]nonane-7-carboxylate (3.58 g, 8.719 mmol, 1.00 equiv), EtOH (50.00 mL), 10% Pd/C (500.00 mg, 4.698 mmol, 0.54 equiv), to the above $H_2$ was introduced in. The resulting solution was stirred overnight at 50 degrees C. in an oil bath. The solids were filtered out. The resulting mixture was concentrated under vacuum. The residue was applied onto a silica gel column with ethyl acetate/petroleum ether (1:2). This resulted in 2.6 g (72.27%) of tert-butyl 2-[(2S)-2-(2-isopropylphenyl)pyrrolidin-1-yl]-7-azaspiro[3.5]nonane-7-carboxylate as yellow oil. LC-MS: (ES, m/z): M+1:413

Synthesis of 2-[(2S)-2-(2-isopropylphenyl)pyrrolidin-1-yl]-7-azaspiro[3.5]nonane hydrochloride: Into a 100-mL round-bottom flask, was placed tert-butyl 2-[(2S)-2-(2-isopropylphenyl)pyrrolidin-1-yl]-7-azaspiro[3.5]nonane-7-carboxylate (2.60 g, 6.301 mmol, 1.00 equiv), HCl(gas) in 1,4-dioxane (20.00 mL). The resulting solution was stirred for 1 hr at room temperature. The resulting mixture was concentrated under vacuum. This resulted in 2.1 g (95.50%) of 2-[(2S)-2-(2-isopropylphenyl)pyrrolidin-1-yl]-7-azaspiro[3.5]nonane hydrochloride as a red solid. LC-MS: (ES, m/z): M+1:313

Synthesis of methyl 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoate: Into a 40-mL vial, was placed 2-[(2S)-2-(2-isopropylphenyl)pyrrolidin-1-yl]-7-azaspiro[3.5]nonane hydrochloride (700 mg, 2.006 mmol, 1.00 equiv), DMSO (10.00 mL), methyl 4-fluoro-2-[1H-pyrrolo[2,3-b]pyridin-5-yloxy]benzoate (518 mg, 1.810 mmol, 0.90 equiv), $Na_2CO_3$ (533 mg, 5.029 mmol, 2.51 equiv). The resulting solution was stirred overnight at 130 degrees C. in an oil bath. The reaction mixture was cooled to room temperature. The resulting solution was diluted with 200 mL of $H_2O$. The resulting solution was extracted with 3×50 mL of ethyl acetate and the organic layer combined. The resulting mixture was washed with 1×200 ml of brine. The mixture was dried over anhydrous sodium sulfate and concentrated under vacuum. The residue was applied onto a silica gel column with ethyl acetate/petroleum ether (2:1). This resulted in 325 mg (27.99%) of methyl 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoate as yellow oil. LC-MS: (ES, m/z): M+1:579

Synthesis of 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoic acid: Into a 40-mL vial, was placed methyl 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoate (300.00 mg, 0.518 mmol, 1.00 equiv), MeOH (5.00 mL), dioxane (5.00 mL), NaOH (4N, 2.00 mL). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 3×30 mL of dichloromethane and the organic layers combined. The resulting mixture was washed with 1×100 ml of brine. The mixture was dried over anhydrous sodium sulfate and concentrated under vacuum. The residue was applied onto a silica gel column with dichloromethane/methanol (10:1). This resulted in 133 mg (45.43%) of 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoic acid as a light yellow solid. LC-MS: (ES, m/z): M+1: 565

Synthesis of (2R)-1,4-dioxane-2-carbaldehyde: Into a 100-mL round-bottom flask, was placed (2S)-1,4-dioxan-2-ylmethanol (2.36 g, 19.978 mmol, 1.00 equiv), $CH_3CN$ (50.00 mL, 1.218 mmol, 0.0 equiv), IBX (9.51 g, 33.962 mmol, 1.70 equiv). The resulting solution was stirred for 4 h at 70 degrees C. in an oil bath. The solids were filtered out. The resulting mixture was concentrated. This resulted in 2.0 g (86.22%) of (2R)-1,4-dioxane-2-carbaldehyde as colorless oil. $^1H$ NMR (300 MHz, $CDCl_3$, ppm) δ 9.66 (s, 1H), 4.12-3.77 (m, 7H).

Synthesis of 2-amino-2-[(2S)-1,4-dioxan-2-yl]acetonitrile: Into a 100-mL pressure tank reactor, was placed (2R)-1,4-dioxane-2-carbaldehyde (2.00 g, 17.224 mmol, 1.00 equiv). $NH_3$/MeOH (7M) (40.00 mL). This was followed by the addition of TMSCN (2.97 g, 29.970 mmol, 1.74 equiv). The resulting solution was stirred for overnight at 70 degrees C. in an oil bath. The resulting mixture was concentrated. The residue was applied onto a silica gel column and eluted with ethyl acetate/petroleum ether (3:1). The collected fractions were combined and concentrated. This resulted in 2.0 g (81.68%) of 2-amino-2-[(2S)-1,4-dioxan-2-yl]acetonitrile as brown oil. LCMS (ES, m/z): M+1: 143

Synthesis of amino((2S)-1,4-dioxan-2-yl)acetic acid: Into a 20-mL round-bottom flask, was placed 2-amino-2-[(2S)-1,4-dioxan-2-yl]acetonitrile (2.00 g, 14.069 mmol, 1.00 equiv), NaOH (4M) (5.00 mL). The resulting solution was stirred for overnight at 70 degrees C. in an oil bath. The pH value of the solution was adjusted to 6 with HOAc. The solids were collected by filtration. The solid was dried in an oven under reduced pressure. This resulted in 1.2 g (52.93%) of amino((2S)-1,4-dioxan-2-yl)acetic acid as a white solid. LCMS (ES, m/z): M+1: 162

Synthesis of 2-amino-2-[(2S)-1,4-dioxan-2-yl]ethanol: Into a 100-mL round-bottom flask, was placed amino((2S)-

1,4-dioxan-2-yl)acetic acid (1.20 g, 7.446 mmol, 1.00 equiv), THF (40.00 mL, 0.555 mmol, 0.07 equiv), $LiAlH_4$ (0.85 g, 22.396 mmol, 3.01 equiv). The resulting solution was stirred for 4 h at 60 degrees C. in an oil bath. The reaction was then quenched by the addition of 2.4 g of $Na_2SO_4.10H_2O$. The solids were filtered out. The resulting mixture was concentrated. This resulted in 1.8 g (crude) of 2-amino-2-[(2S)-1,4-dioxan-2-yl]ethanol as colorless oil. LCMS (ES, m/z): M+1: 148 Synthesis of 3-bromo-4-([1-[(2S)-1,4-dioxan-2-yl]-2-hydroxyethyl]amino)-5-nitrobenzenesulfonamide: Into a 50-mL round-bottom flask, was placed 3-bromo-4-chloro-5-nitrobenzenesulfonamide (1.19 g, 3.772 mmol, 1.00 equiv), 2-amino-2-[(2S)-1,4-dioxan-2-yl]ethanol (0.72 g, 0.005 mmol, 1.3 equiv), $CH_3CN$ (30.00 mL), DIEA (1.46 g, 0.011 mmol, 3 equiv). The resulting solution was stirred for 48 h at 80 degrees C. in an oil bath. The resulting mixture was concentrated. The residue was applied onto a silica gel column and eluted with ethyl acetate/petroleum ether (9:1). The collected fractions were combined and concentrated. This resulted in 120 mg (7.46%) of 3-bromo-4-([1-[(2S)-1,4-dioxan-2-yl]-2-hydroxyethyl]amino)-5-nitrobenzenesulfonamide as a yellow solid. LCMS (ES, m/z): M−1: 424

Synthesis of (3S)-3-[(2S)-1,4-dioxan-2-yl]-5-nitro-3,4-dihydro-2H-1,4-benzoxazine-7-sulfonamide &(3R)-3-[(2S)-1,4-dioxan-2-yl]-5-nitro-3,4-dihydro-2H-1,4-benzoxazine-7-sulfonamide (assumed): Into a 8-mL round-bottom flask purged and maintained with an inert atmosphere of nitrogen, was placed 3-bromo-4-([1-[(2S)-1,4-dioxan-2-yl]-2-hydroxyethyl]amino)-5-nitrobenzenesulfonamide (120 mg, 0.282 mmol, 1.00 equiv), dioxane (8.00 mL), $Cs_2CO_3$ (229.32 mg, 0.704 mmol, 2.50 equiv), t-BuXPhos Pd G3 (22.33 mg, 0.028 mmol, 0.1 equiv). The resulting solution was stirred for 8 h at 100 degrees C. in an oil bath. The reaction was then quenched by the addition of water (8 mL). The resulting solution was extracted with 3×8 mL of ethyl acetate concentrated. The crude product was purified by Prep-HPLC with the following conditions: Column, X-bridge RP18; mobile phase, 0.05% ammonia in water and $CH_3CN$ (45% $CH_3CN$ up to 60% in 5 min); Detector, UV 254 nm. This resulted in 7 mg (7.20%) of (3S or 3R)-3-[(2S)-1,4-dioxan-2-yl]-5-nitro-3,4-dihydro-2H-1,4-benzoxazine-7-sulfonamide as a yellow solid. This resulted in 10 mg (10.29%) of (3R or 3S)-3-[(2S)-1,4-dioxan-2-yl]-5-nitro-3,4-dihydro-2H-1,4-benzoxazine-7-sulfonamide as a yellow solid. LC-MS-6: (ES, m/z): M−1:344

Synthesis of 4-[2-[(2S)-2-(2-isopropylphenyl)pyrrolidin-1-yl]-7-azaspiro[3.5]nonan-7-yl]-N-[(3S)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed): Into a 20-mL vial, was placed 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoic acid (35.00 mg, 0.062 mmol, 1.00 equiv), DCM (3.00 mL), (3S)-5-nitro-3-(oxan-4-yl)-3,4-dihydro-2H-1,4-benzoxazine-7-sulfonamide (assumed) (22.00 mg, 0.064 mmol, 1.03 equiv), EDCI (24.00 mg, 0.125 mmol, 2.02 equiv), DMAP (30.00 mg, 0.246 mmol, 3.96 equiv). The resulting solution was stirred overnight at 30 degrees C. The resulting mixture was concentrated under vacuum. The crude product was purified by Prep-HPLC with the following conditions (2 #SHIMADZU (HPLC-01)): Column, XBridge Shield RP18 OBD Column, 19*150 mm, Sum; mobile phase, Water (0.05% $NH_3{\cdot}H_2O$) and ACN (41% Phase B up to 56% in 7 min); Detector, UV. This resulted in 15 mg (27.19%) of 4-[2-[(2S)-2-(2-isopropylphenyl)pyrrolidin-1-yl]-7-azaspiro[3.5]nonan-7-yl]-N-[(3S)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed) as a yellow solid. LC-MS-PH: (ES, m/z): M+1:890; H-NMR (300 MHz, DMSO-$d_6$, ppm) δ 11.59 (s, 1H), 8.72 (s, 1H), 8.14 (s, 1H), 7.99 (s, 1H), 7.52 (d, J=8.5 Hz, 2H), 7.46 (t, J=3.6 Hz, 2H), 7.31 (d, J=2.1 Hz, 1H), 7.23 (s, 1H), 7.15 (s, 2H), 6.69-6.62 (m, 1H), 6.35 (d, J=3.3 Hz, 1H), 6.18 (d, J=2.4 Hz, 1H), 4.30 (d, J=10.8 Hz, 1H), 4.02 (dd, J=11.3, 3.0 Hz, 1H), 3.86 (dd, J=11.4, 4.2 Hz, 2H), 3.70-3.60 (m, 1H), 3.51 (d, J=4.6 Hz, 1H), 3.24 (ddd, J=17.2, 13.1, 8.8 Hz, 2H), 3.01 (t, J=5.7 Hz, 2H), 2.92 (d, J=6.1 Hz, 2H), 2.68 (t, J=2.0 Hz, 1H), 2.33 (t, J=2.0 Hz, 1H), 2.21 (s, 1H), 1.90-1.35 (m, 16H), 1.17 (dd, J=12.8, 6.7 Hz, 6H).

Synthesis of 4-[2-[(2S)-2-(2-isopropylphenyl)pyrrolidin-1-yl]-7-azaspiro[3.5]nonan-7-yl]-N-[(3R)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed): Into a 20-mL vial, was placed 4-[2-[(2S)-2-(2-isopropylphenyl)pyrrolidin-1-yl]-7-azaspiro[3.5]nonan-7-yl]-2-[1H-pyrrolo[2,3-b]pyridin-5-yloxy]benzoic acid (35.00 mg, 0.062 mmol, 1.00 equiv), DCM (3.00 mL), (3R)-5-nitro-3-(oxan-4-yl)-3,4-dihydro-2H-1,4-benzoxazine-7-sulfonamide (assumed) (22.00 mg, 0.064 mmol, 1.03 equiv), EDCI (24.00 mg, 0.125 mmol, 2.02 equiv), DMAP (30.00 mg, 0.246 mmol, 3.96 equiv). The resulting solution was stirred overnight at 30 degrees C. The resulting mixture was concentrated under vacuum. The crude product was purified by Prep-HPLC with the following conditions (2 #SHIMADZU (HPLC-01)): Column, XBridge Shield RP18 OBD Column, 19*150 mm, 5 um; mobile phase, Water (0.05% $NH_3{\cdot}H_2O$) and ACN (39% PhaseB up to 54% in 7 min); Detector, UV. This resulted in 20 mg (36.26%) of 4-[2-[(2S)-2-(2-isopropylphenyl)pyrrolidin-1-yl]-7-azaspiro[3.5]nonan-7-yl]-N-[(3R)-5-nitro-3-(oxan-4-yl)-3,4-dihydro-2H-1,4-benzoxazin-7-ylsulfonyl]-2-[1H-pyrrolo[2,3-b]pyridin-5-yloxy]benzamide (assumed) as a yellow solid. LC-MS: (ES, m/z): M+1:890; H-NMR (300 MHz, DMSO-$d_6$, ppm) δ 11.59 (s, 1H), 8.72 (s, 1H), 8.14 (s, 1H), 7.99 (s, 1H), 7.52 (d, J=8.5 Hz, 2H), 7.46 (t, J=3.6 Hz, 2H), 7.31 (d, J=2.1 Hz, 1H), 7.23 (s, 1H), 7.15 (s, 2H), 6.69-6.62 (m, 1H), 6.35 (d, J=3.3 Hz, 1H), 6.18 (d, J=2.4 Hz, 1H), 4.30 (d, J=10.8 Hz, 1H), 4.02 (dd, J=11.3, 3.0 Hz, 1H), 3.86 (dd, J=11.4, 4.2 Hz, 2H), 3.70-3.60 (m, 1H), 3.51 (d, J=4.6 Hz, 1H), 3.24 (ddd, J=17.2, 13.1, 8.8 Hz, 2H), 3.01 (t, J=5.7 Hz, 2H), 2.92 (d, J=6.1 Hz, 2H), 2.68 (t, J=2.0 Hz, 1H), 2.33 (t, J=2.0 Hz, 1H), 2.21 (s, 1H), 1.90-1.35 (m, 16H), 1.17 (dd, J=12.8, 6.7 Hz, 6H).

The compounds below are prepared by methods substantially identical, similar, or analogous to those disclosed in above Schemes and Examples:

| Example | Chemical Name | m/z($MH^+$) |
|---|---|---|
| cpd-1 | N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(o-tolyl)pyrrolidin-1-yl)-7-azaspiro[3.5]nonan-7-yl)benzamide, | 917 |

-continued

| Example | Chemical Name | m/z(MH⁺) |
|---|---|---|
| cpd-2 | N-((3-nitro-4-(((tetrahydro-2H-pyran-4-yl)methyl)amino)phenyl)sulfonyl)-4-(2-((S)-2-(2-(prop-1-en-2-yl)phenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 943 |
| cpd-3 | N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-vinylphenyl)pyrrolidin-1-yl)-7-azaspiro[3.5]nonan-7-yl)benzamide, | 929 |
| cpd-4 | 4-(2-((S)-2-(2-ethylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 931 |
| cpd-5 | 4-(2-((S)-2-(2-cyclopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 943 |
| cpd-6 | 4-(2-((S)-2-(2-(tert-butyl)phenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 959 |
| cpd-7 | N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-(trifluoromethyl)phenyl)pyrrolidin-1-yl)-7-azaspiro[3.5]nonan-7-yl)benzamide, | 971 |
| cpd-8 | 4-(2-((S)-2-(2-ethynylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 927 |
| cpd-9 | N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(2-((S)-2-(2-(1,1,1-trifluoro-2-methylpropan-2-yl)phenyl)pyrrolidin-1-yl)-7-azaspiro[3.5]nonan-7-yl)benzamide, | 1013 |
| cpd-10 | 4-(2-((S)-2-(2-cyclobutylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 957 |
| cpd-11 | N-((3-nitro-4-(((tetrahydro-2H-pyran-4-yl)methyl)amino)phenyl)sulfonyl)-4-(2-((S)-2-(2-(prop-1-yn-1-yl)phenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 941 |
| cpd-12 | N-((4-((((S)-1,4-dioxan-2-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 947 |
| cpd-13 | N-((4-(((4-fluorotetrahydro-2H-pyran-4-yl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 963 |
| cpd-14 | 4-(2-((S)-2-(2-isopropylphenyl)pyrrolidin-1-yl)-7-azaspiro[3.5]nonan-7-yl)-N-((4-((((1r,4r)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |
| cpd-15 | 4-(2-((S)-2-(2-isopropylphenyl)pyrrolidin-1-yl)-7-azaspiro[3.5]nonan-7-yl)-N-((4-((((1s,4s)-4-methoxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |

-continued

| Example | Chemical Name | m/z(MH+) |
|---|---|---|
| cpd-16 | N-((4-((((1r,4r)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-17 | N-((4-((((1s,4s)-4-isopropoxy-4-methylcyclohexyl)methyl)amino)-3-nitrophenyl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-18 | 4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 973 |
| cpd-19 | 4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 973 |
| cpd-20 | N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 975 |
| cpd-21 | N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 975 |
| cpd-22 | N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |
| cpd-23 | N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |
| cpd-24 | N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |
| cpd-25 | N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 987 |
| cpd-26 | N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1001 |
| cpd-27 | N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1001 |

-continued

| Example | Chemical Name | m/z(MH+) |
|---|---|---|
| cpd-28 | N-(((R)-3-((1s,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1001 |
| cpd-29 | N-(((R)-3-((1r,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1001 |
| cpd-30 | 4-(2-((S)-2-(2-isopropylphenyl)pyrrolidin-1-yl)-7-azaspiro[3.5]nonan-7-yl)-N-(((S)-3-((1r,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-31 | 4-(2-((S)-2-(2-isopropylphenyl)pyrrolidin-1-yl)-7-azaspiro[3.5]nonan-7-yl)-N-(((S)-3-((1s,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-32 | 4-(2-((S)-2-(2-isopropylphenyl)pyrrolidin-1-yl)-7-azaspiro[3.5]nonan-7-yl)-N-(((R)-3-((1s,4S)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-33 | 4-(2-((S)-2-(2-isopropylphenyl)pyrrolidin-1-yl)-7-azaspiro[3.5]nonan-7-yl)-N-(((R)-3-((1r,4R)-4-methoxy-4-methylcyclohexyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1015 |
| cpd-34 | 4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 988 |
| cpd-35 | 4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 988 |
| cpd-36 | N-(((R)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1022 |
| cpd-37 | N-(((S)-3-((4,4-difluoropiperidin-1-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1022 |
| cpd-38 | N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1000 |
| cpd-39 | N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1000 |
| cpd-40 | N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7- | 1000 |

-continued

| Example | Chemical Name | m/z(MH+) |
|---|---|---|
| | azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | |
| cpd-41 | N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1000 |
| cpd-42 | N-(((R)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 961 |
| cpd-43 | N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 961 |
| cpd-44 | 4-(2-((S)-2-(2-isopropylphenyl)pyrrolidin-1-yl)-7-azaspiro[3.5]nonan-7-yl)-N-(((R)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 980 |
| cpd-45 | 4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 980 |
| cpd-46 | 4-(2-((S)-2-(2-isopropylphenyl)pyrrolidin-1-yl)-7-azaspiro[3.5]nonan-7-yl)-N-(((R)-3-((4-isopropylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1029 |
| cpd-47 | 4-(2-((S)-2-(2-isopropylphenyl)pyrrolidin-1-yl)-7-azaspiro[3.5]nonan-7-yl)-N-(((S)-3-((4-isopropylpiperazin-1-yl)methyl)-5-nitro-3,4-dihydro-2H-benzo[b][1,4]oxazin-7-yl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 1029 |
| cpd-48 | 4-(2-((S)-2-(2-isopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, | 1044 |
| cpd-49 | 4-(2-((S)-2-(2-isopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, | 1044 |
| cpd-50 | 4-(6-((S)-2-(2-isopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 917 |
| cpd-51 | N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, | 889 |
| cpd-52 | N-((3-nitro-4-(((tetrahydro-2H-pyran-4-yl)methyl)amino)phenyl)sulfonyl)-4-(6-((S)-2-(2-(prop-1-en-2-yl)phenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 915 |

-continued

| Example | Chemical Name | m/z(MH+) |
|---|---|---|
| cpd-53 | 4-(6-((S)-2-(2-ethylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 903 |
| cpd-54 | 4-(6-((S)-2-(2-cyclopropylphenyl)pyrrolidin-1-yl)-2-azaspiro[3.3]heptan-2-yl)-N-((3-nitro-4-(((tetrahydro-2H-pyran-4-yl)methyl)amino)phenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 915 |
| cpd-55 | N-((4-((((1r,4r)-4-hydroxy-4-methylcyclohexyl)methyl)amino)-3-nitrophenyl)sulfonyl)-4-(6-((S)-2-(2-isopropylphenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 945 |
| cpd-56 | 4-(6-((S)-2-(2-ethylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 931 |
| cpd-57 | N-((4-((((1r,4r)-4-hydroxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)-4-(6-((S)-2-(o-tolyl)pyrrolidin-1-yl)-2-azaspiro[3.3]heptan-2-yl)benzamide, | 917 |
| cpd-58 | 4-(6-((S)-2-(2-cyclopropylphenyl)pyrrolidin-1-yl)-2-azaspiro[3.3]heptan-2-yl)-N-((4-((((1r,4r)-4-hydroxy-4-methylcyclohexyl)methyl)amino)-3-nitrophenyl)sulfonyl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 943 |
| cpd-59 | N-((4-((((1r,4r)-4-hydroxy-4-methylcyclohexyl)methyl)amino)-3-nitrophenyl)sulfonyl)-4-(6-((S)-2-(2-(prop-1-en-2-yl)phenyl)pyrrolidin-1-yl)-2-azaspiro[3.3]heptan-2-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, | 943 |
| cpd-60 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, | 945 |
| cpd-61 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, | 945 |
| cpd-62 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aR)-6,7,9,9a-tetrahydro-1H-pyrano[3,4-b]pyrrolo[3',2':5,6]pyrido[3,2-e][1,4]oxazin-5(5aH)-yl)benzamide, | 959 |
| cpd-63 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aS)-6,7,9,9a-tetrahydro-1H-pyrano[3,4-b]pyrrolo[3',2':5,6]pyrido[3,2-e][1,4]oxazin-5(5aH)-yl)benzamide, | 959 |
| cpd-64 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aR)-6,7,9,9a-tetrahydro-1H-pyrano[3,4-b]pyrrolo[3',2':5,6]pyrido[3,2-e][1,4]oxazin-5(5aH)-yl)benzamide, | 959 |
| cpd-65 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aS)-6,7,9,9a-tetrahydro-1H-pyrano[3,4-b]pyrrolo[3',2':5,6]pyrido[3,2-e][1,4]oxazin-5(5aH)-yl)benzamide, | 959 |
| cpd-66 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aS)-5a,8,9,9a-tetrahydro-6H-pyrano[4,3-b]pyrrolo[3',2':5,6]pyrido[3,2-e][1,4]oxazin-5(1H)-yl)benzamide, | 959 |
| cpd-67 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aR)-5a,8,9,9a- | 959 |

-continued

| Example | Chemical Name | m/z(MH⁺) |
|---|---|---|
| | tetrahydro-6H-pyrano[4,3-b]pyrrolo[3',2':5,6]pyrido[3,2-e][1,4]oxazin-5(1H)-yl)benzamide | |
| cpd-68 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aR,9aS)-5a,8,9,9a-tetrahydro-6H-pyrano[4,3-b]pyrrolo[3',2':5,6]pyrido[3,2-e][1,4]oxazin-5(1H)-yl)benzamide, | 959 |
| cpd-69 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((5aS,9aR)-5a,8,9,9a-tetrahydro-6H-pyrano[4,3-b]pyrrolo[3',2':5,6]pyrido[3,2-e][1,4]oxazin-5(1H)-yl)benzamide, | 959 |
| cpd-70 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,9aS)-6a,7,9,9a-tetrahydro-1H-furo[3,4-f]pyrrolo[3',2':5,6]pyrido[2,3-b][1,4]oxazepin-5(6H)-yl)benzamide, | 959 |
| cpd-71 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,9aR)-6a,7,9,9a-tetrahydro-1H-furo[3,4-f]pyrrolo[3',2':5,6]pyrido[2,3-b][1,4]oxazepin-5(6H)-yl)benzamide, | 959 |
| cpd-72 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,9aR)-6a,7,9,9a-tetrahydro-1H-furo[3,4-f]pyrrolo[3',2':5,6]pyrido[2,3-b][1,4]oxazepin-5(6H)-yl)benzamide, | 959 |
| cpd-73 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,9aS)-6a,7,9,9a-tetrahydro-1H-furo[3,4-f]pyrrolo[3',2':5,6]pyrido[2,3-b][1,4]oxazepin-5(6H)-yl)benzamide | 959 |
| cpd-74 | 2-((6aR,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, | 973 |
| cpd-75 | 2-((6aS,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, | 973 |
| cpd-76 | 2-((6aS,10aR)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, | 973 |
| cpd-77 | 2-((6aR,10aS)-6,6a,7,8,10,10a-hexahydropyrano[4,3-f]pyrrolo[3',2':5,6]pyrido[2,3-b][1,4]oxazepin-5(1H)-yl)-4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)benzamide, | 973 |
| cpd-78 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, | 973 |
| cpd-79 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, | 973 |
| cpd-80 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aR,10aS)-6a,9,10,10a-tetrahydro-1H,7H-pyrano[3,4-f]pyrrolo[3',2':5,6]pyrido[2,3-b][1,4]oxazepin-5(6H)-yl)benzamide, | 973 |
| cpd-81 | 4-(2-((S)-2-(2-isopropylphenyl)pyrrolidin-1-yl)-7-azaspiro[3.5]nonan-7-yl)-N-((3-nitro-4-(((tetrahydro-2H-pyran-4-yl)methyl)amino)phenyl)sulfonyl)-2-((6aS,10aR)-6a,9,10,10a-tetrahydro-1H,7H-pyrano[3,4-f]pyrrolo[3',2':5,6]pyrido[2,3-b][1,4]oxazepin-5(6H)-yl)benzamide, | 973 |

-continued

| Example | Chemical Name | m/z(MH+) |
|---|---|---|
| cpd-82 | N-(((S)-3-((S)-1,4-dioxan-2-yl)-5-nitro-3,4-dihydro-2H-benzo[b][1,4]oxazin-7-yl)sulfonyl)-2-((1 H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide, | 892 |
| cpd-83 | N-(((R)-3-((S)-1,4-dioxan-2-yl)-5-nitro-3,4-dihydro-2H-benzo[b][1,4]oxazin-7-yl)sulfonyl)-2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)benzamide, | 892 |
| cpd-84 | 2-((1H-pyrrolo[2,3-b]pyridin-5-yl)oxy)-N-(((S)-3-((1s,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 904 |
| cpd-85 | 2-((1H-pyrrolo[2,3-b]pyridin-5-yl)oxy)-N-(((S)-3-((1r,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 904 |
| cpd-86 | 2-((1H-pyrrolo[2,3-b]pyridin-5-yl)oxy)-N-(((R)-3-((1r,4R)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 904 |
| cpd-87 | 2-((1H-pyrrolo[2,3-b]pyridin-5-yl)oxy)-N-(((R)-3-((1s,4S)-4-hydroxycyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 904 |
| cpd-88 | 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 918 |
| cpd-89 | 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 918 |
| cpd-90 | 2-((1H-pyrrolo[2,3-b]pyridin-5-yl)oxy)-N-(((S)-3-((1r,4S)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 918 |
| cpd-91 | 2-((1H-pyrrolo[2,3-b]pyridin-5-yl)oxy)-N-(((S)-3-((1s,4R)-4-hydroxy-4-methylcyclohexyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 918 |
| cpd-92 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, | 961 |
| cpd-93 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-((2R,5R)-5-methyl-4-(oxetan-3-yl)morpholin-2-yl)-5-nitro-3,4-dihydro-2H-benzo[b][1,4]oxazin-7-yl)sulfonyl)benzamide, | 961 |
| cpd-94 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-(morpholinomethyl)-5-nitro-3,4-dihydro-2H-benzo[b][1,4]oxazin-7-yl)sulfonyl)benzamide, | 905 |
| cpd-95 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-(morpholinomethyl)-5-nitro-3,4-dihydro-2H-benzo[b][1,4]oxazin-7-yl)sulfonyl)benzamide, | 905 |
| cpd-96 | 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 917 |
| cpd-97 | 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 917 |

-continued

| Example | Chemical Name | m/z(MH+) |
| --- | --- | --- |
| cpd-98 | 2-((1H-pyrrolo[2,3-b]pyridin-5-yl)oxy)-N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 917 |
| cpd-99 | 2-((1H-pyrrolo[2,3-b]pyridin-5-yl)oxy)-N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 917 |
| cpd-100 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-((4-methylpiperazin-1-yl)methyl)-5-nitro-3,4-dihydro-2H-benzo[b][1,4]oxazin-7-yl)sulfonyl)benzamide, | 918 |
| cpd-101 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-((4-methylpiperazin-1-yl)methyl)-5-nitro-3,4-dihydro-2H-benzo[b][1,4]oxazin-7-yl)sulfonyl)benzamide, | 918 |
| cpd-102 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, | 974 |
| cpd-103 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide, | 974 |
| cpd-104 | 2-((1H-pyrrolo[2,3-b]pyridin-5-yl)oxy)-N-(((S)-3-(isopropoxymethyl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)benzamide, | 878 |
| cpd-105 | 2-((1H-pyrrolo[2,3-b]pyridin-5-yl)oxy)-4-(2-((S)-2-(2-isopropylphenyl)pyrrolidin-1-yl)-7-azaspiro[3.5]nonan-7-yl)-N-(((S)-5-nitro-3-(pyridin-2-ylmethyl)-3,4-dihydro-2H-benzo[b][1,4]oxazin-7-yl)sulfonyl)benzamide, | 897 |
| cpd-106 | 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide, | 888 |
| cpd-107 | 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(prop-1-en-2-yl)phenyl)pyrrolidin-1-yl)-7-azaspiro[3.5]nonan-7-yl)benzamide | 888 |
| cpd-108 | 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide, | 862 |
| cpd-109 | 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(o-tolyl)pyrrolidin-1-yl)-7-azaspiro[3.5]nonan-7-yl)benzamide | 862 |
| cpd-110 | 2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide, | 876 |
| cpd-111 | 2-((1H-pyrrolo[2,3-b]pyridin-5-yl)oxy)-4-(2-((S)-2-(2-ethylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide, | 876 |
| cpd-112 | 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide, | 888 |
| cpd-113 | 2-((1H-pyrrolo[2,3-b]pyridin-5-yl)oxy)-4-(2-((S)-2-(2-cyclopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide, | 888 |
| cpd-114 | 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(trifluoromethyl)phenyl)pyrrolidin-1-yl)-7-azaspiro[3.5]nonan-7-yl)benzamide | 916 |

-continued

| Example | Chemical Name | m/z(MH⁺) |
|---|---|---|
| cpd-115 | 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(trifluoromethyl)phenyl)pyrrolidin-1-yl)-7-azaspiro[3.5]nonan-7-yl)benzamide | 916 |
| cpd-116 | 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-vinylphenyl)pyrrolidin-1-yl)-7-azaspiro[3.5]nonan-7-yl)benzamide | 874 |
| cpd-117 | 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-vinylphenyl)pyrrolidin-1-yl)-7-azaspiro[3.5]nonan-7-yl)benzamide | 874 |
| cpd-118 | 2-((1H-pyrrolo[2,3-b]pyridin-5-yl)oxy)-4-(2-((S)-2-(2-ethynylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide | 872 |
| cpd-119 | 2-((1H-pyrrolo[2,3-b]pyridin-5-yl)oxy)-4-(2-((S)-2-(2-ethynylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide | 872 |
| cpd-120 | 2-((1H-pyrrolo[2,3-b]pyridin-5-yl)oxy)-4-(2-((S)-2-(2-cyclobutylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide | 902 |
| cpd-121 | 2-((1H-pyrrolo[2,3-b]pyridin-5-yl)oxy)-4-(2-((S)-2-(2-cyclobutylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide | 902 |
| cpd-122 | 2-((1H-pyrrolo[2,3-b]pyridin-5-yl)oxy)-4-(2-((S)-2-(2-(tert-butyl)phenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide | 904 |
| cpd-123 | 2-((1H-pyrrolo[2,3-b]pyridin-5-yl)oxy)-4-(2-((S)-2-(2-(tert-butyl)phenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide | 904 |
| cpd-124 | 2-((1H-pyrrolo[2,3-b]pyridin-5-yl)oxy)-N-(((R)-5-nitro-3-(tetrahydro-2H-pyran-4-yl)-3,4-dihydro-2H-benzo[b][1,4]oxazin-7-yl)sulfonyl)-4-(2-((S)-2-(2-(1,1,1-trifluoro-2-methylpropan-2-yl)phenyl)pyrrolidin-1-yl)-7-azaspiro[3.5]nonan-7-yl)benzamide | 958 |
| cpd-125 | 2-((1H-pyrrolo[2,3-b]pyridin-5-yl)oxy)-N-(((S)-5-nitro-3-(tetrahydro-2H-pyran-4-yl)-3,4-dihydro-2H-benzo[b][1,4]oxazin-7-yl)sulfonyl)-4-(2-((S)-2-(2-(1,1,1-trifluoro-2-methylpropan-2-yl)phenyl)pyrrolidin-1-yl)-7-azaspiro[3.5]nonan-7-yl)benzamide | 958 |
| cpd-126 | 2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)-N-(((R)-5-nitro-3-(tetrahydro-2H-pyran-4-yl)-3,4-dihydro-2H-benzo[b][1,4]oxazin-7-yl)sulfonyl)benzamide | 862 |
| cpd-127 | 2-((1H-pyrrolo[2,3-b]pyridin-5-yl)oxy)-4-(6-((S)-2-(2-isopropylphenyl)pyrrolidin-1-yl)-2-azaspiro[3.3]heptan-2-yl)-N-(((S)-5-nitro-3-(tetrahydro-2H-pyran-4-yl)-3,4-dihydro-2H-benzo[b][1,4]oxazin-7-yl)sulfonyl)benzamide | 862 |
| cpd-128 | 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((R)-5-nitro-3-(tetrahydro-2H-pyran-4-yl)-3,4-dihydro-2H-benzo[b][1,4]oxazin-7-yl)sulfonyl)benzamide | 945 |
| cpd-129 | 4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)-N-(((S)-5-nitro-3-(tetrahydro-2H-pyran-4-yl)-3,4-dihydro-2H-benzo[b][1,4]oxazin-7-yl)sulfonyl)benzamide | 945 |
| cpd-130 | N-(((S)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide | 947 |
| cpd-131 | N-(((R)-3-((S)-1,4-dioxan-2-yl)-5-nitro-3,4-dihydro-2H-benzo[b][1,4]oxazin-7-yl)sulfonyl)-4-(2-((S)-2-(2-isopropylphenyl)pyrrolidin-1-yl)-7-azaspiro[3.5]nonan-7-yl)-2-((R)-3-methyl-2,3-dihydropyrrolo[3',2':5,6]pyrido[2,3-b][1,4]oxazin-1(6H)-yl)benzamide | 947 |

-continued

| Example | Chemical Name | m/z(MH+) |
|---|---|---|
| cpd-132 | 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((R)-5-nitro-3-(tetrahydro-2H-pyran-4-yl)-3,4-dihydro-2H-benzo[b][1,4]oxazin-7-yl)sulfonyl)benzamide | 945 |
| cpd-133 | 2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)-N-(((S)-5-nitro-3-(tetrahydro-2H-pyran-4-yl)-3,4-dihydro-2H-benzo[b][1,4]oxazin-7-yl)sulfonyl)benzamide | 945 |
| cpd-134 | N-(((S)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide | 947 |
| cpd-135 | N-(((R)-3-((S)-1,4-dioxan-2-yl)-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)-4-(2-((S)-2-(2-isopropylphenyl)pyrrolidin-1-yl)-7-azaspiro[3.5]nonan-7-yl)benzamide | 947 |

Biological Example 1: Bcl-2 Competition Binding (Fluorescence Polarization) Assay The fluorescence-labeled 23 amino acid peptide BH3 was purchased from CalBiochem (NLWAAQRYGREL-RRMSDKFVD). An unbound Fluorescein labeled BH3 peptide emits random light with respect to the plane of polarization plane of excited light, resulting in a lower polarization degree (mP) value. When the peptide is bound to Bcl-2, the complex tumble slower and the emitted light can have a higher level of polarization, resulting in a higher mP value. This binding assay was performed in 96-well plate and with each assay contained 15 and 30 nM of labeled peptide and purified Bcl-2 protein (purchased from R&D Systems, Inc). The assay buffer contained 20 mM Hepes (pH 7.0), 50 mM KCl, 5 mM $MgCl_2$, 20 mM $Na_2MoO_4$, 0.1 mg/ml Bovine Gamma Globulin and 0.01% NP40. Compounds were diluted in DMSO and added to the final assay with concentration range from 20 M to 2 nM. The polarization degree (mP) value was determined by BioTek Synergy II with background subtraction after 3 hours of incubation at room temperature. $IC_{50}$ was calculated using Prism software with sigmoidal dose-response curve fitting. ABT-737 was used as reference compound. Such assays, carried out with a range of doses of test compounds, allowed the determination of an approximate $IC_{50}$ value. Although the inhibitory properties of the compounds of the present invention vary with structural change as expected, the activity generally exhibited by these agents was in the range of $IC_{50}$=0.1-1000 nM.

Biological Example 2: In Vitro Anti-Proliferation Assay in BCL-2-Dependent Acute Lymphoblastic Leukemia (ALL) Cell Line RS4;11

Cell antiproliferation was assayed by PerkinElmer ATPlite™ Luminescence Assay System. Briefly, the various test cancer cell lines were plated at a density of about $1\times10^4$ cells per well in Costar 96-well plates, and were incubated with different concentrations of compounds for about 72 hours in medium supplemented with 5% FBS or 10% normal human serum (NHS). One lyophilized substrate solution vial was then reconstituted by adding 5 mL of substrate buffer solution, and was agitated gently until the solution was homogeneous. About 50 μL of mammalian cell lysis solution was added to 100 μL of cell suspension per well of a microplate, and the plate was shaken for about five minutes in an orbital shaker at −700 rpm. This procedure was used to lyse the cells and to stabilize the ATP. Next, 50 μL substrate solution was added to the wells and microplate was shaken for five minutes in an orbital shaker at −700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention. The following table lists the $IC_{50}$ values of certain compounds of the invention.

Biological Example 3: Mice PK Study

The pharmacokinetics of compounds were evaluated in CD-1 mouse via Intravenous and Oral Administration. The IV dose was administered as a slow bolus in the Jugular vein, and oral doses were administered by gavage. The formulation for IV dosing was 5% DMSO in 20% HPBCD in water, and the PO formulation was 2.5% DMSO, 10% EtOH, 20% Cremphor EL, 67.5% D5W. The PK time point for the IV arm was 5, 15, 30 min, 1, 2, 4, 6, 8, 12, 24 hours post dose, and for PO arm was 15, 30 min, 1, 2, 4, 6, 8, 12, 24 hours post dose. Approximately 0.03 mL blood was collected at each time point. Blood of each sample was transferred into plastic micro centrifuge tubes containing EDTA-K2 and collect plasma within 15 min by centrifugation at 4000 g for 5 minutes in a 4° C. centrifuge. Plasma samples were stored in polypropylene tubes. The samples were stored in a freezer at −75±15° C. prior to analysis. Concentrations of compounds in the plasma samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data was described using descriptive statistics such as mean, standard deviation. Additional pharmacokinetic or statistical analysis was performed at the discretion of the contributing scientist, and was documented in the data summary.

Biological Example 4: In Vivo Xenograft Studies

Compound of Example 3 is selected for in vivo studies in the BCL-2-dependent acute lymphoblastic leukemia (ALL) RS4;11 xenograft model. The CB.17 SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 $mm^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of ≤42% are considered significant.

What is claimed is:

1. A compound of Formula (I), or an N oxide thereof, or a pharmaceutically acceptable salt thereof:

Formula (I)

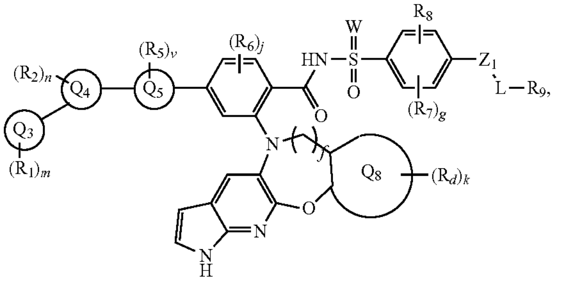

wherein $Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is cycloalkyl, cycloalkenyl, heterocycloalkyl, heterocycloalkenyl, aryl, heteroaryl, or spiro-heterocyclic;

$Q_8$ is cycloalkyl, cycloalkenyl, heterocycloalkyl, heterocycloalkenyl, aryl, heteroaryl, or spiro-heterocyclic;

each of $R_1$, $R_2$, $R_5$, $R_6$, $R_7$, $R_8$, and $R_9$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, $—P(O)R_bR_c$, -alkyl-$P(O)R_bR_c$, $—S(O)(=N(R_b))R_c$, $—N=S(O)R_bR_c$, $=NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, $—P(O)R_eR_e$, -alkyl-$P(O)R_eR_e$, $—S(O)(=N(R_e))R_e$, $—N=S(O)R_eR_e$, $=NR_e$, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O) NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

W is O or $N(R_a)$;

each of $Z_1$ and $Z_2$, independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

L is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

two of $R_1$ group, taken together with the atom to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom to which they are attached, may optionally form a cycloalkyl or heterocycloalkyl, in which said cycloalkyl or heterocycloalkyl of $R_2$, is optionally substituted with one or more $R_d$;

two of $R_5$ group, taken together with the atom to which they are attached, may optionally form a cycloalkyl or heterocycloalkyl, in which said cycloalkyl or heterocycloalkyl of $R_5$, is optionally substituted with one or more $R_d$;

$R_7$ and $R_8$ group, taken together with the atom to which they are attached, may optionally form a cycloalkyl or heterocycloalkyl, in which said cycloalkyl or heterocycloalkyl of $R_7$ or $R_8$, is optionally substituted with one or more $R_d$;

$R_7$ and $—Z_1$-L-$R_9$ group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of $R_7$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_d$ group, taken together with the atom to which they are attached, may optionally form a cycloalkyl, or heterocycloalkyl, in which said cycloalkyl or heterocycloalkyl of $R_d$, is optionally substituted with one or more $R_e$;

two of $R_e$ group, taken together with the atom to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of m, n, j, k, v, and g is, independently, 0, 1, 2, 3, 4, 5, 6, 7, or 8;

f is 0, 1, or 2; and each of p, and q is, independently, 0, 1, 2, 3, 4, or 5.

2. The compound according to claim 1, or a pharmaceutically acceptable salt thereof, wherein i) the compound is represented by Formula (II):

Formula (II)

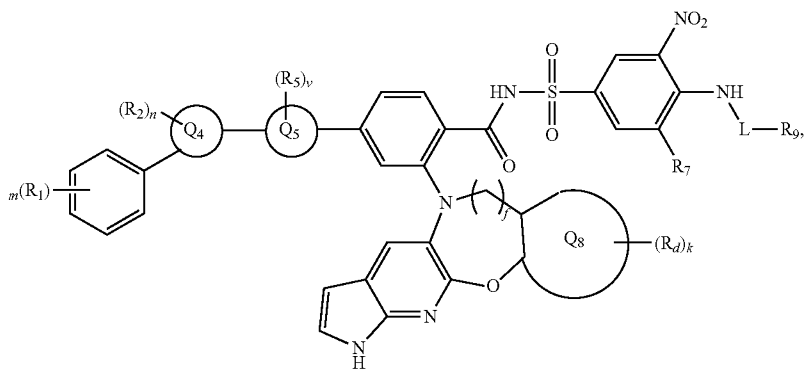

wherein $Q_4$ is heterocycloalkyl; and $Q_5$ is aryl or spiro heterocyclic;

ii) the compound is represented by Formula (III):

Formula (III)

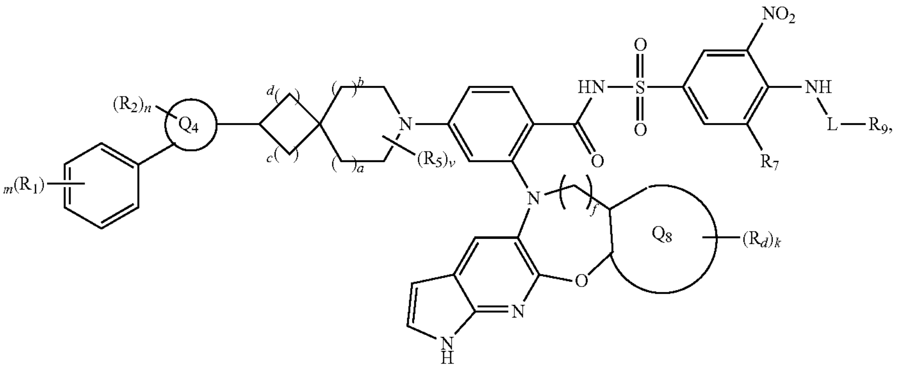

wherein each of a, b, c, and d, independently, is 0, 1, or 2;

iii) the compound is represented by Formula (IV):

Formula (IV)

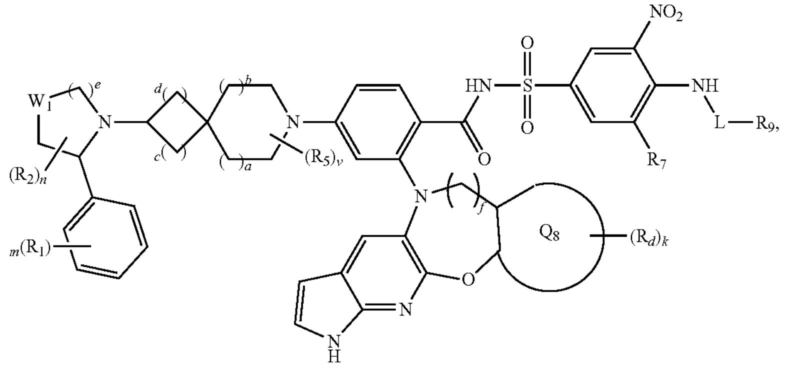

wherein e is 0, 1, or 2; and $W_1$ is O, S, $N(R_a)$, $C(R_aR_b)$;

iv) the compound is represented by Formula (V):

Formula (V)

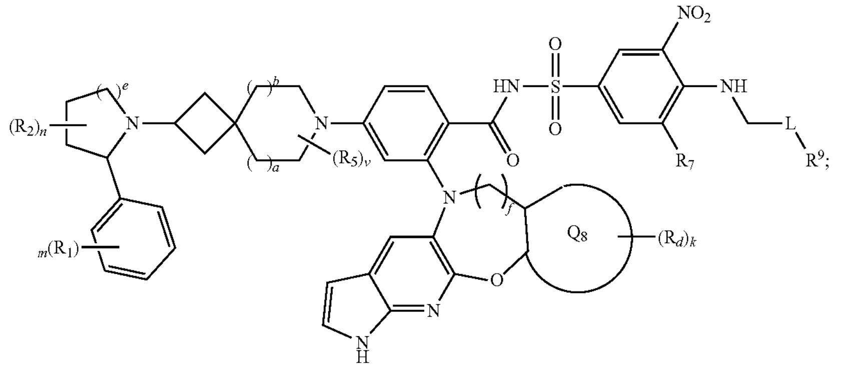

or, v) the compound is represented by Formula (VI):

Formula (VI)

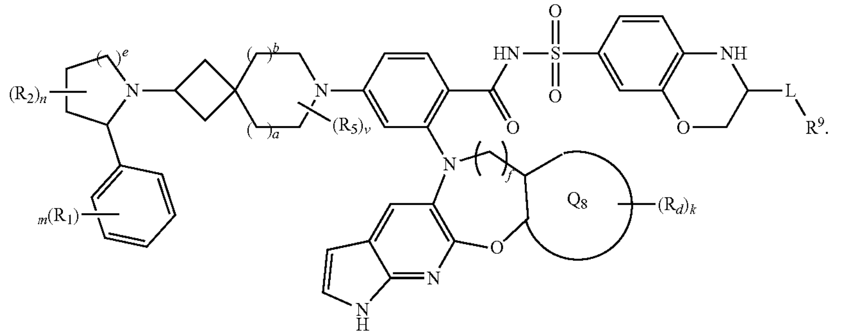

3. A pharmaceutical composition comprising a compound of Formula (I) as defined in claim 1, or a pharmaceutically acceptable salt thereof, and a pharmaceutically acceptable diluent or carrier.

* * * * *